United States Patent
Wencewicz et al.

(10) Patent No.: US 12,421,187 B2
(45) Date of Patent: Sep. 23, 2025

(54) DIHYDROFOLATE SYNTHASE (DHFS) INHIBITING AGENTS AND METHODS OF MAKING AND USING SAME

(71) Applicants: Timothy Wencewicz, St. Louis, MO (US); Brett Virgin-Downey, St. Louis, MO (US)

(72) Inventors: Timothy Wencewicz, St. Louis, MO (US); Brett Virgin-Downey, St. Louis, MO (US)

(73) Assignee: Washington Univeristy, St. Louis, MO (US)

( * ) Notice: Subject to any disclaimer, the term of this patent is extended or adjusted under 35 U.S.C. 154(b) by 0 days.

(21) Appl. No.: 18/297,368

(22) Filed: Apr. 7, 2023

(65) Prior Publication Data
US 2023/0322667 A1   Oct. 12, 2023

Related U.S. Application Data

(60) Provisional application No. 63/328,949, filed on Apr. 8, 2022.

(51) Int. Cl.
| | |
|---|---|
| *C07D 205/04* | (2006.01) |
| *A61K 31/397* | (2006.01) |
| *A61K 31/42* | (2006.01) |
| *A61K 31/505* | (2006.01) |
| *A61K 31/506* | (2006.01) |
| *A61K 31/519* | (2006.01) |
| *A61P 31/14* | (2006.01) |
| *C07D 403/12* | (2006.01) |
| *C07D 487/04* | (2006.01) |

(52) U.S. Cl.
CPC .......... *C07D 205/04* (2013.01); *A61K 31/397* (2013.01); *A61K 31/42* (2013.01); *A61K 31/505* (2013.01); *A61K 31/506* (2013.01); *A61K 31/519* (2013.01); *A61P 31/14* (2018.01); *C07D 403/12* (2013.01); *C07D 487/04* (2013.01)

(58) Field of Classification Search
CPC .. A61K 31/397; A61K 31/505; A61K 31/506; A61K 31/519; A61K 31/42; C07D 205/04; C07D 403/12; C07D 487/04; A61P 31/00
See application file for complete search history.

(56) References Cited

U.S. PATENT DOCUMENTS 10,363,250 B2   7/2019   Leamon et al.

FOREIGN PATENT DOCUMENTS

WO   2004011005 A2   2/2004

OTHER PUBLICATIONS

Markley et al., Stream-lined synthesis of 3-hydroxy-β-lactams: Norrish-Yang type II photocyclizations of β-ketoformamides, Tetrahedron, vol. 74, 2743-2753, Apr. 10, 2018 (Year: 2018).*
Ho et al., Mechanism of Sulfonamide Resistance and Synergism in Pathogens, Contract No. DAMD17-74-C-4039, Massachusetts College of Pharmacy, Jun. 1978 (Year: 1978).*

(Continued)

*Primary Examiner* — Sarah Pihonak
*Assistant Examiner* — Padmaja S Rao

(57) ABSTRACT

The present disclosure provides for compositions of, synthetic methods of, and methods for use of dihydrofolate synthase (DHFS) inhibiting agents.

20 Claims, 51 Drawing Sheets

(56) References Cited

OTHER PUBLICATIONS

Fernley et al. A rapid assay for dihydropteroate synthase activity suitable for identification of inhibitors, Analytical Biochemistry, 2007, vol. 360, Issue 2, pp. 227-234.

Angelastro et al. Chemoenzymatic Assembly of Isotopically Labeled Folates, Journal of the American Chemical Society, 2017, vol. 139, Issue 37, pp. 13047-54.

Kitz et al. Esters of methanesulfonic acid as irreversible inhibitors of acetylcholinesterase, Journal of Biological Chemistry, 1962, vol. 237, Issue 10, pp. 3245-3249.

Berenbaum, A Method for Testing for Synergy with Any Number of Agents, The Journal of Infectious Diseases, 1978, vol. 137, Issue 2, pp. 122-130.

Schittmayer et al. Quantification of Cellular Folate Species by LC-MS after Stabilization by Derivatization, Analytical Chemistry, 2018, vol. 90, Issue 12, pp. 7349-7356.

Dawadi et al. Synthesis and Analysis of Bacterial Folate Metabolism Intermediates and Antifolates, Organic Letters, 2017, vol. 19, Issue 19, pp. 5220-5223.

Afanasyev et al. Reductive Animation in the Synthesis of Pharmaceuticals, Chemical reviews, 2019, vol. 119, Issue 23, pp. 11857-911.

Gradmann, Book Review: The first miracle drugs: how the sulfa drugs transformed medicine, Medical History, 2008, vol. 52, Issue 3, pp. 416-417.

Swanson, Drug Metabolism by the Host and Gut Microbiota: A Partnership or Rivalry?, Drug Metabolism and Disposition, 2015, vol. 43, Issue 10, pp. 1499-1504.

Southeast Enzyme Conference, 11th Annual Southeast Enzyme Conference Program, 2021.

Patrick G. J., et al., Mechanistic Basis for ATP-Dependent Inhibition of Glutamine Synthetase by Tabtoxinine-β-Lactam, Biochemistry, 2018, vol. 57, Issue 1, pp. 117-135.

Hart et. al., Tabtoxinine-β-Lactam is a 'stealth' β-lactam antibiotic that evades β-lactamase-mediated antibiotic resistance, MedChemComm, 2016, vol. 7, pp. 118-127.

Wang et. al., Characterization of the bifunctional dihydrofolate synthase-folypolyglutamate synthase from Plasmodium faciparum; a potential novel target for antimalarial antifolate inhibition, Molecular and Biochemical Parasitology, 2010, vol. 172, Issue 1, pp. 41-51.

Markley et al., Stream-lined synthesis of 3-hydroxy-β-lactams: Norrish-Yang type II photocyclizations of β-ketoformamides, Tetrahedron, 2018, vol. 74, pp. 2743-2753.

HHS & CDC (U.S. Department of Health and Human Services & Centers for Disease Control and Prevention), Antibodies Resistance Threats in the United States, 2019, U.S. Centers for Disease Control and Prevention.

Abelenda-Alonso et al. Antibiotic prescription during the COVID-19 pandemic: A biphasic pattern, Infection Control & Hospital Epidemiology, 2020, vol. 41, pp. 1371-1372.

Chen et al. The microbial coinfection in COVID-19, Applied Microbiology an Biotechnology, 2020, vol. 104, pp. 7777-7785.

Wencewicz, New antibiotics from Nature's chemical inventory, Bioorganic & Medicinal Chemistry, 2016, vol. 24, pp. 6227-6252.

Payne et al. Drugs for bad bugs: confronting the challenges of antibacterial discovery, Nature Reviews Drug Discovery, 2007, vol. 6, pp. 29-40.

Brown et al. Antibacterial drug discovery in the resistance era, Nature, 2016, vol. 529, pp. 336-343.

Hamad, The antibiotics market, Nature Reviews Drug Discovery, 2010, vol. 9, pp. 675-676.

Fisher et al. Endless resistance. Endless antibiotics?, MedChemCommun, 2015, vol. 7, pp. 37-49.

Cooper, A community-based approach to new antibiotic discovery, Nature Reviews Drug Discovery, 2015, vol. 14, pp. 587-588.

Rossi et al. Folate Production by Probiotic Bacteria, Nutrients, 2011, vol. 3, Issue 1, pp. 118-134.

Bourne, Utility of the Biosynthetic Folate Pathway for Targets in Antimicrobial Discovery, Antibiotics, 2014, vol. 3, Issue 1, pp. 1-28.

Maskell et al. Mechanism of sulfonamide resistance in clinical isolates of Streptococcus, Antimicrobial Agents and Chemotherapy, 1997, vol. 41, Issue 10, pp. 2121-2126.

Yun et al. Catalysis and Sulfa Drug Resistance in Dihydropteroate Synthase, Science, 2012, vol. 335, Issue 6072, pp. 1110-1114.

Dale et al. A single amino acid substitution in Staphylococcus aureus dihydrofolate reductase determines trimethoprim resistance, Journal of Molecular Biology, 1997, vol. 266, Issue 1, pp. 23-30.

Blahna et al. The role of horizontal gene transfer in the spread of trimethoprim—sulfamethoxazole resistance among uropathogenic Escherichia coli in Europe and Canada, Journal of Antimicrobial Chemotherapy, 2006, vol. 57, Issue 4, pp. 666-672.

Minato et al. Mutual potentiation drives synergy between trimethoprim and sulfamethoxazole, Nature Communications, 2018, vol. 9, Article No. 1003.

Wormser et al. Co-trimoxazole (Trimethoprim-sulfamethoxazole) An Updated Review of its Antibacterial Activity and Clinical Efficacy, Drug Evaluations, 2012, vol. 24, pp. 459-518.

Mathieu et al. Escherichia coli FolC Structure Reveals an Unexpected Dihydrofolate Binding Site Providing an Attractive Target for Anti-microbial Therapy, Journal of Biological Chemistry, 2005, vol. 280, Issue 19.

Banerjee et al. Dihydrofolate Synthetase and Folylpolyglutamate Synthetase: Direct Evidence for Intervention of Acyl Phosphate Intermediates, Biochemistry, 1988, vol. 27, pp. 9062-9070.

Shane, Pteroylpoly(gamma-glutamate) synthesis by Corynebacterium species. Purification and properties of folypoly (gamma-glutamate) synthetase, The Journal of Biological Chemistry, 1980, vol. 255, Issue 12, pp. P5655-P5652.

Sun et al. Folate-binding Triggers the Activation of Folylpolyglutamate Synthetase, Journal of Molecular Biology, 2001, vol. 310, Issue 5, pp. 1067-1078.

Bartley et al. A Stereoselective Synthesis of Phosphinic Acid Phosphapeptides Corresponding to Glutamyl-γ-glutamate and Incorporation into Potent Inhibitors of Folylpoly-γ-glutamyl Synthetase, Journal of Organic Chemistry, 2005, vol. 70, Issue 17, pp. 6757-6774.

Yang et al. Synthesis of p-Aminophenyl Aryl H-Phosphinic Acids and Esters via Cross-Coupling Reactions: Elaboration to Phosphinic Acid Pseudopeptide Analogues of Pteroyl Glutamic Acid and Related Antifolates, Journal of Organic Chemistry, 2007, vol. 72, Issue 15, pp. 5748-5758.

Krajewski et al. Structure of Mycobacterium tuberculosis glutamine synthetase in complex with a transition-state mimic provides functional insights, Proceedings of the National Academy of Sciences, 2005, vol. 103, Issue 30, pp. 10499-504.

Galperin et al. A diverse superfamily of enzymes with ATP-dependent carboxylate-amine/thiol ligase activity, Protein Science, 1997, vol. 6, Issue 12, pp. 2639-2643.

Lyer et al. Amidoligases with ATP-grasp, glutamine synthetase-like and acetyltransferase-like domains: synthesis of novel metabolites and peptide modifications of proteins, 2009, vol. 5, pp. 1636-1660.

Dolle et al. ATP-citrate-lyase as a target for hypolipidemic intervention. Sulfoximine and 3-hydroxy-. beta.-lactam containing analogs of citric acid as potential tight-binding inhibitors, Journal of medicinal chemistry, 1992, vol. 35, Issue 26, pp. 4875-4884.

Verschueren et al. Structure of ATP citrate lyase and the origin of citrate synthase in the Krebs cycle, Nature, 2019, vol. 58, pp. 571-575.

Richter et al. Predictive compound accumulation rules yield a broad-spectrum antibiotic, Nature, 2017, vol. 545, pp. 299-304.

Achari et al. Cyrstal structure of the anti-bacterial sulfonamide drug target dihydropteroate synthase, Nature Structural Biology, 2017, vol. 4, pp. 490-497.

Gotham et al. Estimated generic prices for novel treatments for drug-resistant tuberculosis, Journal of Antimicrobial Chemotherapy, 2017, vol. 72, Issue 4, pp. 1243-1252.

Tyers et al. Drug combinations: a strategy to extend the life of antibiotics in the 21st century, Nature Reviews Microbiology, 2019, vol. 17, pp. 141-155.

(56) References Cited

OTHER PUBLICATIONS

Minato et al. Subversion of Metabolic Wasting as the Mechanism for folM-Linked Sulfamethoxazole Resistance, mBio, 2017, vol. 8, Issue 6, 10.1128.

Azzam et al. Design, Synthesis, and Antimicrobial Evaluation of a New Series of N-Sulfonamide 2-Pyridones as Dual Inhibitors of DHPS and DHFR Enzymes, ACS Omega, 2020, vol. 5, Issue 18, pp. 10401-10414.

Wrobel et al. Trimethoprim and other nonclassical antifolates an excellent template for searching modifications of dihydrofolate reductase enzyme inhibitors, The Journal of Antibiotics, 2019, vol. 73, pp. 5-27.

Blaney et al. Structure-activity relationships of dihydrofolated reductase inhibitors, Chemical Reviews, 1984, vol. 84, pp. 333-407.

Trott et al. AutoDock Vina: Improving the speed and accuracy of docking with a new scoring function, efficient optimization, and multithreading, Journal of Computational Chemistry, 2009, vol. 31, Issue 2, pp. 455-461.

Kreitler et al. The structural basis of N-acyl-α-amino-β-lactone formation catalyzed by a nonribosomal peptide synthetase, Nature Communications, 2019, vol. 10, Article No. 3432.

Bailey et al. Crystal Structure of Siderophore Binding Protein BauB Bound to an Unusual 2:1 Complex Between Acinetobactin and Ferric Iron, Biochemistry, 2018, vol. 57, Issue 48, pp. 6653-6661.

Yao et al. Design Aspects of Metal-Free Nitrogen-Based Catalysts and Their Influence on the Yield in the Henry Reaction, Synthesis, 2014, vol. 46, Issue 13, pp. 1793-1801.

Li et al. Enantioselective Nitroaldol Reaction of α-Ketoesters Catalyzed by Cinchona Alkaloids, Journal of the American Chemical Society, 2005, vol. 128, Issue 3, pp. 732-733.

Perron et al. A Method for the Selective Protection of Aromatic Amines in the Presence of Aliphatic Amines, 2009, Synthesis, v. 2009, No. 2, pp. 283-289.

Georg et al. Metal directed stereoselective synthesis of 3-(1'-hydroxyethyl)-2-azetidinones from ethyl 3-hydroxybutyrate, Tetrahedron Letters, 1990, vol. 31, Issue 23, pp. 3267-3270.

Hodgson, The Sandmeyer reaction, Chemical Reviews, 1947, vol. 40, Issue 2, pp. 251-277.

Johnson et al. The Original Michaelis Constant: Translation of the 1913 Michaelis-Menten Paper, Biochemistry, 2011, vol. 50, Issue 39, pp. 8264-8269.

\* cited by examiner

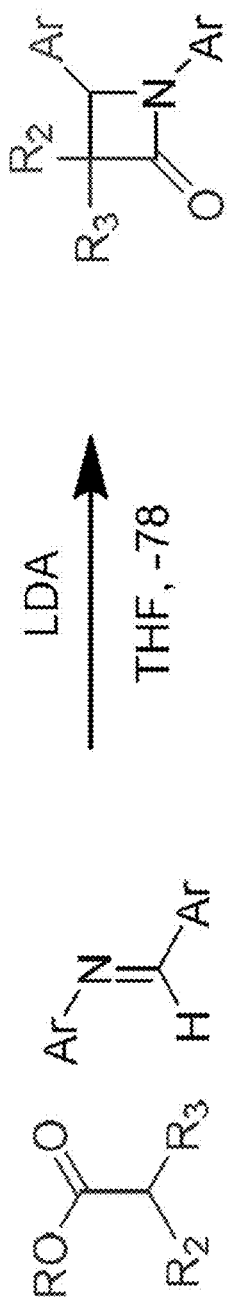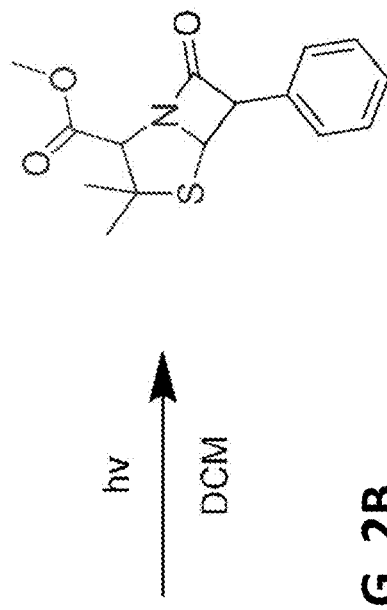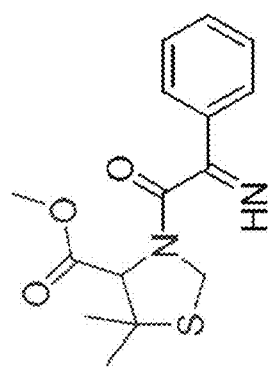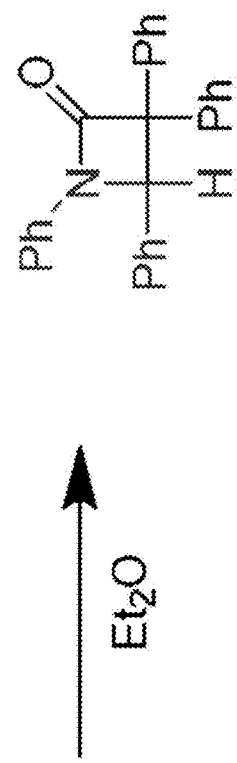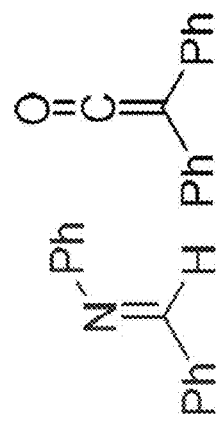
FIG. 2A
FIG. 2B
FIG. 2C

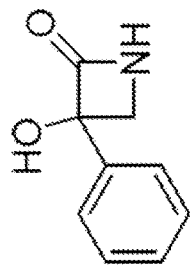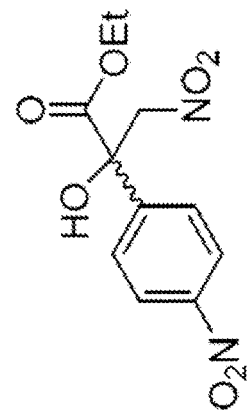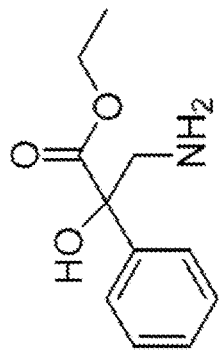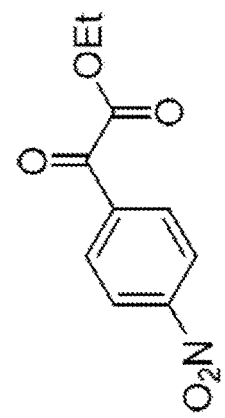
FIG. 10A
FIG. 10B

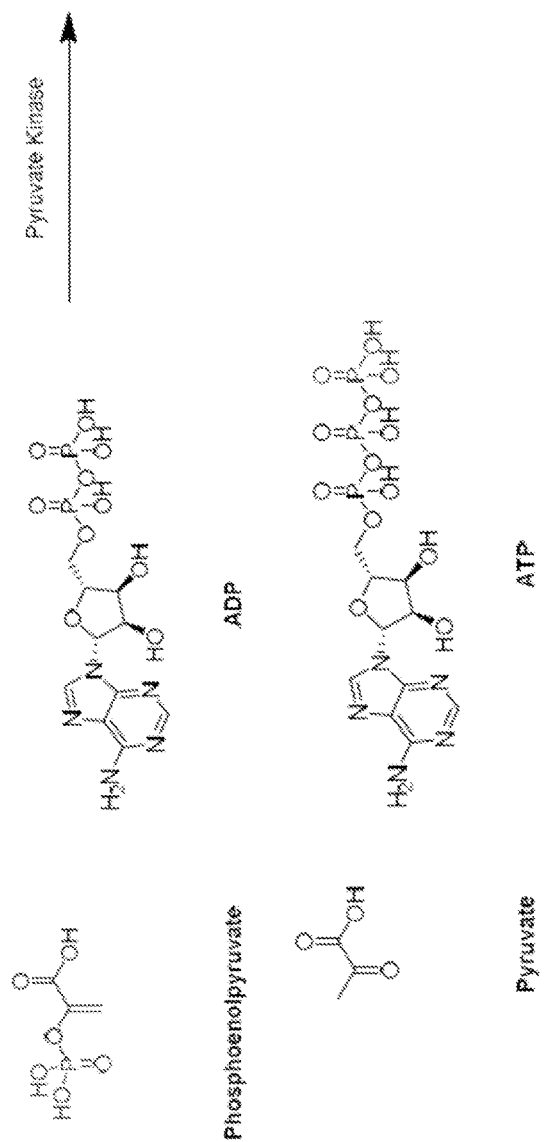
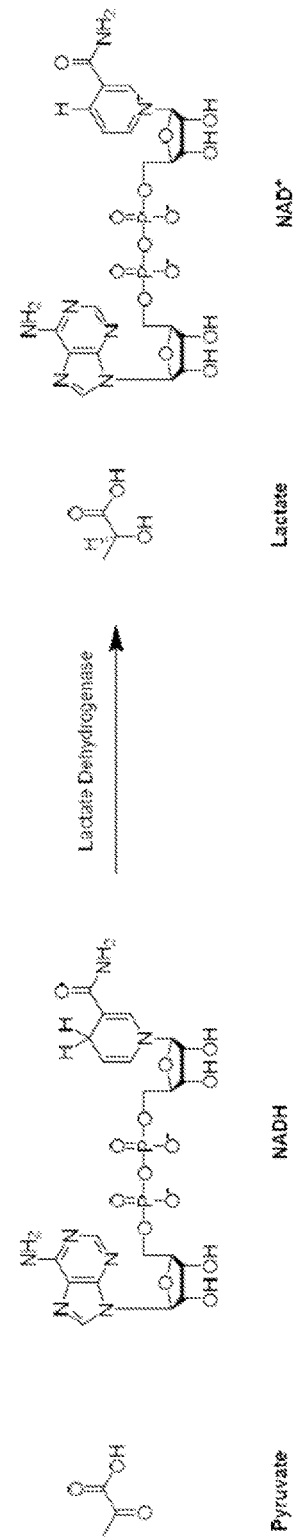
FIG. 20A
FIG. 20B 2,4-diaminopyrimidine-5-carbonitrile 2,4-diamino-6-(hydroxymethyl)pteridine 4.10

6M HCl
12 h
Quant.

4.12

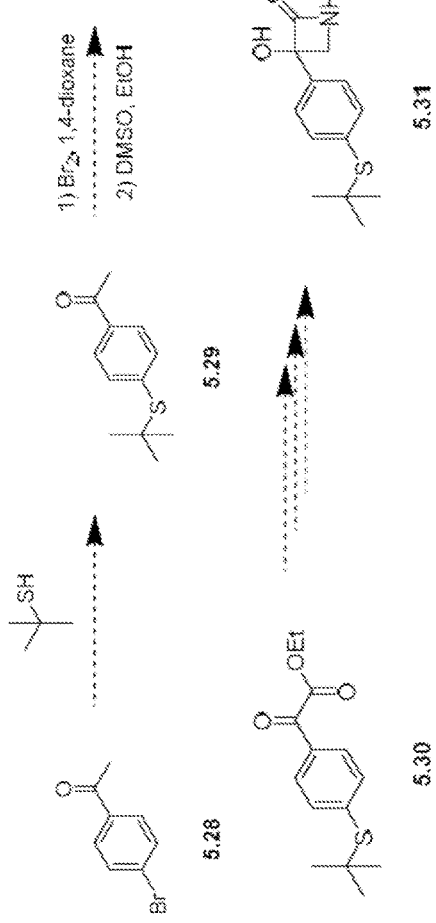
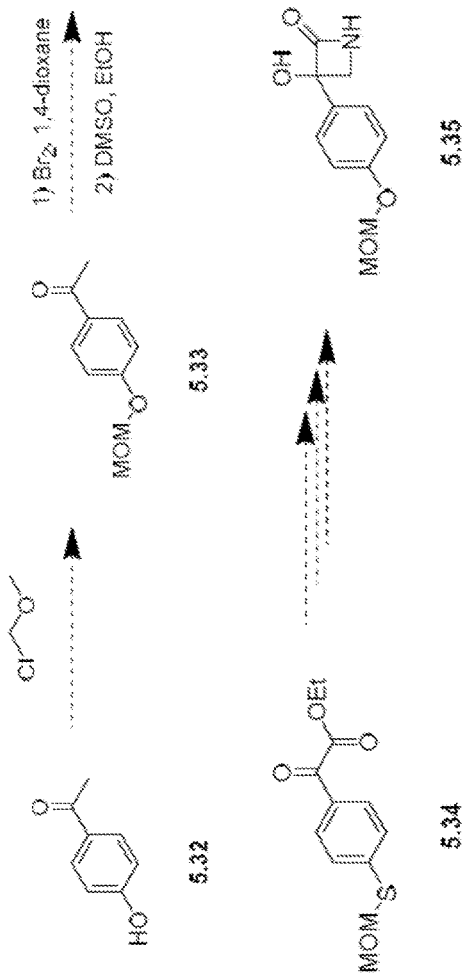
FIG. 45A
FIG. 45B

DIHYDROFOLATE SYNTHASE (DHFS) INHIBITING AGENTS AND METHODS OF MAKING AND USING SAME

CROSS-REFERENCE TO RELATED APPLICATIONS

This application claims priority from U.S. Provisional Application Ser. No. 63/328,949 filed on 8 Apr. 2022, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

Not applicable.

FIELD OF THE INVENTION

The present disclosure generally relates to compositions and methods for making and using antibiotics.

SUMMARY OF THE INVENTION

Among the various aspects of the present disclosure is the provision of compositions and methods for making and using dihydrofolate synthase (DHFS) inhibiting agents (or prodrugs thereof).

In an aspect of the present disclosure, a composition comprising a dihydrofolate synthase (DHFS) inhibiting agent is provided. The DHFS inhibiting agent comprises: a 3-hydroxy-beta-lactam, a 3-hydroxy-beta-lactam scaffold, a 3-hydroxy-beta-lactam derivative, or a prodrug, a pharmaceutically acceptable salt, tautomer, stereoisomer, derivative, or substituted analog thereof.

In some embodiments, the DHFS inhibiting agent comprises

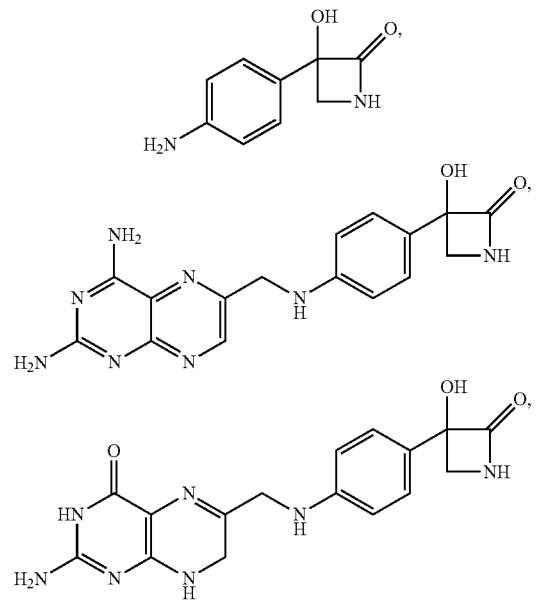

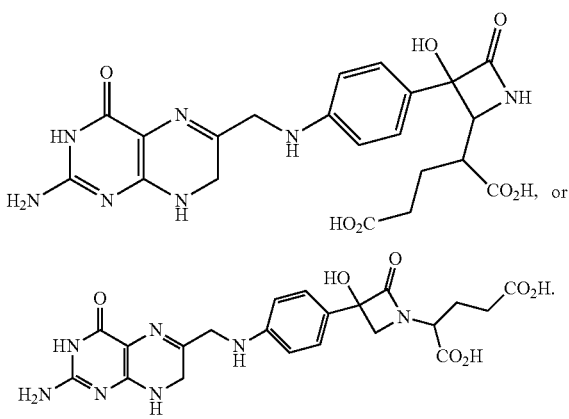

In some embodiments, the DHFS inhibiting agent is selected from:

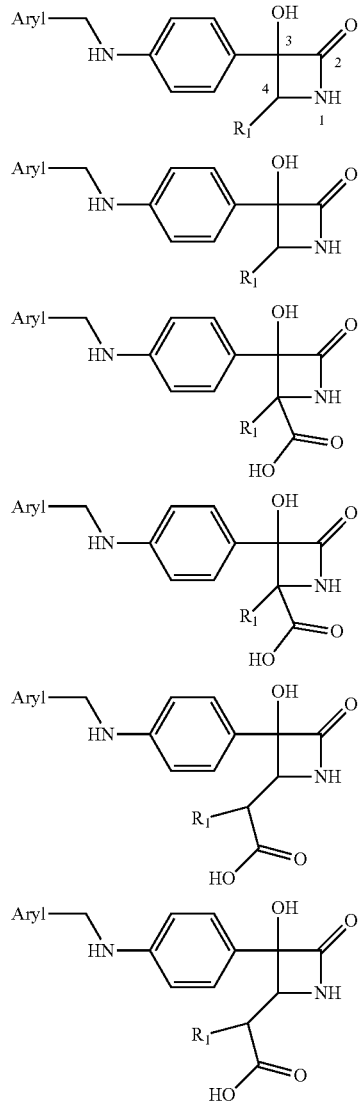

wherein $R_1$, is Me Et, Pr, or $(CH_2)_2$—COOH and Aryl is selected from

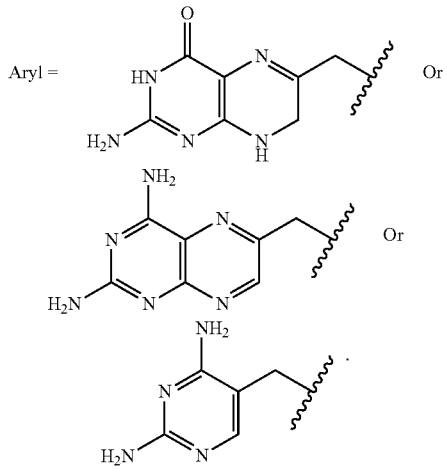

In some embodiments, the DHFS inhibiting agent comprises:

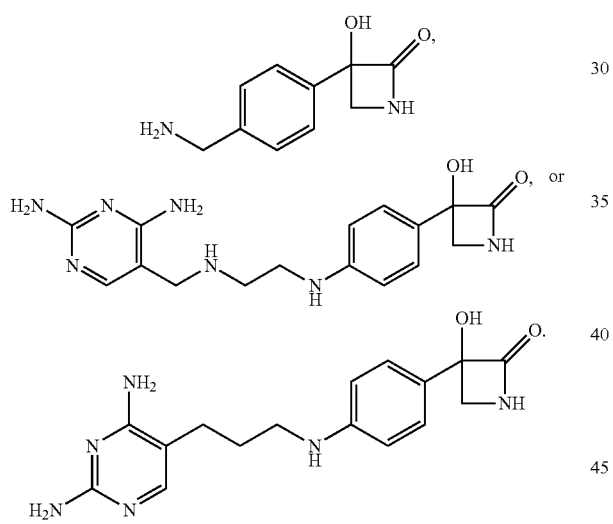

In some embodiments, the DHFS inhibiting agent further comprises a lipophilic side chain, pteridine, or aminopyrimidine pterin to enhance cell permeability. In some embodiments, the compositions further comprising an antifolate selected from a dihydropteroate synthase (DHPS) inhibitor or a dihydrofolate reductase (DHFR) inhibitor. In some embodiments, the antifolate is trimethoprim or sulfamethoxazole, the DHFS inhibiting agent mimics a tetrahedral intermediate of DHFS, and/or the DHFS inhibiting agent has an apparent IC50 of less than about 2 µM.

In another aspect of the present disclosure, a method of inhibiting dihydrofolate synthetase (DHFS) in a subject is provided. The method comprises administering a DHFS inhibiting agent comprising: a 3-hydroxy-beta-lactam, a 3-hydroxy-beta-lactam scaffold, a 3-hydroxy-beta-lactam derivative, or a prodrug, a pharmaceutically acceptable salt, tautomer, stereoisomer, derivative, or substituted analog thereof.

In some embodiments, the DHFS inhibiting agent comprises:

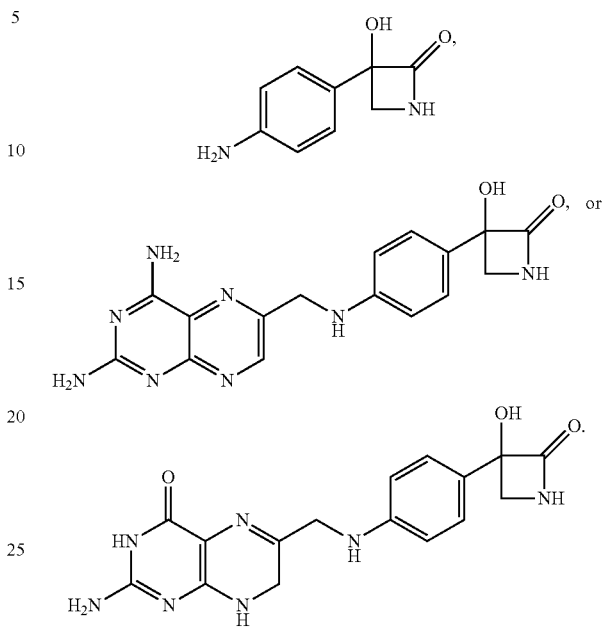

In some embodiments, the DHFS inhibiting agent is selected from:

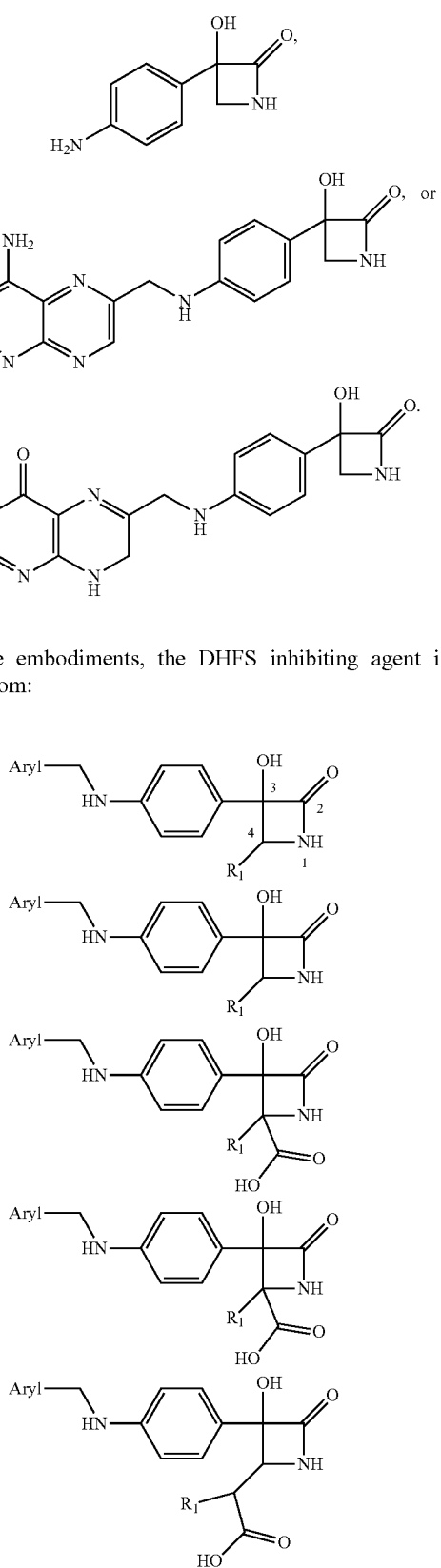

-continued

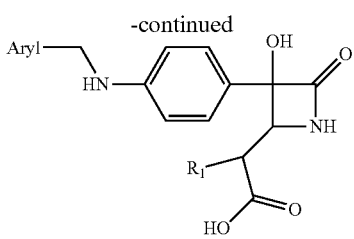

wherein R₁ is Me, Et, Pr, or (CH₂)₂—COOH and Aryl is selected from

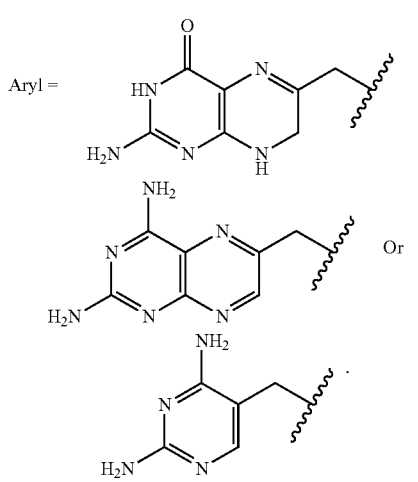

In some embodiments, the DHFS inhibiting agent comprises:

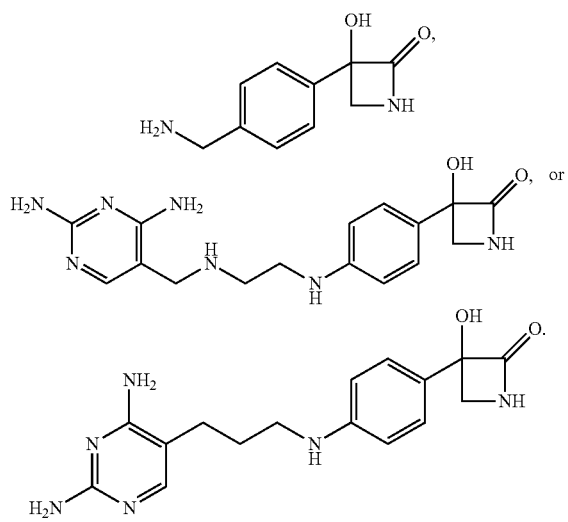

In some embodiments, the subject has a bacterial infection or an antibiotic-resistant bacterial infection. In some embodiments, the method further comprises administering an antifolate selected from a dihydropteroate synthase (DHPS) inhibitor or a dihydrofolate reductase (DHFR) inhibitor. In some embodiments, the antifolate is trimethoprim or sulfamethoxazole.

In yet another aspect of the present disclosure, a method of making a compound comprising a 3-hydroxy-beta-lactam (3-HβL) is provided. The method comprises: adding a nitromethane group to a p-nitro-aniline derived α-keto-ester using a Henry reaction, and using Grignard mediated-ring closing to yield a compound comprising an unprotected 3-HβL.

In some embodiments, the method further comprises providing acid to prevent reverse-Henry elimination of the nitromethane group, or providing buffered Boc protection conditions to selectively protect an aryl-nitrogen. In some embodiments, the compound comprising an unprotected 3-HβL is

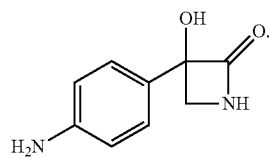

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 2A-FIG. 2F is an exemplary embodiment showing classic methods of β-lactam synthesis in accordance with the present disclosure. FIG. 2A is a schematic showing enolate-imine condensation. FIG. 2B is a schematic showing carbene C-H insertion. FIG. 2C is a schematic showing imine-ketene cycloaddition. FIG. 2D is a schematic showing Mitsunobu cyclization. FIG. 2E is a schematic showing photocyclization of α-keto-amides. FIG. 2F is a schematic showing photocyclization by Wherli.

FIG. 5A is a schematic showing successful synthetic efforts to achieve a methyl group at the para position of the aryl ring. FIG. 5B is a schematic showing unsuccessful bromination of the p-methyl group prior to photocyclization. FIG. 5C is a schematic showing unsuccessful bromination of the p-methyl group post-photocyclization.

FIG. 10A-FIG. 10B is an exemplary embodiment showing inspiration for the Henry reaction route towards a 3-HβL in accordance with the present disclosure. FIG. 10A is a schematic showing Grignard mediated ring closing of an unprotected 3-HβL. FIG. 10B is a schematic showing catalysis of the Henry reaction using a p-nitro-aniline derived α-keto-ester.

FIG. 20A-FIG. 20B is an exemplary embodiment showing PK/LDH system to detect ADP production in accordance with the present disclosure. FIG. 20A is a schematic showing pyruvate kinase transfers a phosphate group from PEP to ADP to form ATP and pyruvate. FIG. 20B is a schematic showing lactate dehydrogenase reduces pyruvate to lactate using NADH as the hydride source.

FIG. 21A is a schematic showing the three-enzyme sequence of catalysis. FIG. 21B is a graph showing the steady-state rate determination for DHPS activity by continuous measurement of optical absorbance at 340 nm (NADPH consumption). FIG. 21C is a graph showing the LCMS detection of 7,8-DHP (m/z=315 for expected [M+H]+ molecules ion) by DHPS.

FIG. 22A is a graph showing the inhibition of DHPS by sulfamethoxazole. Apparent IC50=558 μM±200 μM. FIG. 22B is a graph showing effects of variable concentrations of 3-HβL BVD-3-7 on DHPS activity. Apparent IC50=4.39 mM±5.203 mM.

FIG. 23A is a schematic showing three enzyme sequence for catalysis and detection of a 3-HβL-pterin adduct. FIG. 23B is a graph showing steady-state rates of DHPS for BVD-3-7 (slower) and PABA (faster) as substrates. FIG. 23C is a graph showing LC-MS detection of the 3-(para-$NH_2$-phenyl)-3-HβL-pterin (m/z=356 for expected [M+H]+ molecular ion) produced by DHPS.

FIG. 24A is a schematic showing the DHFS catalyzed polyglutamylation of THFA. FIG. 24B is a graph showing the PK/LDH coupled enzyme assay steady-state rate determination of DHFS activity by continuous measurement of optical absorbance at 340 nm.

FIG. 25A is a schematic showing ATP-dependent glutamylation followed by air oxidation of THFA. FIG. 25B is a graph showing LCMS results showing production of Glu-THFA (m/z=573 for expected [M+H]+ molecular ion) when DHFS is present vs the no enzyme control.

FIG. 27A is a molecular model showing a zoom in on the active site showing the pterin binding pocket anchoring the PABA moiety towards the ADP. FIG. 27B is a schematic showing the predicted active site interactions between 7,8-dihydropteroate phosphate and the surrounding residues. The magnesium ions function to position and activate the phosphate and the ADP.

FIG. 28A is a schematic showing structures docked using DHFS. FIG. 28B-FIG. 28G include molecular models showing (B) 7,8-DHP in yellow and Compound 1 in teal (C) 7,8-DHP in yellow and Compound 2 in Purple (D) 7,8-DHP in yellow and Compound 2 in an out-pose (E) 7,8-DHP in yellow and Compound 6 in blue (F) 7,8-DHP in yellow and Compound 7 in orange (G) 7,8-DHP in yellow and Compound 8 in green.

FIG. 29A is a structure showing the starting material to access the pterin mimic from methotrexate. FIG. 29B is a structure showing the starting material to access the pterin mimic from trimethoprim.

FIG. 33A is a structure showing the pterin mimic-3-(para-NH$_2$-phenyl)-3-HβL 4.10, using the pterin mimic from methotrexate. FIG. 33B is a structure showing the pterin mimic-3-(para-NH$_2$-phenyl)-3-HβL 4.6, using the pterin mimic from trimethoprim. FIG. 33C is a structure showing the pterin-3-(para-NH$_2$-phenyl)-3-HβL 4.11 synthesized chemoenzymatically.

FIG. 34A includes a graph showing inhibition of DHFS by the compound 4.10 derived from methotrexate with an apparent IC50 of 1.8 μM±0.7 μM. FIG. 34B includes a graph showing inhibition of DHFS by the compound 4.6 derived from trimethoprim with an apparent IC50 of 960 μM±1380 μM.

FIG. 35A is a scheme for production and subsequent use of a 3-HβL-pterin adduct using the biologically identical pterin in the correct oxidation state. FIG. 35B includes a graph showing the reduction of DHFS rate with the increase of the pterin-3-(para-NH$_2$-phenyl)-3-HβL 4.11 concentration.

FIG. 37A includes a graph showing inhibition of DHFS by the compound 4.10 with an apparent IC50 of 2.6 μM±1.1 μM. FIG. 37B includes a graph showing inhibition of DHFS by the compound 4.12 with an apparent IC50 of 71.5 μM±62.1 μM.

FIG. 38A includes a graph showing detection of (L)-Gludihydrofolic acid after DHFS action in a well with varying concentrations of inhibitor 4.10. FIG. 38B includes a graph showing detection of (L)-Glu-dihydrofolic acid after DHFS action in a well with varying concentrations of inhibitor 4.12.

FIG. 40A-FIG. 40C includes protein mass spectrometry for (A) 0 μM (B) 40 μM and (C) μM of 3-HβL 4.10.

FIG. 44A is a schematic showing the introduction of a methylene spacer between the phenol ring and the nitrogen linker. FIG. 44B is a schematic showing linker expansion by 3rd compound dual linkage. FIG. 44C is a schematic showing linker expansion by metathesis.

FIG. 45A-FIG. 45B is an exemplary embodiment showing proposed synthesis to introduce new heteroatom linkers in accordance with the present disclosure. FIG. 45A is a schematic showing protected benzenethiol introduction to become the eventual linker between a pterin and a 3-HβL. FIG. 45B is a schematic showing protected phenol introduction to become the eventual linker between a pterin and a 3-HβL.

FIG. 46A is a schematic showing the reaction catalyzed by DDL. FIG. 46B is a schematic showing the proposed 3-HβL mimic of D-alanine. FIG. 46C is a schematic showing that an N-OBn protecting group can be successfully removed from a β-lactam. FIG. 46D is a schematic showing proposed Sharpless asymmetric aminohydroxylation to achieve stereoselective synthesis of a proposed DDL inhibitor.

FIG. 47A is a schematic showing aminopeptidase cleavage of L-Thr from β-tabtoxin to reveal the active form tabtoxinine-β-lactam. FIG. 47B is a schematic showing aminopeptidase cleavage of a potential prodrug formulation of a DDL inhibitor containing a 3-HβL.

DETAILED DESCRIPTION OF THE INVENTION

Figure 1:
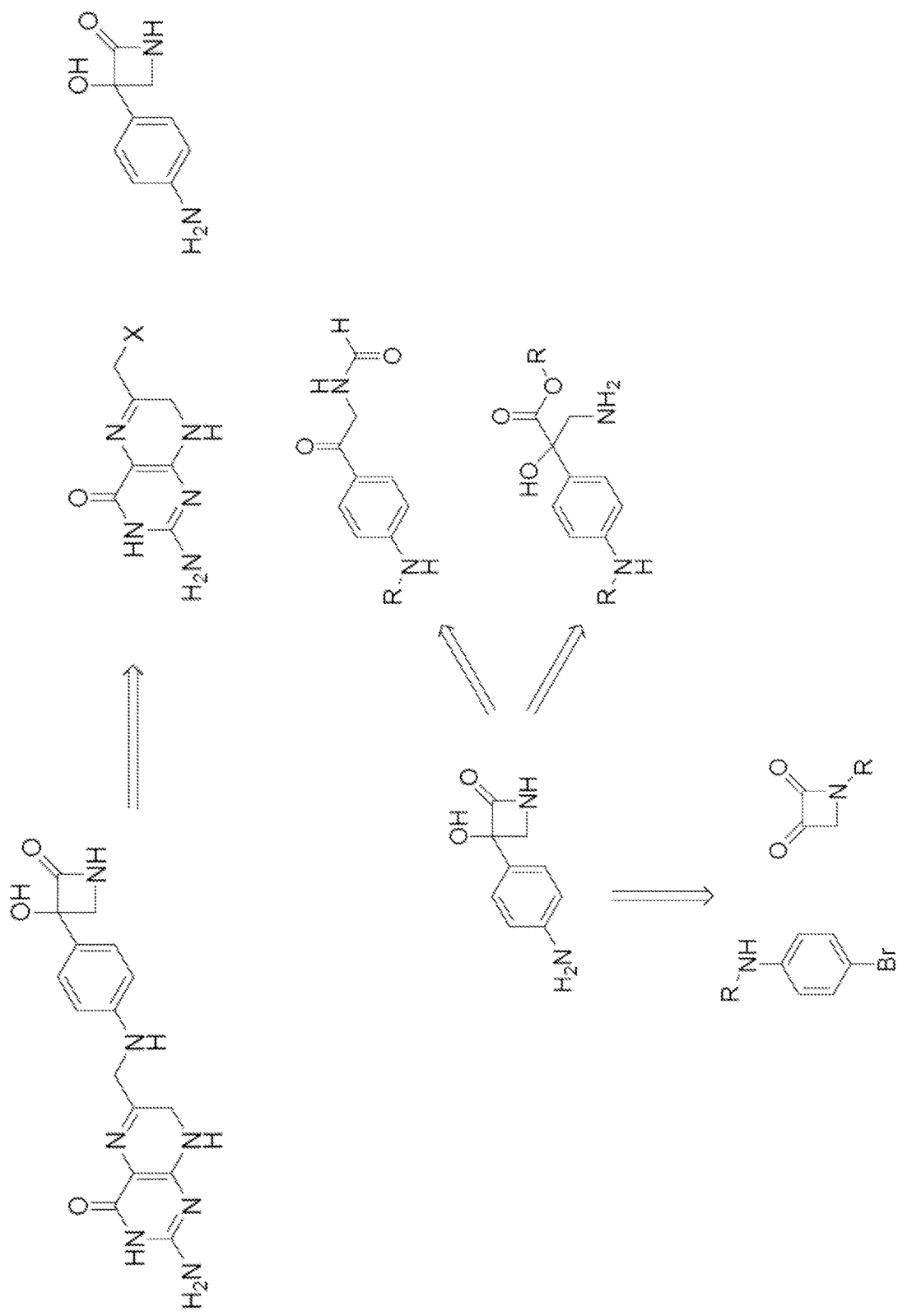
FIG. 1 is a schematic showing retrosynthesis breakdown into the three methods of 3-HβL formation that were attempted in accordance with the present disclosure.

The present disclosure is based, at least in part, on the discovery of dihydrofolate synthase (DHFS) inhibitors based on a novel 3-hydroxy-beta-lactam (3-HBL) pharmacophore and their use for antifolate or antibacterial therapies. As shown herein, the unique nature of the 3-hydroxy-beta-lactam is harnessed to replicate the tetrahedral intermediate of DHFS, achieving tight binding and single digit micromolar IC50 measurements against DHFS enzymatic action.

The folate biosynthetic pathway is ubiquitous in bacterial pathogens and absent in humans. While there are many potential targets in the folate biosynthetic/utilization pathways, only three targets are engaged by current antifolate drugs: dihydropteroate synthase (DHPS), dihydrofolate reductase (DHFR), and thymidylate synthase. Sulfonamide inhibitors of DHPS have been used for more than 80 years to block de novo folate biosynthesis. Resistance to sulfonamides is well established and widely disseminated. Resistance to DHFR inhibitors is also widespread. The novel DHFS inhibitors described herein have the potential to expand the use of antibiotics in the clinic as well as circumvent known mechanisms of resistance against clinically used antibiotics.

Combinations of DHPS and DHFR inhibitors are synergistic. DHPS inhibitors such as sulfamethoxazole (SMX) block the biosynthesis of dihydrofolate (DHF); whereas DHFR inhibitors such as trimethoprim (TMP) block reduction of DHF to tetrahydrofolate (THF). Synergy between DHFR inhibitors and other types of antifolates is expected exist and may offer a way forward to extend the clinical lifespan of antifolate combination therapies and outpace resistance. As such, the novel DHFS inhibitors described herein may be used synergistically in combination with DHFR inhibitors, DHPS inhibitors, or other antifolate therapies.

The 3-HBL inhibitors of DHFS described herein offer several potential advantages over other inhibitor approaches, including phosphinates. There are three unique points for derivatization on the 3-HBL ring (N1,C3,C4). The stereochemistry at C3 and C4 can be controlled to match the chirality of the DHFS transition state (TS) to provide fundamental insight into the catalytic mechanism of DHFS and inform inhibitor optimization. 3-HBLs, as opposed to phosphinates, are neutral and therefore are not prone to cytoplasmic exclusion due to unfavorable electrostatics. Polarity of 3-HBLs is a better match for the natural DHFS TS (late TS resembling the tetrahedral intermediate for nucleophilic acyl substitution based on the Hammett postulate). The proposed TS includes an oxyanion (amide carbonyl), nitrogen cation (amide nitrogen), and phosphate (phosphorylated C3-hydroxyl). Phosphinates only mimic the oxyanion and phosphate groups.

The 3-HBL DHFS inhibitors described herein also have several advantages over sulfonamides. Sulfonamides are reversible inhibitors of DHPS. This leaves sulfonamides vulnerable to competition from an increase in metabolic flux through the folate pathway. 3-HBLs are predicted to be potent irreversible TS inhibitors of DHFS that may alleviate resistance pressure on DHFR and lower doses in combination therapies. Sulfonamide resistance is widespread. DHFS offers fertile ground, free of established resistance.

Described herein is a rational and targeted drug design that did not arise from large screening efforts or target searches. A novel pharmacophore was successfully adapted to a system with known clinical relevance, despite the untested nature of the pharmacophore in new systems and the relative lack of exploration around the target enzyme, dihydrofolate synthetase (DHFS), compared to its neighbors in the folate biosynthetic pathway. A new inhibitor of DHFS was discovered using a novel pharmacophore (the 3-HβL), paving the way for exploration of methods of inhibiting DHFS and exploration around other possible ATP-dependent carboxylate-amine ligase enzyme targets.

Figure 11:
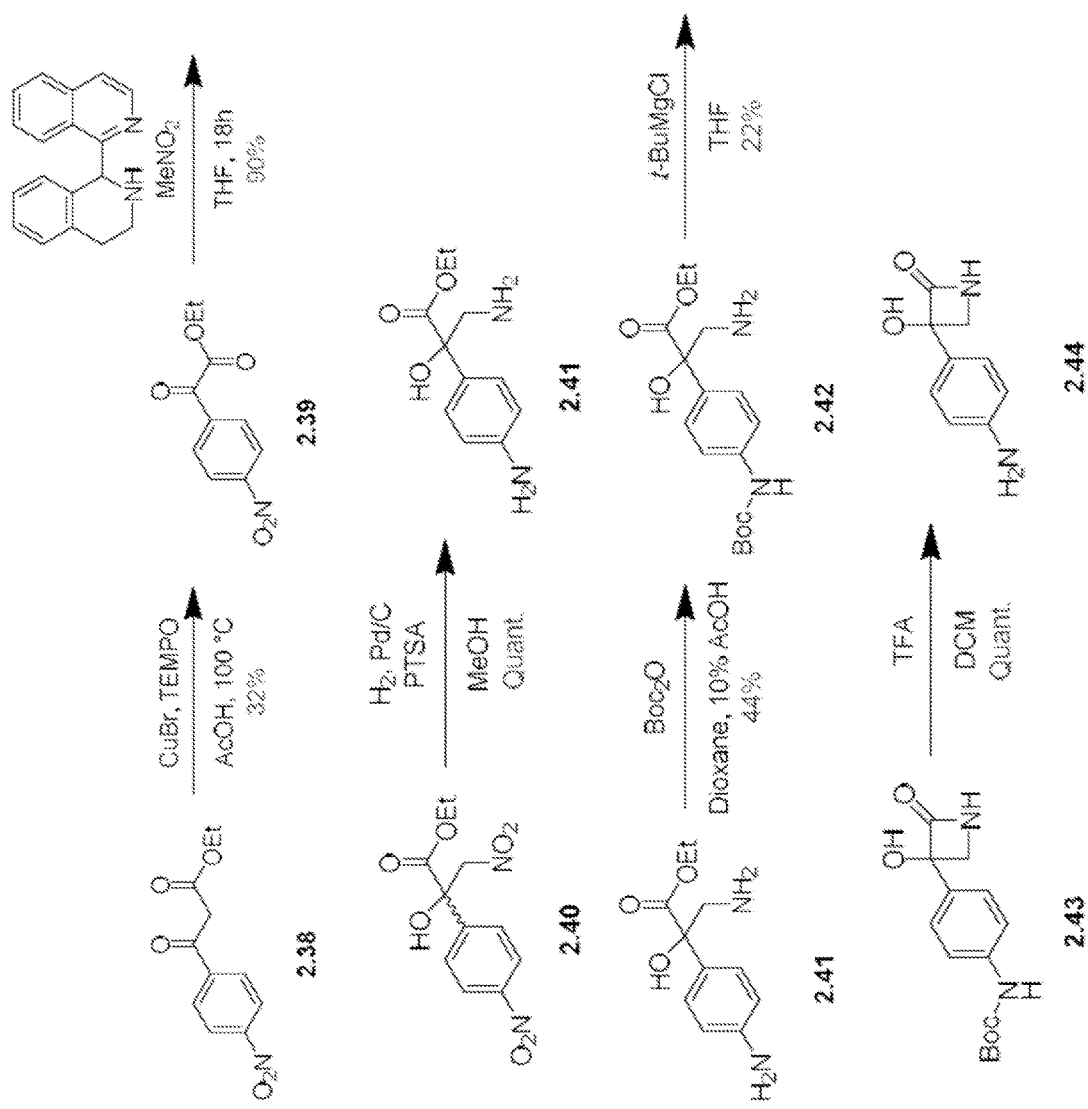
FIG. 11 is a schematic showing successful synthesis of an unsubstituted and unprotected 3-HβL utilizing a Henry reaction and a Grignard mediated ring closing in accordance with the present disclosure.

Established herein is a synthetic methodology for creating suitable 3-HβL compounds for testing against DHFS (see e.g., Example 1). Many methods of β-lactam synthesis were explored and three synthetic routes were attempted. The first route used a Norrish II photocyclization of complete the 3-HβL but was unsuccessful in furnishing the aniline linker desired. The second route used a Grignard-mediated ring closing step to complete the 3-HβL but was unsuccessful in furnishing the 3-HβL without a protecting group on 1 N. The third route utilized a Henry reaction to set the 3-hydroxy group and a Grignard-mediated ring closing to complete the 3-HβL and was successful in furnishing the target 3-(para-NH$_2$-phenyl)-3-HβL 2.44 (see e.g., FIG. 11).

Also established herein are biochemical assays to test whether the 3-HβL 2.44 is a suitable pharmacophore to inhibit DHFS (see e.g., Example 2). DHFS' neighboring enzymes in the folate biosynthesis pathway dihydropteroate synthetase (DHPS) and dihydrofolate reductase (DHFR), along with 7,8-dihydro-6-hydroxymethylpterin-pyrophosphokinase (HPPK), which catalyzes the production of the substrate of DHPS, were investigated. Challenges around the oxidation state of the pterin and pteridine rings as substrates for folate biosynthetic enzymes were explored and overcome to establish assays capable of measuring steady state kinetics for both DHPS and DHFS (see e.g., FIG. 21B and FIG. 24B). Much like its sulfa drug cousins, 3-HβL 2.44 was discovered to be a substrate of DHPS, meaning DHPS can be used to chemoenzymatically assemble a 3-HβL-pterin adduct using the biological pterin ring system in its correct oxidation state.

Figure 37B:
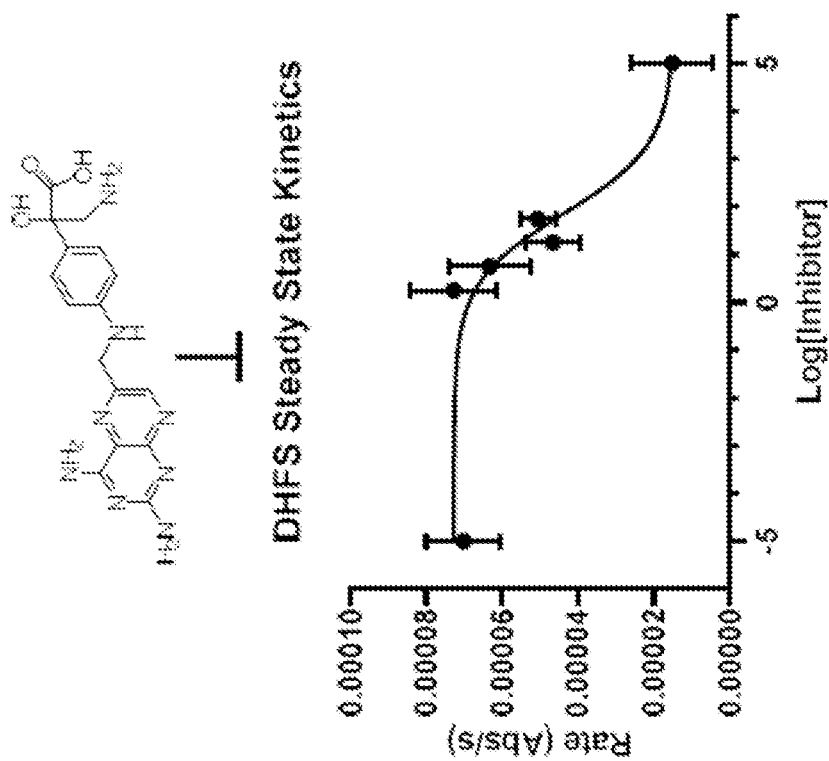
FIG. 37A-FIG. 37B is an exemplary embodiment showing IC50 curves for DHFS inhibition by a 3-HβL and its corresponding hydrolyzed product in accordance with the present disclosure.
Figure 37A:
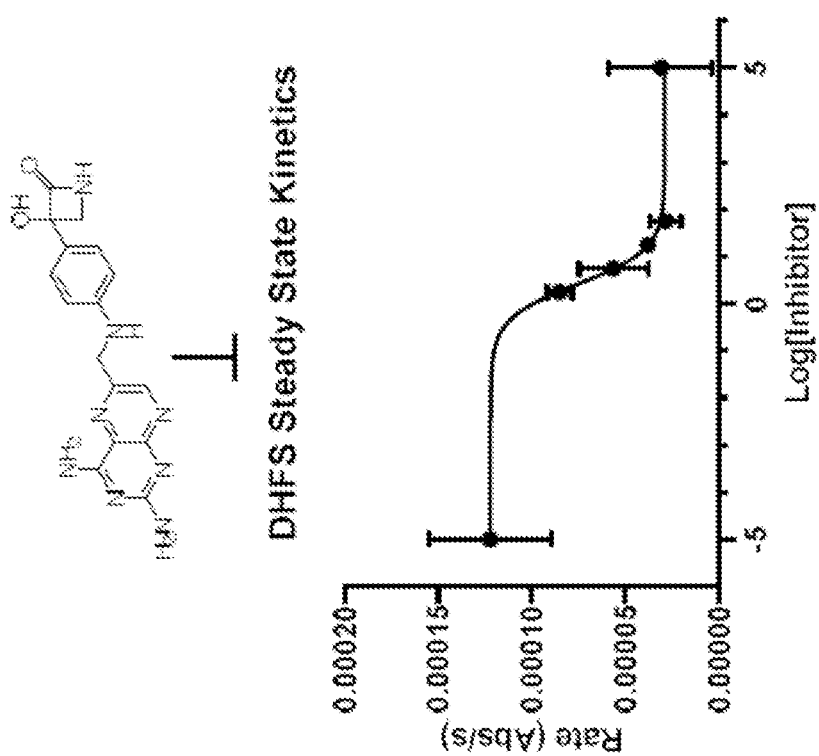
Figures 38A, 38B:
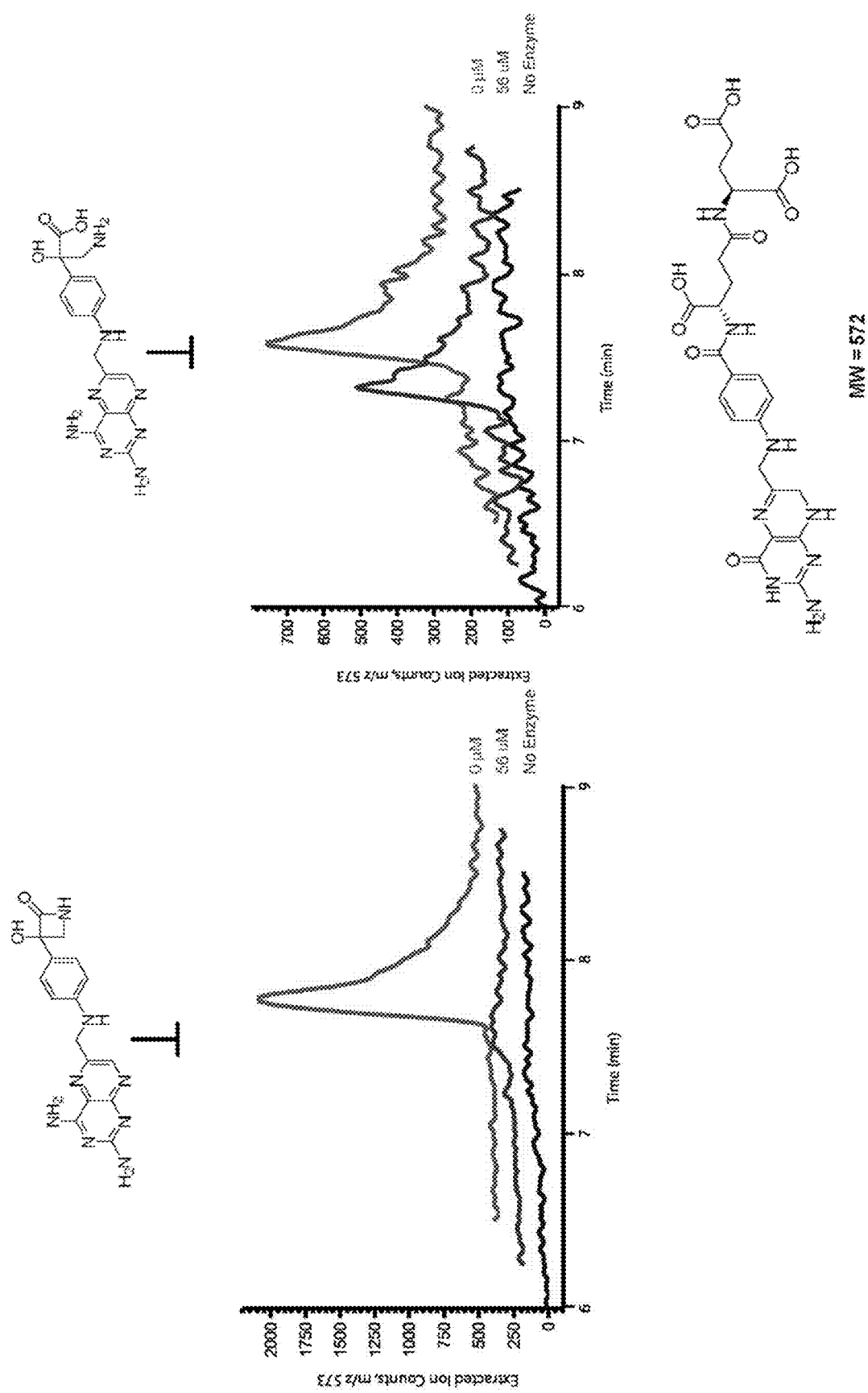
FIG. 38A-FIG. 38B is an exemplary embodiment showing LCMS signatures from DHFS steady state kinetics assays in accordance with the present disclosure.

3-HβL pteridine compounds capable of inhibiting DHFS enzymatic action were thus assembled (see e.g., Example 3). Two new inhibitors of DHFS were discovered, 4.10 and 4.11, using either the pteridine from the clinically used drug methotrexate or the pterin from the natural biosynthesis system respectively along with a 3-HβL warhead. 4.10 in particular was discovered to be a tight binding inhibitor with low micromolar IC50 values that is capable of 100% DHFS inhibition in double digit micromolar concentrations (see e.g., FIG. 37A and FIG. 38A). A preference for pterin-mimic ring systems was established, and modeling showed benefit for a pterin-3-HβL linker of sufficient size. No whole cell activity was detected for any 3-HβL tested against *E. coli* or *S. aureus*, potentially due to lack of cell permeability.

Dihydrofolate Synthase (DHFS) Inhibiting Agent

One aspect of the present disclosure provides for targeting or inhibiting dihydrofolate synthase (DHFS). The present disclosure provides methods of treating or preventing infection or antibiotic resistant infection based on the discovery that inhibitors of dihydrofolate synthase (DHFS) have potential for novel anti-folate therapies.

Inhibition of agents as described herein can be determined by standard pharmaceutical procedures in assays or cell cultures for determining the IC$_{50}$. The half maximal inhibitory concentration (IC$_{50}$) is a measure of the potency of a substance in inhibiting a specific biological or biochemical function. The IC$_{50}$ is a quantitative measure that indicates how much of a particular inhibitory substance (e.g., pharmaceutical agent or drug) is needed to inhibit, in vitro, a given biological process or biological component by 50%. The biological component could be an enzyme, cell, cell receptor, or microorganism, for example. IC$_{50}$ values are typically expressed as molar concentration. IC$_{50}$ is generally used as a measure of antagonist drug potency in pharmacological research. IC$_{50}$ is comparable to other measures of potency, such as EC$_{50}$ for excitatory drugs. EC$_{50}$ represents the dose or plasma concentration required for obtaining 50% of a maximum effect in vivo. IC$_{50}$ can be determined with functional assays or with competition binding assays.

Examples of DHFS agents are described herein. DHFS inhibiting agents can be or comprise a 3-hydroxy-beta-lactam, a 3-hydroxy-beta-lactam scaffold, a 3-hydroxy-beta-lactam derivative, a prodrug, a pharmaceutically acceptable salt, tautomer, stereoisomer, derivative, or substituted analog thereof.

In some embodiments, the DHFS inhibiting agent can be a prodrug inhibitor of DHFS. For example, a prodrug inhibitor of DHFS may allow for the formation of 7,8- dihydropteroate-3-HBL DHFS inhibitors via intracellular biosynthetic conversion by DHPS (e.g., acts as a substrate for DHPS). A prodrug inhibitor of DHFS may be a 3-(p-amino-phenyl)-3-HBL, wherein recombinant HPPK/DHPS enzymes, for example, are used to convert the 3-(p-amino-phenyl)-3-HBLs the dihydropteroate adducts. As another example, a prodrug inhibitor of DHFS may include:

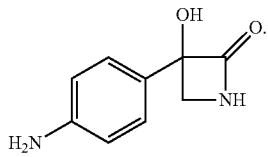

In some embodiments, the DHFS inhibiting agent is a direct inhibitor of DHFS. For example, the DHFS inhibiting agent may be a fully synthetic 3-aryl-3-HBL, wherein the aryl group mimics 7,8-dihydropteroate. For example, the DHFS inhibiting agent may include:

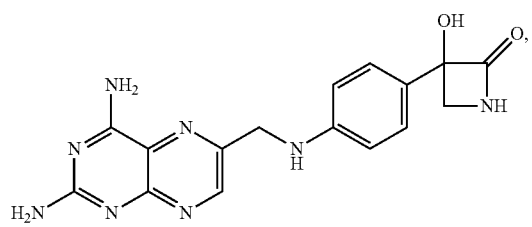

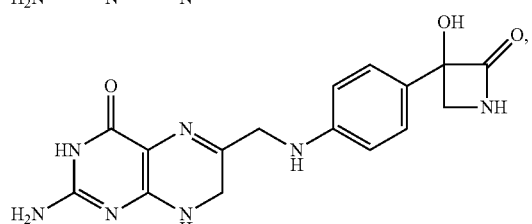

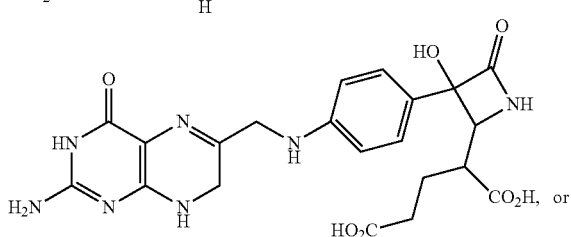

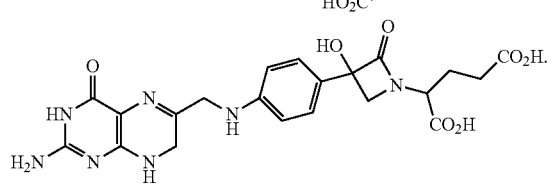

As another example, the DHFS inhibiting agent may be:

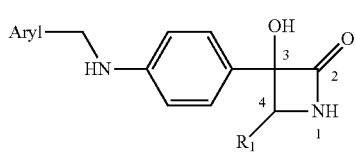

-continued

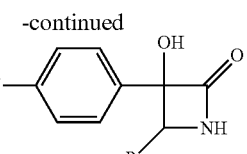

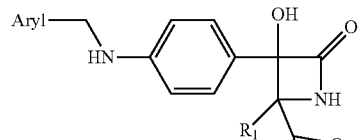

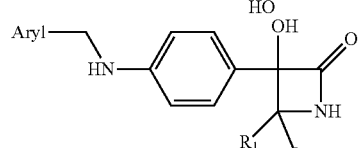

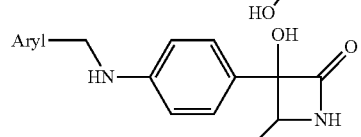

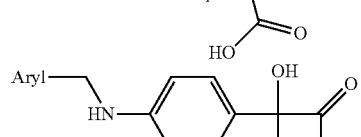

wherein $R_1$ is Me, Et, Pr, or $(CH_2)_2$—COOH and the aryl is selected from

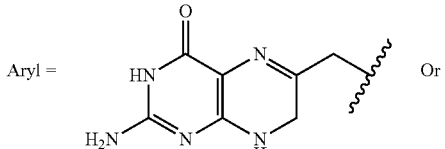

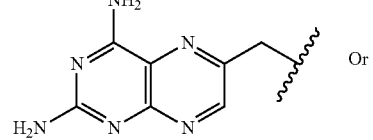

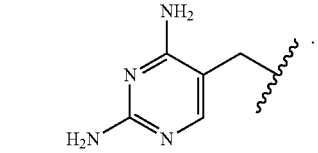

The DHFS inhibiting agent can comprise R groups that can be, or can be optionally substituted with, one or more groups independently selected from the group consisting of hydroxyl; $C_{1-10}$alkyl hydroxyl; amine; $C_{1-10}$carboxyl; straight chain or branched $C_{1-10}$alkyl, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; and aryl comprising a phenyl; heteroaryl containing from 1 to 4 N, O, or S atoms; unsubstituted phenyl ring; substituted phenyl ring; unsubstituted heterocyclyl; and substituted heterocyclyl, wherein the unsubstituted phenyl ring or substituted phenyl ring can be optionally substituted with one or more groups independently selected from the group consisting of hydroxyl; $C_{1-10}$alkyl hydroxyl; amine; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; straight chain or branched $C_{1-10}$alkyl amine; heterocyclyl; heterocyclic amine; aryl comprising a phenyl; and heteroaryl containing from 1 to 4 N, O, or S atoms; and the unsubstituted heterocyclyl or substituted heterocyclyl can be optionally substituted with one or more groups independently selected from the group consisting of hydroxyl; $C_{1-10}$alkyl hydroxyl; amine; $C_{1-10}$carboxyl; straight chain or branched $C_{1-10}$alkyl, optionally containing unsaturation; straight chain or branched $C_{1-10}$alkyl amine, optionally containing unsaturation; a $C_{2-10}$cycloalkyl optionally containing unsaturation or one oxygen or nitrogen atom; heterocyclyl; straight chain or branched $C_{1-10}$alkyl amine; heterocyclic amine; and aryl comprising a phenyl; and heteroaryl containing from to 4 N, O, or S atoms. Any of the above can be further optionally substituted.

The term "imine" or "imino", as used herein, unless otherwise indicated, can include a functional group or chemical compound containing a carbon-nitrogen double bond. The expression "imino compound", as used herein, unless otherwise indicated, refers to a compound that includes an "imine" or an "imino" group as defined herein. The "imine" or "imino" group can be optionally substituted.

The term "hydroxyl", as used herein, unless otherwise indicated, can include —OH. The "hydroxyl" can be optionally substituted.

The terms "halogen" and "halo", as used herein, unless otherwise indicated, include a chlorine, chloro, Cl; fluorine, fluoro, F; bromine, bromo, Br; or iodine, iodo, or I.

The term "acetamide", as used herein, is an organic compound with the formula $CH_3CONH_2$. The "acetamide" can be optionally substituted.

The term "aryl", as used herein, unless otherwise indicated, include a carbocyclic aromatic group. Examples of aryl groups include, but are not limited to, phenyl, benzyl, naphthyl, or anthracenyl. The "aryl" can be optionally substituted.

The terms "amine" and "amino", as used herein, unless otherwise indicated, include a functional group that contains a nitrogen atom with a lone pair of electrons and wherein one or more hydrogen atoms have been replaced by a substituent such as, but not limited to, an alkyl group or an aryl group. The "amine" or "amino" group can be optionally substituted.

The term "alkyl", as used herein, unless otherwise indicated, can include saturated monovalent hydrocarbon radicals having straight or branched moieties, such as but not limited to, methyl, ethyl, propyl, butyl, pentyl, hexyl, octyl groups, etc. Representative straight-chain lower alkyl groups include, but are not limited to, -methyl, -ethyl, -n-propyl, -n-butyl, -n-pentyl, -n-hexyl, -n-heptyl and -n-octyl; while branched lower alkyl groups include, but are not limited to, -isopropyl, -sec-butyl,-isobutyl, -tert-butyl, -isopentyl, 2-methylbutyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, unsaturated $C_{1-10}$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -pentynyl,-2-pentynyl, or 3-methyl-1 butynyl. An alkyl can be saturated, partially saturated, or unsaturated. The "alkyl" can be optionally substituted.

The term "carboxyl", as used herein, unless otherwise indicated, can include a functional group consisting of a carbon atom double bonded to an oxygen atom and single bonded to a hydroxyl group (—COOH). The "carboxyl" can be optionally substituted.

The term "carbonyl", as used herein, unless otherwise indicated, can include a functional group consisting of a carbon atom double-bonded to an oxygen atom (C=O). The "carbonyl" can be optionally substituted.

The term "alkenyl", as used herein, unless otherwise indicated, can include alkyl moieties having at least one carbon-carbon double bond wherein alkyl is as defined above and including E and Z isomers of said alkenyl moiety. An alkenyl can be partially saturated or unsaturated. The "alkenyl" can be optionally substituted.

The term "alkynyl", as used herein, unless otherwise indicated, can include alkyl moieties having at least one carbon-carbon triple bond wherein alkyl is as defined above. An alkynyl can be partially saturated or unsaturated. The "alkynyl" can be optionally substituted.

The term "acyl", as used herein, unless otherwise indicated, can include a functional group derived from an aliphatic carboxylic acid, by removal of the hydroxyl (—OH) group. The "acyl" can be optionally substituted.

The term "alkoxyl", as used herein, unless otherwise indicated, can include O-alkyl groups wherein alkyl is as defined above and O represents oxygen. Representative alkoxyl groups include, but are not limited to, —O-methyl, —O-ethyl, —O-n-propyl, —O-n-butyl, —O-n-pentyl, —O-n-hexyl, —O-n-heptyl, —O-n-octyl, —O-isopropyl, —O-sec-butyl, —O-isobutyl, —O-tert-butyl, —O-isopentyl, —O-2-methylbutyl, —O-2-methylpentyl, —O-3-methylpentyl, —O-2,2-dimethylbutyl, —O-2,3-dimethylbutyl, —O-2,2-dimethylpentyl, —O-2,3-dimethylpentyl, —O-3,3-dimethylpentyl, —O-2,3,4-trimethylpentyl, —O-3-methylhexyl, —O-2,2-dimethylhexyl, —O-2,4-dimethylhexyl, —O-2,5-dimethylhexyl, —O-3,5-dimethylhexyl, —O-2,4-dimethylpentyl, —O-2-methylheptyl, —O-3-methylheptyl, —O-vinyl, —O-allyl, —O-1-butenyl, —O-2-butenyl, —O-isobutylenyl, —O-1-pentenyl, —O-2-pentenyl, —O-3-methyl-1-butenyl, —O-2-methyl-2-butenyl, —O-2,3-dimethyl-2-butenyl, —O-1-hexyl, —O-2-hexyl, —O-3-hexyl, —O-acetylenyl, —O-propynyl, —O-1-butynyl, —O-2-butynyl, —O-1-pentynyl, —O-2-pentynyl and —O-3-methyl-1-butynyl, —O-cyclopropyl, —O-cyclobutyl, —O-cyclopentyl, —O-cyclohexyl, —O-cycloheptyl, —O-cyclooctyl, —O-cyclononyl and —O-cyclodecyl, —O—$CH_2$-cyclopropyl, —O—$CH_2$-cyclobutyl, —O—$CH_2$-cyclopentyl, —O—$CH_2$-cyclohexyl, —O—$CH_2$-cycloheptyl, —O—$CH_2$-cyclooctyl, —O—$CH_2$-cyclononyl, —O—$CH_2$-cyclodecyl, —O—$(CH_2)_2$-cyclopropyl, —O—$(CH_2)_2$-cyclobutyl, —O—$(CH_2)_2$-cyclopentyl, —O—$(CH_2)_2$-cyclohexyl, —O—$(CH_2)_2$-cycloheptyl, —O—$(CH_2)_2$-cyclooctyl, —O—$(CH_2)_2$-cyclononyl, or —O—$(CH_2)_2$-cyclodecyl. An alkoxyl can be saturated, partially saturated, or unsaturated. The "alkoxyl" can be optionally substituted.

The term "cycloalkyl", as used herein, unless otherwise indicated, can include an aromatic, a non-aromatic, saturated, partially saturated, or unsaturated, monocyclic or fused, spiro or unfused bicyclic or tricyclic hydrocarbon referred to herein containing a total of from 1 to 10 carbon atoms (e.g., 1 or 2 carbon atoms if there are other heteroatoms in the ring), preferably 3 to 8 ring carbon atoms. Examples of cycloalkyls include, but are not limited to, $C_{3-10}$ cycloalkyl groups include, but are not limited to, -cyclopropyl, -cyclobutyl, -cyclopentyl, -cyclopentadienyl,-cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. The term "cycloalkyl" also can include -lower alkyl-cycloalkyl, wherein lower alkyl and cycloalkyl are as defined herein. Examples of -lower alkyl-cycloalkyl groups include, but are not limited to, —$CH_2$-cyclopropyl, —$CH_2$-cyclobutyl, —$CH_2$-cyclopentyl, —$CH_2$-cyclopentadienyl, —$CH_2$-cyclohexyl, —$CH_2$-cycloheptyl, or —$CH_2$-cyclooctyl. The "cycloalkyl" can be optionally substituted. A "cycloheteroalkyl", as used herein, unless otherwise indicated, can include any of the above with a carbon substituted with a heteroatom (e.g., O, S, N).

The term "heterocyclic" or "heteroaryl", as used herein, unless otherwise indicated, can include an aromatic or non-aromatic cycloalkyl in which one to four of the ring carbon atoms are independently replaced with a heteroatom from the group consisting of O, S, and N. Representative examples of a heterocycle include, but are not limited to, benzofuranyl, benzothiophene, indolyl, benzopyrazolyl, coumarinyl, isoquinolinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, or tetrazolyl. Heterocycles can be substituted or unsubstituted. Heterocycles can also be bonded at any ring atom (i.e., at any carbon atom or heteroatom of the heterocyclic ring). A heterocyclic can be saturated, partially saturated, or unsaturated. The "heterocyclic" can be optionally substituted.

The term "indole", as used herein, is an aromatic heterocyclic organic compound with formula $C_8H_7N$. It has a bicyclic structure, consisting of a six-membered benzene ring fused to a five-membered nitrogen-containing pyrrole ring. The "indole" can be optionally substituted.

The term "cyano", as used herein, unless otherwise indicated, can include a —CN group. The "cyano" can be optionally substituted.

The term "alcohol", as used herein, unless otherwise indicated, can include a compound in which the hydroxyl functional group (—OH) is bound to a carbon atom. In particular, this carbon center should be saturated, having single bonds to three other atoms. The "alcohol" can be optionally substituted.

The term "solvate" is intended to mean a solvate form of a specified compound that retains the effectiveness of such compound. Examples of solvates include compounds of the invention in combination with, for example, water, isopropanol, ethanol, methanol, dimethylsulfoxide (DMSO), ethyl acetate, acetic acid, or ethanolamine.

The term "mmol", as used herein, is intended to mean millimole. The term "equiv", as used herein, is intended to mean equivalent. The term "mL", as used herein, is intended to mean milliliter. The term "g", as used herein, is intended to mean gram. The term "kg", as used herein, is intended to mean kilogram. The term "µg", as used herein, is intended to mean micrograms. The term "h", as used herein, is intended to mean hour. The term "min", as used herein, is intended to mean minute. The term "M", as used herein, is intended to mean molar. The term "µL", as used herein, is intended to mean microliter. The term "µM", as used herein, is intended to mean micromolar. The term "nM", as used herein, is intended to mean nanomolar. The term "N", as used herein, is intended to mean normal. The term "amu", as used herein, is intended to mean atomic mass unit. The term "° C.", as used herein, is intended to mean degree Celsius. The term "wt/wt", as used herein, is intended to mean weight/weight. The term "v/v", as used herein, is intended to mean volume/volume. The term "MS", as used herein, is intended to mean mass spectroscopy. The term "HβLC", as used herein, is intended to mean high performance liquid chromatograph. The term "RT", as used herein, is intended to mean room temperature. The term "e.g.", as used herein, is intended to mean example. The term "N/A", as used herein, is intended to mean not tested.

As used herein, the expression "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, or pamoate (i.e., 1,1'-methylene-bis-(2-hydroxy-3-naphthoate)) salts. A pharmaceutically acceptable salt may involve the inclusion of another molecule such as an acetate ion, a succinate ion, or another counterion. The counterion may be any organic or inorganic moiety that stabilizes the charge on the parent compound. Furthermore, a pharmaceutically acceptable salt may have more than one charged atom in its structure. In instances where multiple charged atoms are part of the pharmaceutically acceptable salt, the pharmaceutically acceptable salt can have multiple counterions. Hence, a pharmaceutically acceptable salt can have one or more charged atoms and/or one or more counterion. As used herein, the expression "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine. As used herein, the expression "pharmaceutically acceptable hydrate" refers to a compound of the invention, or a salt thereof, that further can include a stoichiometric or non-stoichiometric amount of water bound by non-covalent intermolecular forces.

Formulation

The agents and compositions described herein can be formulated in any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutically active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic, or other physical forces.

Controlled-release (or sustained-release) preparations may be formulated to extend the activity of the agent(s) and reduce dosage frequency. Controlled-release preparations can also be used to affect the time of onset of action or other characteristics, such as blood levels of the agent, and consequently, affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Also provided is a process of treating, preventing, or reversing a bacterial infection in a subject in need of administration of a therapeutically effective amount of a DHFS inhibiting agent (or an anti-folate therapy), so as to treat or prevent a bacterial infection.

Methods described herein are generally performed on a subject in need thereof. A subject in need of the therapeutic methods described herein can be a subject having, diagnosed with, suspected of having, or at risk for developing a bacterial infection or antibiotic resistance. A determination of the need for treatment will typically be assessed by a history, physical exam, or diagnostic tests consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and humans or chickens. For example, the subject can be a human subject.

Generally, a safe and effective amount of DHFS inhibiting agent is, for example, an amount that would cause the desired therapeutic effect in a subject while minimizing undesired side effects. In various embodiments, an effective amount of a DHFS inhibiting agent described herein can substantially inhibit a bacterial infection or antibiotic resistance, slow the progress of a bacterial infection or antibiotic resistance, or limit the development of a bacterial infection or antibiotic resistance.

According to the methods described herein, administration can be parenteral, pulmonary, oral, topical, intradermal, intramuscular, intraperitoneal, intravenous, intratumoral, intrathecal, intracranial, intracerebroventricular, subcutaneous, intranasal, epidural, ophthalmic, buccal, or rectal administration.

When used in the treatments described herein, a therapeutically effective amount of a DHFS inhibiting agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to inhibit DHFS activity.

The amount of a composition described herein that can be combined with a pharmaceutically acceptable carrier to produce a single dosage form will vary depending upon the subject or host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; the activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing, reversing, or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or a physician.

Administration of a DHFS inhibiting agent can occur as a single event or over a time course of treatment. For example, a DHFS inhibiting agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to or before, concurrent with, or after conventional treatment modalities for a bacterial infection or antibiotic resistance.

A DHFS inhibiting agent can be administered simultaneously or sequentially with another agent, such as an antibiotic, an anti-inflammatory, or another agent. For example, a DHFS inhibiting agent can be administered simultaneously with another agent, such as an antibiotic or an anti-inflammatory. Simultaneous administration can occur through administration of separate compositions, each containing one or more of a DHFS inhibiting agent, another antibiotic, an anti-inflammatory, or another agent. Simultaneous administration can occur through administration of one composition containing two or more of a DHFS inhibiting agent, another antibiotic, an anti-inflammatory, or another agent. A DHFS inhibiting agent can be administered sequentially with another antibiotic, an anti-inflammatory, or another agent. For example, a DHFS inhibiting agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intratumoral, intranasal, inhalation (e.g., in an aerosol), implanted, intramuscular, intraperitoneal, intravenous, intrathecal, intracranial, intracerebroventricular, subcutaneous, intranasal, epidural, intrathecal, ophthalmic, transdermal, buccal, and rectal.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can:

provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency; improve taste of the product; or improve shelf life of the product.

Screening

Also provided are screening methods for screening agents for DHFS inhibiting activity.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 MW, or less than about 1000 MW, or less than about 800 MW) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example, ChemBridge, Princeton BioMolecular, Ambinter SARL, Enamine, ASDI, Life Chemicals, etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict the bioavailability of a compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

Kits if desired, be presented in a pack or dispenser device which may contain one or more unit dosage forms containing the composition. The pack may for example, comprise metal or plastic foil such as a blister pack.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Synthetic Efforts Towards a 3-Hydroxy-B-Lactam Warhead

Three synthetic route attempts were made towards the synthesis of a 3-(para-amino-phenyl)-3-HβL mimetic of para-amino-benzoic acid (PABA) suitable for further testing with folate biosynthetic enzymes. The first route utilized a photocyclization of a R-keto-formamide to form the β-lactam ring but was unsuccessful in affording a 3-HβL with a suitable para-amino substituent at the 3C position. The second route utilized a t-butyl magnesium chloride mediated ring closing of an N-protected R-amino-ester to form the β-lactam ring but final deprotection of the β-lactam ring was unsuccessful. The third route utilized a t-butyl magnesium chloride mediated ring closing reaction as well, but with an unprotected β-amino-ester. The third route was successful in affording a fully deprotected 3-(para-NH$_2$-phenyl)-3-HβL as a suitable PABA mimetic. This compound was carried forward for biochemical testing as a substrate and inhibitor of enzymes in the folate pathway.

Introduction

Given the importance of β-lactam based antibiotics in the arsenal of humanity's fight against bacterial infection, the many routes towards chemical synthesis of β-lactam scaffolds are well-explored. However, given the relative rarity and novelty of 3-HβL based antibiotic compounds, the routes to synthesize these scaffolds are less well-explored. This is due, in part, to the difficulty of installing the hydroxylated quaternary 3C-chiral center via standard synthetic methods for β-lactam ring construction. Hence, the synthetic efforts to achieve the 3-HβL compounds described herein may successfully use two synthetic route changes and protecting group manipulations to reach the desired synthetic targets.

Figure 2D:
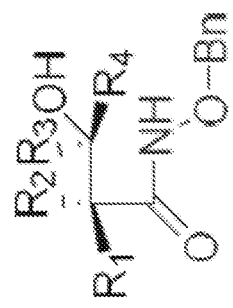
Figure 2D:
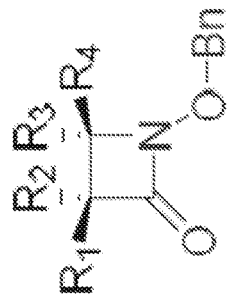

Retrosynthesis of the proposed 3-HβL compounds began with bond disconnection between the pterin benzylic methylene carbon and the aniline nitrogen of the 3-(para-NH$_2$-phenyl)-3-HβL moiety (see e.g., FIG. 1). The 3-HβL ring may be further broken down by either a 1N-2C separation or a 2C-3C separation (see e.g., FIG. 1). The para-NH$_2$-phenyl linker may be in place before the 1 N-2C bond creation or installed after given a suitable ketone and nucleophile at the 3C (see e.g., FIG. 1). Other β-lactam bond disassociations and their respective forward syntheses are discussed herein. Herein, the efforts to synthesize 3-(para-NH$_2$-phenyl)-3-HβL through forward syntheses that make the 1 N-2C or 2C-3C bond are described.

β-lactams have been synthesized in numerous ways throughout history, and each classic method offers advantages and disadvantages related to control of regioselective, stereoselective, and substrate scope. In 1943, Gilman and Speeter introduced a method for building β-lactams through an enolate—imine condensation, which was expanded by the Newcomb group in 1980 (see e.g., FIG. 2A). While this method is attractive in its simple conditions and scalability, this method is not suitable for the purposes of achieving the 3-HβL warhead desired given the following: Reported examples require a carbon based group bonded to the imine nitrogen, and reported examples require an aryl substituent at 4C of the β-lactam ring, which is exclusionary to the unsubstituted C4 methylene required for the target compound of this study, 3-(para-NH$_2$-phenyl)-3-HβL.

Figure 2E:
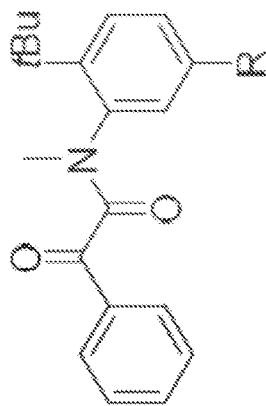
Figure 2E:
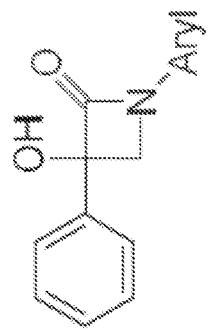

Corey and Felix reported a β-lactam synthesis (see e.g., FIG. 2B) using a carbene C—H insertion in 1965. Enantioselectivity of the 3C and 4C substituents was reported by Doyle and co-workers in 1993. This route is again attractive in its simplicity, but would fail to achieve a β-lactam with an oxygen bonded to 3C of the β-lactam ring, which means any route including such a synthetic transformation would include additional steps and protecting group manipulations to achieve the desired 3-HβL scaffold. Staudinger reported a β-lactam synthesis using an imine-ketene cycloaddition (see e.g., FIG. 2C) in 1907. Although this route may successfully install a protected oxygen at 3C, this route again places restrictions on the imine nitrogen, namely requiring its protection. The Miller group reported the use of a Mitsunobu cyclization (see e.g., FIG. 2D) to furnish a β-lactam ring in 1980. This method would in theory accommodate 3C-hydroxylation but was not attempted due to lengthy synthetic routes needed to access the cyclization substrates. The Sivaguru group reported 3-HβL synthesis through the photocyclization of α-keto-amide compounds (see e.g., FIG. 2E) in 2009. This method would allow an unprotected hydroxy group at 3C but necessitates an aryl group bound to 1N, and as such, is unsuitable to produce the compounds described herein.

Figure 2F:
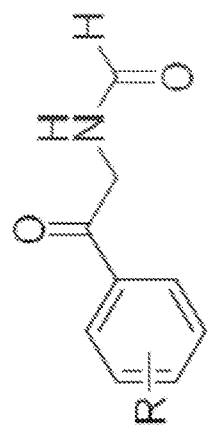
Figure 2F:
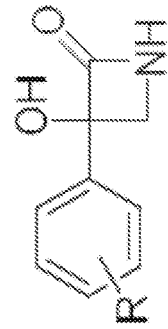

Wehrli reported a synthesis of an unsubstituted 3-HβL (see e.g., FIG. 2F) through a photocyclization of a R-keto-formamide in 1980. Substrate scope and synthetic utility was greatly expanded in 2018 as previously described. This Norrish-Yang type photocyclization has thus far been limited to 3-phenyl-R-keto-formamides, which fits within the scope of the synthetic target herein, 3-(para-NH$_2$-phenyl)-3-HβL. The one-step photochemical method also conveniently inserts the 3C-hydroxyl group and does not require protecting groups. Owing to this type of reaction positioning the hydroxy group (unprotected) at the 3C and an aryl group at the 3C of the β-lactam, it was an attractive starting point. It was hypothesized that a suitable para-substituent would allow for photochemical cyclization and later conversion to the free para-NH$_2$ group. The presence of a free para-NH$_2$ group is central to the planned strategy for benzylic coupling with a pterin moiety via SN2 reaction (see e.g., FIG. 1). The synthetic efforts to adapt the Norrish-Yang photochemical cyclization of phenyl-β-keto-formamides for inclusion of para-amino functionality are described herein.

3-HβL Synthesis by Photocyclization

Figure 3:
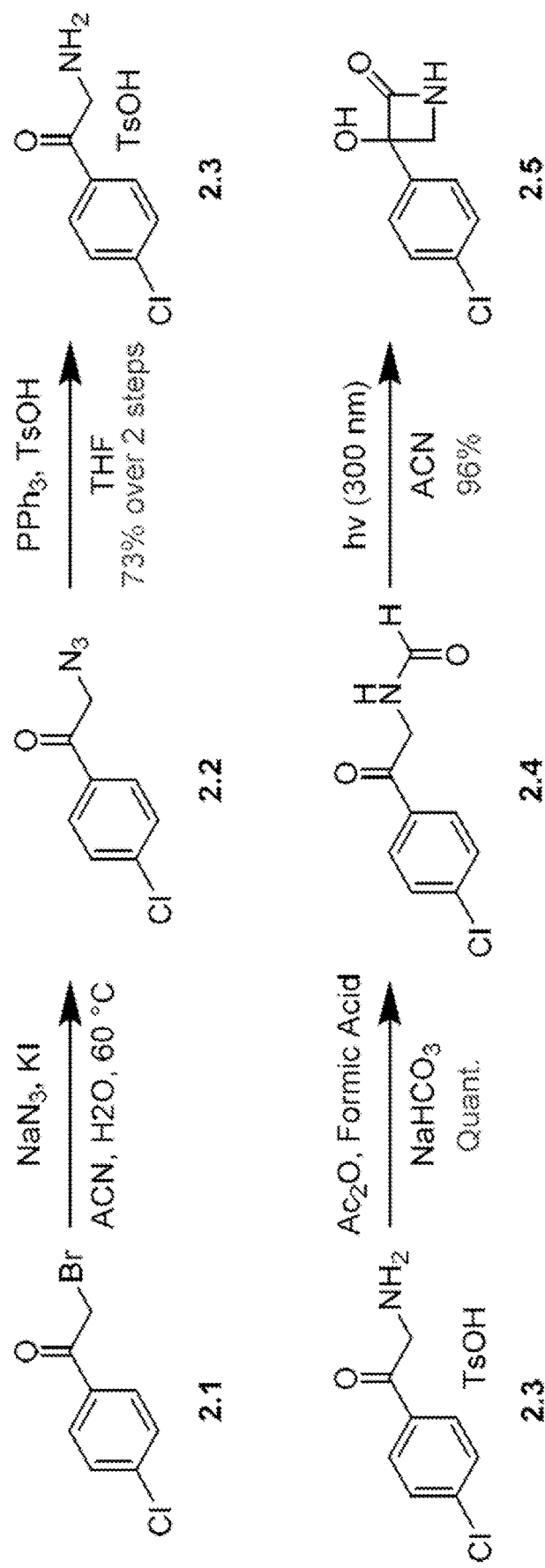
FIG. 3 is a schematic showing synthesis of 3-(para-Cl-phenyl)-3-HβL via a final Norrish-Yang-Wherli photocyclization of a β-ketoformamide precursor in accordance with the present disclosure.

Owing to good photocyclization yield, scalability, and the ability to be functionalized, N-(2-(4-chlorophenyl)-2-oxo-ethyl)formamide 2.4 was chosen as the β-keto-formamide to be cyclized (see e.g., FIG. 3). 2-bromo-1-(4-chlorophenyl)ethan-1-one 2.1 was transformed to the corresponding azide through a simple Sn2 addition. Azide 2.2 was reduced using a Staudinger reduction with triphenylphosphine in the presence of tosylic acid to provide the corresponding tosylic acid salt 2.3. Inclusion of tosylic acid prevents spontaneous pyrazine formation. Formylation of the terminal amine was achieved using acetic anhydride and formic acid afforded β-keto-formamide 2.4. Order of addition was used to prevent pyrazine formation under basic conditions. For the photocyclization step, 2.4 was dissolved in degassed acetonitrile and illuminated with 300 nm light in 30-minute intervals until the reaction was complete by NMR analysis. Leaving the reaction past its completion may lead to decomposition into unknown products.

Figure 4:
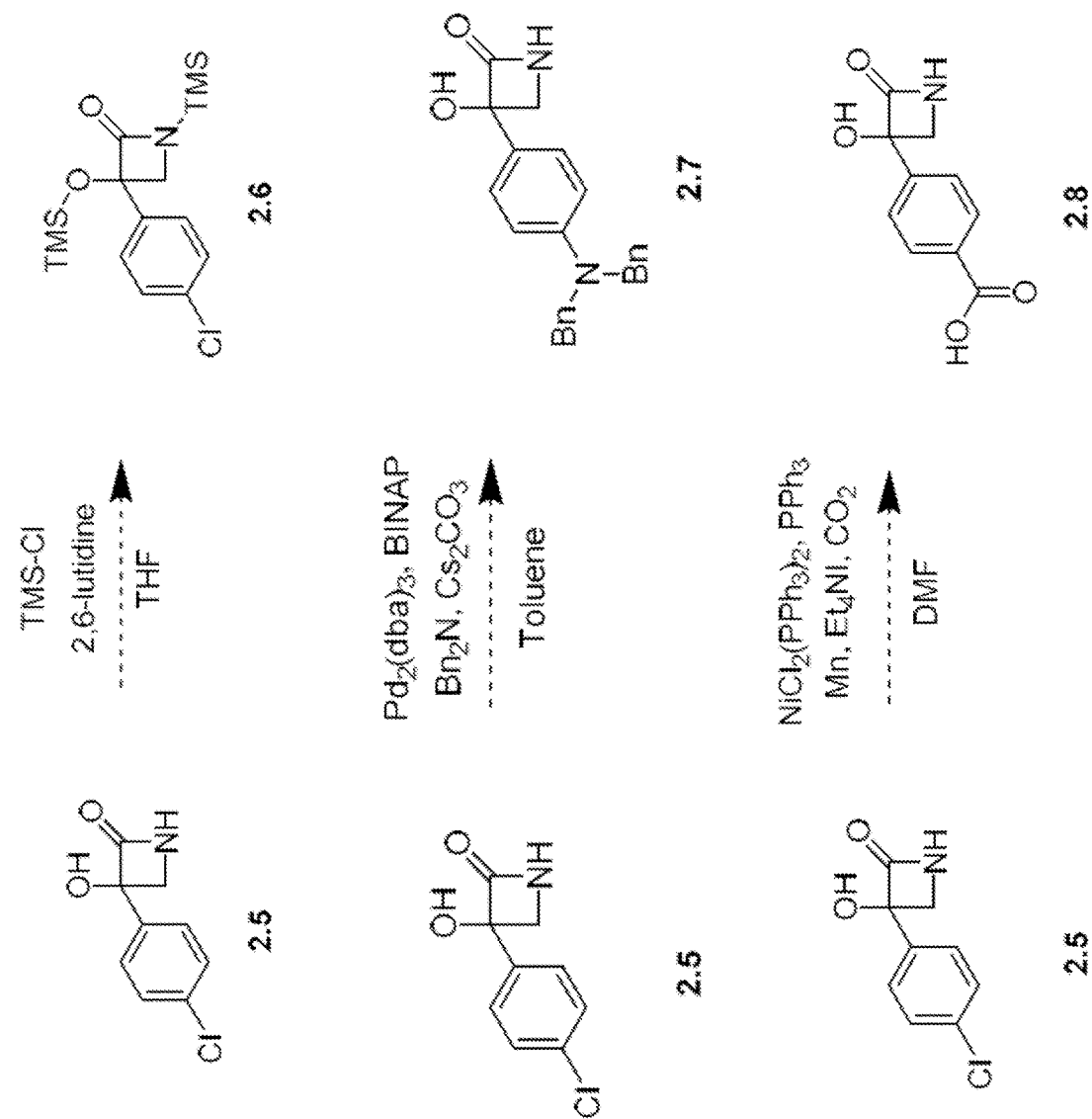
FIG. 4 includes schematics showing unsuccessful attempts towards the installation of a nitrogen at the para position of the aryl ring via conversion of a para chloro substituent in accordance with the present disclosure.

Having fully assembled the 3-HPβL ring, the remaining steps include conversion of the p-chloro group to some type of protected or unprotected nitrogen (see e.g., FIG. 4). Attempts to add a silyl protecting group (trimethylsilyl) on the nitrogen of the q-lactam and the oxygen at 30 were unsuccessful (see e.g., FIG. 4). Attempts to perform a Buchwald-Hartwig amination were unsuccessful (see e.g., FIG. 4). Attempts to convert the p-chloro group to a carboxylic acid with the intention of performing a Curtius rearrangement were unsuccessful (see e.g., FIG. 4). Conditions for these reaction attempts can be found in TABLE 1.

TABLE 1

Conditions for reactions of the p-chloro-aryl-3-HβL in FIG. 4.

| Starting Material | Reagents | Solvent | Temperature | Result |
| --- | --- | --- | --- | --- |
| Benzyl-NH$_2$ | 1.5 Equiv K$_2$CO$_3$, 0.1 Equiv Pd(dppf)Cl$_2$ | Toluene | 80° C. | No Product Observed |
| Benzyl-NH$_2$ | 2 Equiv Cs$_2$CO$_3$, 0.1 Equiv Pd(OAc)$_2$, 0.1 Equiv BINAP | Toluene | 100° C. | No Product Observed |
| Bn$_2$NH | 2 Equiv Cs$_2$CO$_3$, 0.15 Equiv Pd$_2$(dba)$_3$, 0.15 Equiv BINAP | Toluene | 80° C. | No Product Observed |
| Bn$_2$NH | 2 Equiv Cs$_2$CO$_3$, 0.15 Equiv Pd$_2$(dba)$_3$, 0.15 Equiv BINAP | Toluene | 100° C. | No Product Observed |
| Bn$_2$NH | 2 Equiv sodium t-butoxide, 0.15 Equiv Pd$_2$(dba)$_3$, 0.15 Equiv BINAP | Toluene | 80° C. | No Product Observed |
| Bn$_2$NH | 2 Equiv sodium t-butoxide, 0.15 Equiv Pd$_2$(dba)$_3$, 0.15 Equiv BINAP | Toluene | 100° C. | No Product Observed |
| CO$_2$ | 0.1 Equiv PPh$_3$, 0.1 Equiv Et4NI, 3 Equiv Mn, 0.05 Equiv NiCl$_2$(PPh$_3$)$_2$ | DMF | 25° C. | No Product Observed |
| TMS-Cl | 3 Equiv 2,6-lutidine | THF | 25° C. | Mixture of Single and Double Protection |

Figure 5A:
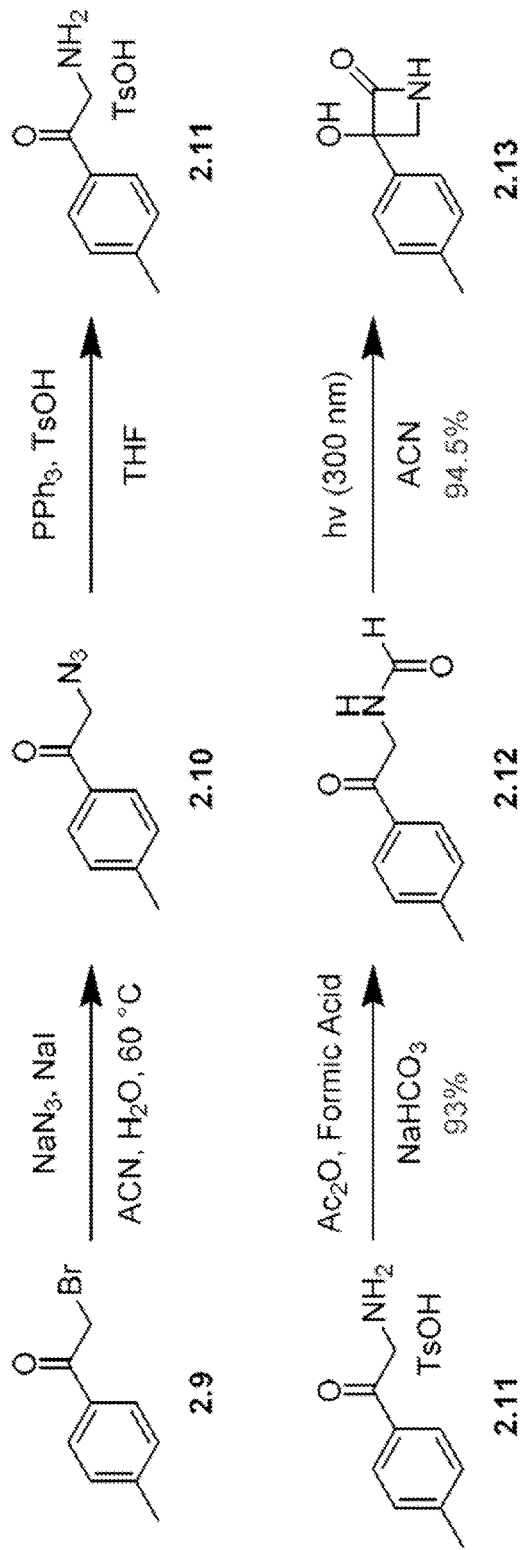
FIG. 5A-FIG. 5C is an exemplary embodiment showing photocyclization route with a para-methyl substituent in accordance with the present disclosure.
Figure 5B:
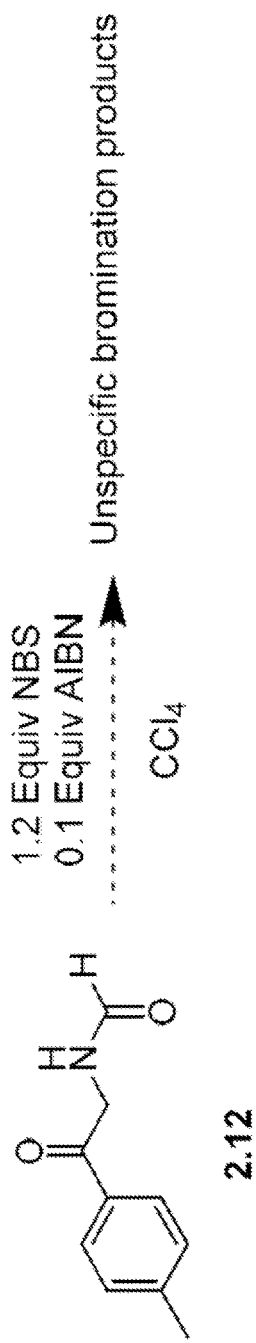
Figure 5C:
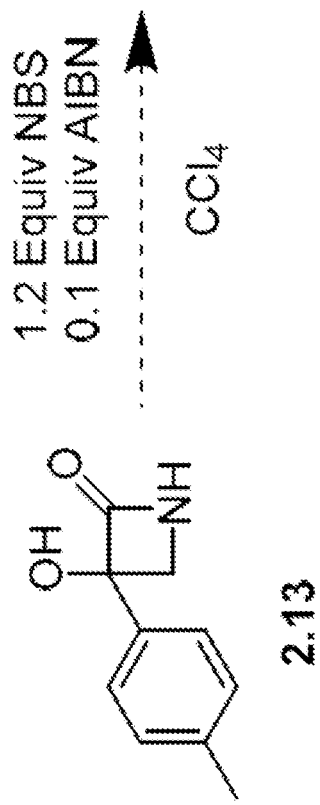
Figure 5C:
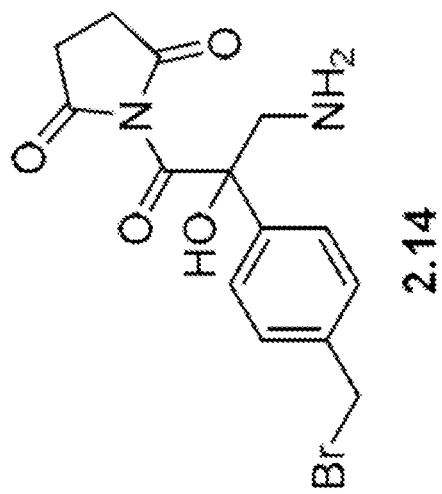
Figure 6:
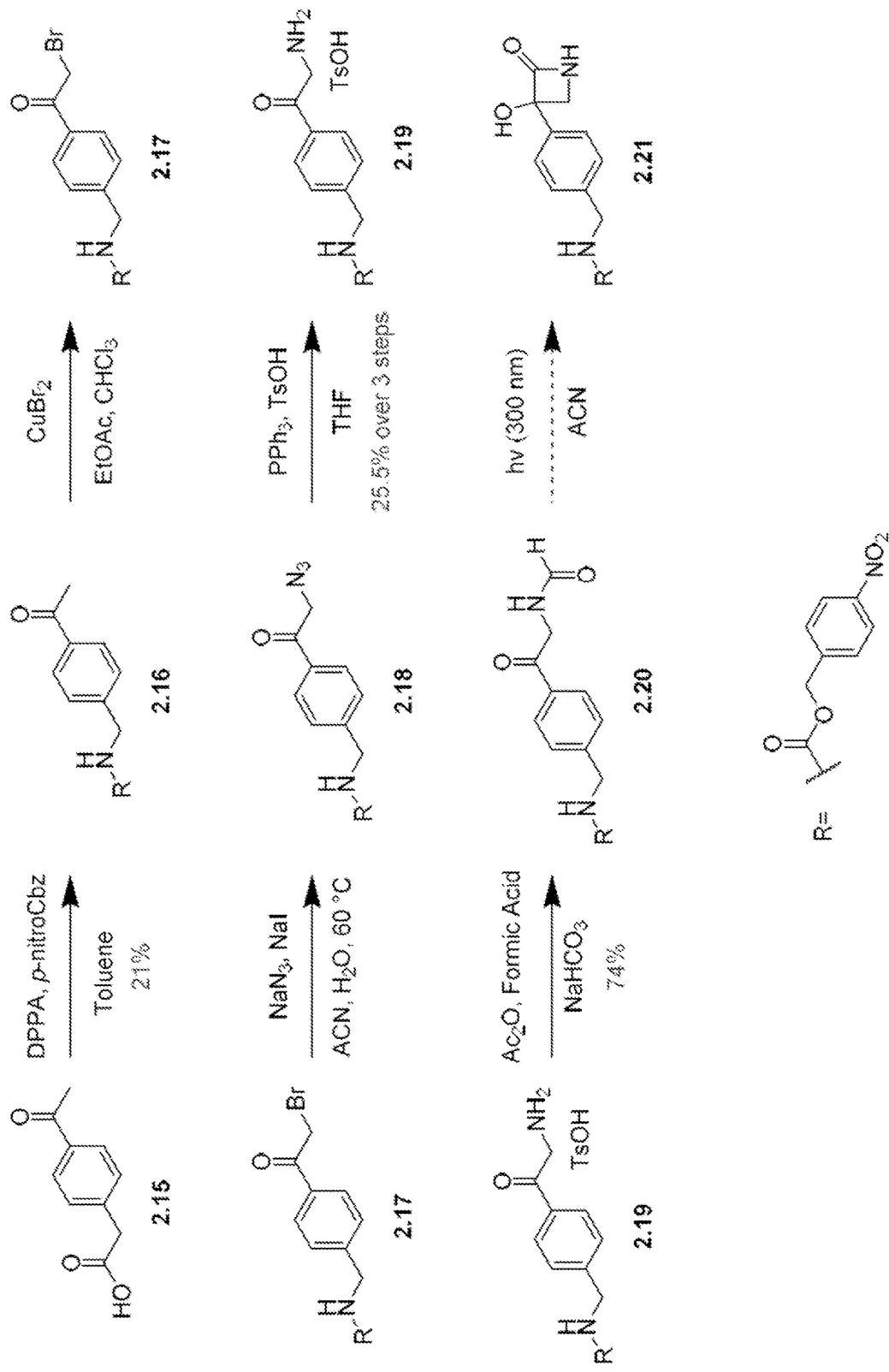
FIG. 6 is a schematic showing unsuccessful photocyclization route synthesis with the methylene spacer installed early in the synthetic route in accordance with the present disclosure.
Figure 7:
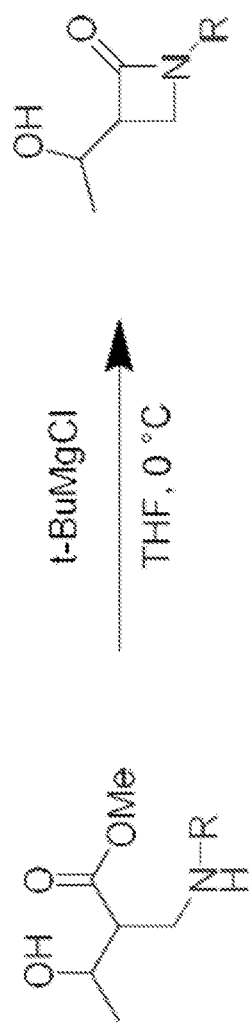
FIG. 7 is a schematic showing Grignard mediated ring closure of R-amino acids in accordance with the present disclosure.

As described herein, molecular modeling suggested a methylene spacer at the para-position is tolerated. Hence, a synthetic route to a 3-(para-methylaminophenyl)-3-HPβL derivative (2.13) via photocyclization of a suitable phenyl-β-keto-formamide precursor was designed (see e.g., FIG. 5A). Bromination of this benzylic p-methyl group under radical conditions would install a benzylic bromide electrophile to allow SN2 displacement with sodium azide and subsequent reduction to afford a 3-HPβL with a para-methylamino substituent 2.13. However, bromination prior to the photocyclization was unsuccessful, and bromination after the photocyclization was unable to be achieved without destroying the β-lactam ring. A suitable radical initiation reagent that does leave behind a nucleophile like light or heat may have been more successful for the post-ring closing bromination. Conditions for these unsuccessful reactions can be found in FIG. 5A-FIG. 5O. To overcome this limitation, the synthetic route was amended to include the methylene spacer at an earlier stage. Unable to purchase a suitable starting material to this end, a Curtius rearrangement was used to install and protect the terminal amine in one step (see e.g., FIG. 6). The photocyclization did not proceed and starting material was recovered. It is possible this photocyclization did not proceed due to the aniline protecting group absorbing the nm light used to excite the β-ketone. Thus, a new synthetic strategy was pursued using a Grignard-mediated cyclization of b-amino-esters (see e.g., FIG. 7) to install the b-lactam ring.

3-HβL Synthesis by Aryl Addition to α-Keto-β-Lactams

Figure 8:
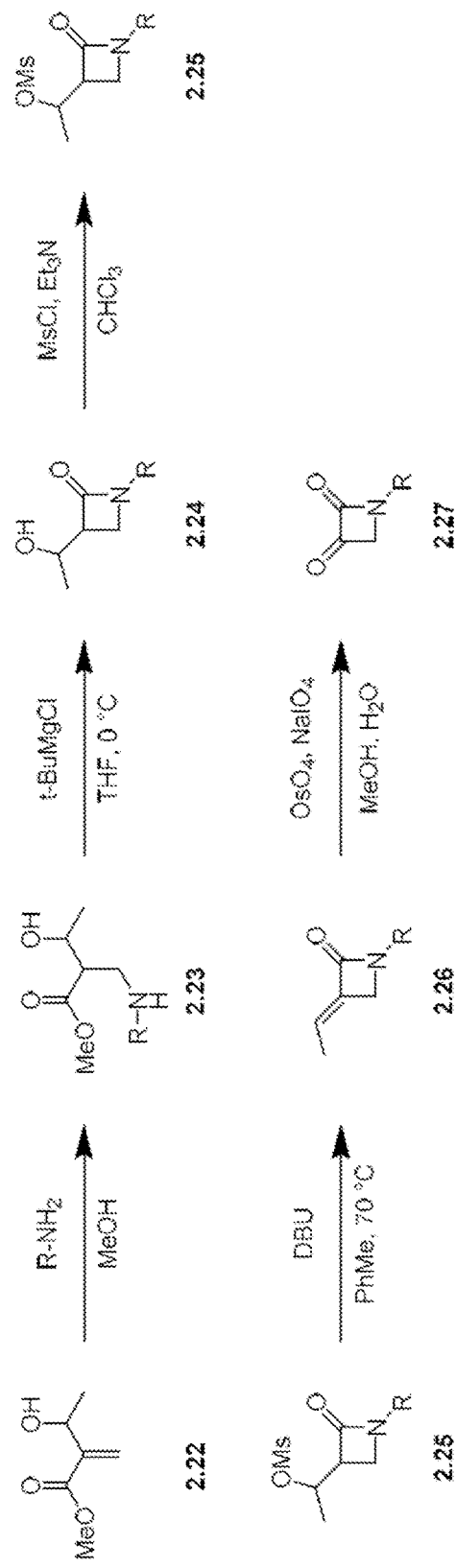
FIG. 8 is a schematic showing synthesis route to a protected α-keto-β-lactam in accordance with the present disclosure.
Figure 9:
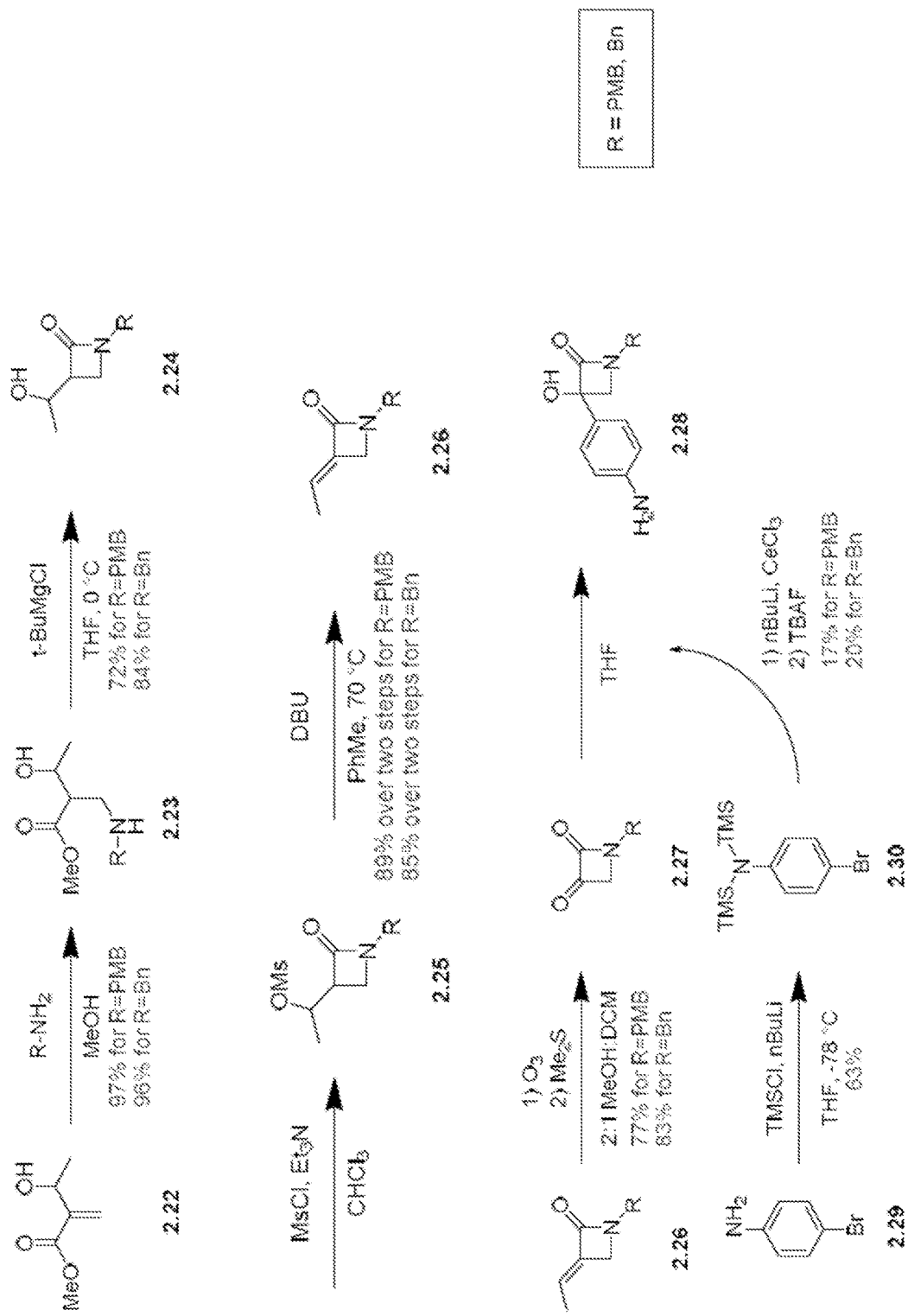
FIG. 9 is a schematic showing updated Paquette routing and subsequent aryl-nucleophile addition to the α-keto-β-lactam in pursuit of an unsubstituted 3-HβL in accordance with the present disclosure.

Paquette and co-workers previously reported the synthesis of an α-keto-β-lactam 2.27 by way of osmium oxidation of E/Z olefins 2.26 (see e.g., FIG. 8). A simple aryl nucleophile addition to the ketone of 2.27 would afford the desired 3-HβL scaffold. A synthetic route via this logic was designed as shown in FIG. 9. A Michael addition of p-methoxybenzyl-amine (PMB-amine) to the acrylate Michael acceptor 2.22 provided the N-PMB R-amino-ester needed for cyclization to the β-lactam ring. Cyclization to the β-lactam 2.24 was achieved by treatment with t-butyl magnesium chloride. Mesylation of the secondary alcohol followed by subsequent elimination with 1,8-Diazabicyclo[5.4.0]undec-7-ene (DBU) afforded the methyl olefin 2.26. While Paquette and co-workers used an osmium-based oxidation to oxidize the olefin, ozonolysis quenching with dimethyl sulfide developed by Williams and coworkers proved an easier, cleaner, and higher yielding reaction to afford α-keto-β-lactam 2.27. Several methods to generate an anion at the para position of an aniline were attempted (see e.g., TABLE 2).

TABLE 2

Summary of attempts to make an anion at the para position of a protected aniline.

| Starting Material | Reagents | Solvent | Temperature | Result |
|---|---|---|---|---|
| P Nitro | 3 Equiv Mg Strips | THF | 25° C. | No Reaction |
| N,N-Dibenzyl | 3 Equiv Mg Strips | THF | Reflux | No Reaction |
| N,N-Dibenzyl | 1.1 Equiv Mg Strips, 1 Equiv LiCl | THF | Reflux | No Reaction |
| N,N-Dibenzyl | 3 Equiv Mg Strips, 0.1 Equiv Phenyl-MgBr | THF | 25° C. | No Reaction |
| N,N-Dibenzyl | 1 Equiv Mg Strips | THF distilled over molecular sieves | Reflux | No Reaction |
| N,N-Dibenzyl | 0.95 Equiv n-BuLi | THF | −78° C. | No Reaction |
| N,N-Dibenzyl | 1 Equiv Li metal | THF/Hexanes | 25° C. | No Reaction |
| N,N-cyclic-silyl | 1 Equiv Li metal | Diethyl Ether | 25° C. | No Reaction |
| N,N-cyclic-silyl | 1 Equiv Li metal | THF | 25° C. | No Reaction |
| N,N-diTMS | 1 Equiv Mg Strips | THF | 25° C. | No Reaction |
| N,N-diTMS | 1 Equiv n-BuLi | THF | −78° C. | Anion generation but no addition |
| N,N-diTMS | 1 Equiv n-BuLi | THF | 0° C. | Anion generation but no addition |
| N,N-diTMS | 1 Equiv n-BuLi, 1.25 Equiv dry CeCl₃ | THF | −78° C. | Successful addition |

N,N-dibenzyl-protected aniline and p-nitro-aniline were synthesized from p-bromo-aniline or bought (respectively) but were unsuccessfully used to make an anion through Grignard conditions and lithium halogen exchange (both radial and anion methodology). No reaction was seen from the magnesium strips used, even when scored prior to use, indicating possible water contamination even under drying and inert atmosphere conditions. The alkyl-lithium bases and lithium metal behaved similarly with no reaction occurring, although the alkyl lithium bases may have simply deprotonated the benzylic protons of the N-benzyl protecting groups rather than doing any lithium-halogen exchange.

A cyclic silyl protecting group was similarly unsuccessful in generating the desired anion (see e.g., TABLE 2). Generating an anion from an N,N-di-TMS-protected aniline 2.30 through lithium halogen exchange followed by adding the aforementioned anion to α-keto-β-lactam 2.27 resulted in the generation of an enolate at 3C, and upon quenching, the α-keto-β-lactam was returned unchanged. Dry CeCl₃ addition to the lithium halogen exchange product prior to anion addition prevents simple enolate formation and quenching. With the lithium halogen exchange followed by CeCl₃ conditions, the production of 3-HβL 2.28 was accomplished. Removal of the silyl protecting groups was achieved using TBAF.

Once the N-PMB protected 3-(para-NH₂-phenyl)-HβL 2.28 was synthesized, the last step was to remove the PMB protecting group from the β-lactam nitrogen. Paquette and co-workers previously were able to deprotect this nitrogen with simple hydrogenation. Given PMB groups are typically labile enough to remove with oxidation or strong acid conditions, a gamut of common conditions was explored but yielded either no reaction or decomposition into unspecified compounds. Given a benzyl protecting group could replace the PMB protecting group and is normally easy to remove with simple hydrogenation like the Paquette group was able to achieve, the entire synthesis route was redone with a benzyl protected amine to start with. However, the gamut of common hydrogenation conditions was attempted on both the benzyl and PMB protected β-lactam and was unsuccessful in yielding an unfurnished 3-HβL. For a list of conditions tried, see TABLE 3.

TABLE 3

List of conditions towards the deprotection of a 3-HβL.

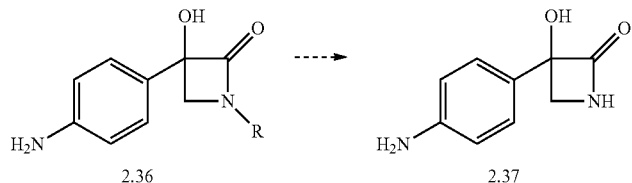

| R Group | Removal Conditions | Result |
|---------|-------------------|--------|
| Benzyl | H₂, Pd/C | No reaction |
| Benzyl | H₂, Pd/C, PTSA | No reaction |
| Benzyl | H₂, Pd/C, 50 psi | No reaction |
| PMB | H₂, Pd/C, PTSA | No reaction |
| PMB | TFA, Triethylsilane | No reaction |
| PMB | TFA, Triethylsilane, 60° C. | No reaction |
| PMB | DDQ | Decomposition |
| PMB | CAN | Decomposition |

Once it was established that the protected β-lactams were unsuitable for achieving the desired unfurnished 3-HβL, a new synthetic route was designed to avoid the use of problematic protecting groups. If the t-butyl magnesium chloride mediated ring closing could be harnessed as the last step of the route, then protection of the nitrogen might not be necessary. This would entail installing the aniline linker portion first, then closing the ring (protecting group free). The synthetic route established to accomplish this transformation is discussed below.

3-HβL Synthesis by Henry Reaction

Figure 12:
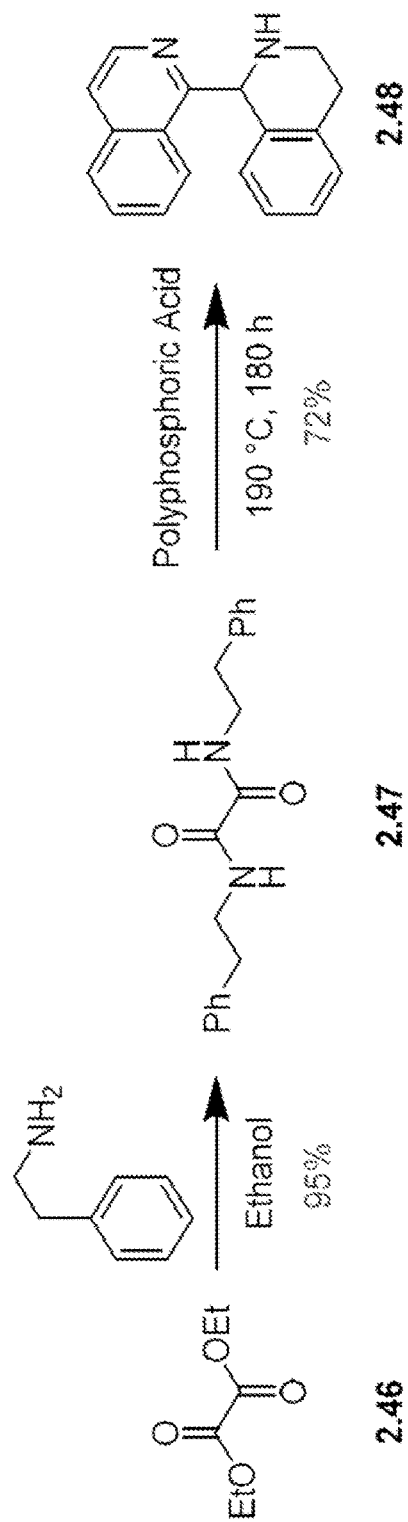
FIG. 12 is a schematic showing synthesis of the non-nucleophilic base used in the Henry reaction in FIG. 11 in accordance with the present disclosure.
Figure 13:
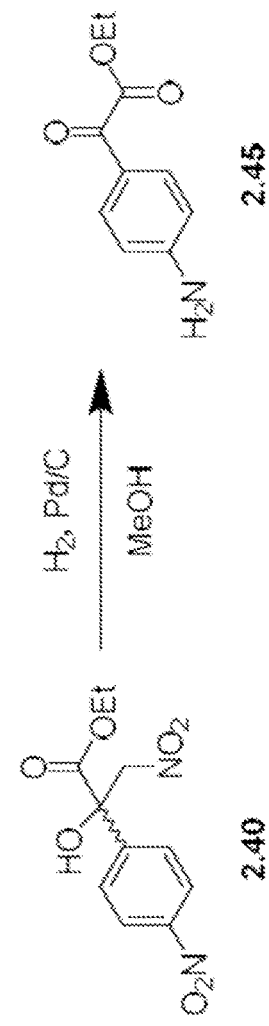
FIG. 13 is a schematic showing failure to adequately protonate the aryl nitrogen after reduction results in reverse-Henry elimination of nitromethane in accordance with the present disclosure.

Deng and co-workers previously showed that the t-butyl magnesium chloride mediated ring closing could be performed on an unprotected amine and with the tertiary hydroxyl group that will eventually be the 3-hydroxy group in the β-lactam also unprotected (see e.g., FIG. 10A). Judeh and co-workers showed in that a Henry reaction can be used to add a nitromethane group to an α-keto-ester with a p-nitro aniline already in place (see e.g., FIG. 10B). With these two transformations established, the successful route to an unfurnished, unprotected 3-HβL was begun (see e.g., FIG. 11). β-keto-ester 2.38 was oxidized in a Cu(I) and TEMPO mediated reaction to afford α-keto-ester 2.39. The racemic addition of nitromethane to α-keto-ester 2.39 was achieved using the base synthesized in FIG. 12. Stereochemical considerations of the 3C groups are discussed below. Reduction of both nitro groups simultaneously was achieved using hydrogenation supplemented by 1 equivalent of p-toluenesulfonic acid (PTSA). Failure to acidify the reaction resulted in a reverse-Henry elimination of nitromethane (see e.g., FIG. 13) due to the aryl-nitro group reducing first, making the benzylic position more electron dense, allowing reformation of the ketone. Keeping the aryl-nitrogen protonated after it is reduced prevents this reverse-Henry reaction, and once the alkyl-nitro group has been fully reduced, the acid can be removed by ion-exchange chromatography as there is no longer a suitable leaving group at the benzylic position. Addition of t-butyl magnesium chloride to 2.41 did not result in the desired ring closure (not shown). Upon selective protection of the aryl-nitrogen through buffered Boc protection conditions, the ring closing proceeds, albeit with relatively low yield. By starting material conversion, the reaction goes to completion with only the aryl-nitrogen being protected but getting the product out of the aqueous layer and away from any salts proved to be mass limiting, causing a low recovered yield at the end of the extraction and purification process. Simple anhydrous TFA deprotection of the Boc group afforded the unsubstituted 3-HβL 2.44.

Discussion

Photocyclization was used herein to form an unsubstituted and unprotected 3-HβL from a simple and readily synthesized R-keto-formamide precursor. The reactions in the route are simple, quick, high yielding, and easy to purify. While this route was unable to afford a para-amino-aryl ring at 3C, it is a promising way to form a large variety of β-lactams. The photocyclization itself is very sensitive to electron donating groups at the para position of the aryl ring and to heavy atom effects. A protected carboxylic acid of some type with a methylene spacer to the aryl ring may allow for the photocyclization to proceed, to be followed up by a postcyclization Curtius rearrangement (rather than the pre-cyclization Curtius rearrangement attempted here). A different protecting group strategy for the aryl-CH₂—NH—R compounds prior to photocyclization is also a potential path forward.

It is still unclear why the Paquette group was able to deprotect their pi-lactams through simple hydrogenation when the 3-HβL compounds synthesized herein were resistant to deprotection. Both electronic and steric arguments seem unconvincing as to why hydrogenation, particularly at high pressure, proved unfruitful. Reversing the synthetic logic and assembling the β-lactam ring as the last complicated step was instrumental in achieving the final 3-HβL. While the stereochemical considerations of the 3C position of the β-lactam are discussed herein, it should be noted that Deng and co-workers were able to perform the Henry addition of nitromethane to suitable α-keto-esters with high stereospecificity using Cinchona alkaloid derivatives. Should the need to set the 3C stereocenter arise, it is likely that modifications of the third synthetic route (switching out the base catalyst of the Henry reaction to a cinchona alkaloid derivative) can achieve this. Should the need arise to have substituents at the 4C position of the 3-HβL, there is precedent for substituting alternative alkyl-nitro compounds for the nitromethane in the Henry reaction.

A nitrogen linker from the aryl ring at 3C to the pterin group may not be required. Perhaps a sulfur or oxygen linker, or even a fully alkyl linker would be possible. Given these possibilities, some alternative routes to 3-HβL compounds are also discussed herein.

Conclusion

The synthetic route featuring a Henry reaction to install the tertiary alcohol and necessary scaffold leading to the beta-amino acid allows for scalable synthesis of the desired 3-HβL. Only 3 silica columns are needed for the route, and one of them (the Henry reaction purification) may be run isocratically. While the hydrogenation benefits from high pressure, the reaction proceeds cleanly, and addition of anion-exchange resin followed by filtering is the only purification that was used. The 3-HβL ring remains remarkably stable given its strained nature, capable of being left in atmosphere for days without decomposing. Concentrated aqueous acid was used to hydrolyze the beta-lactam ring. Knowledge was gained in the areas of synthesis, purification, route scouting/planning, and multigram scale reactions. Clean samples of the 3-HβL warhead with the desired para-$NH_2$ substituent were obtained and full NMR analysis confirmed the structure. Key indicators of the intact β-lactam ring are the diastereotopic protons of 4C forming a doublet of doublets, and the singlet hydroxyl proton making 2D interactions with 4C in the HMBC spectrum. These samples are suitable for biochemical testing against proposed targets with no convoluting factors from impurities.

Materials and Methods

All chemicals and solvents were purchased from reputable vendors (ex. Sigma Aldrich, Oakwood, Enamine, Thermo Fisher). All prep-HβLC was performed using an Agilent/HP 1050 quaternary pump module with an Agilent/HP MWD module with a Phenomenex Luna 10u C18(2) 100A column, 250×21.20 mm, 10 μm with guard column. All LCMS was performed on an Agilent 6130 quadrupole LC-MS with G1313 autosampler or G1367B autosampler, G1315 diode array detector, and 1200 series solvent module. A Phenomenex Gemini C18 column, 50×2 mm, 5 μm with guard column was used for all LC-MS separations. Mobile phases for prep-HβLC and LCMS were 0.1% formic acid in (A) $H_2O$ and (B) $CH_3CN$, and data were processed using ChemStation software (Agilent). NMR was performed on either an Agilent DD2 600 MHz, an Agilent DD2 500 MHz, or a Varian Unity Plus 300 MHz instrument and data was processed using MestraNova. All optical absorption plate readings were performed on either a Spectra Max Plus 384 or a Fisher AccuSkan Go.

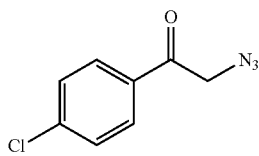 [SMILES: [N-]=[N+]=NCC(=O)c1ccc(Cl)cc1]

2-azido-1-(4-chlorophenyl)ethan-1-one (2.2): To a solution of 2-bromo-1-(4-chlorophenyl)ethan-1-one (3.00 g, 12.9 mmol) in 24 mL ACN/8 mL water was added KI (214 mg, 1.29 mmol) and $NaN_3$ (924 mg, 14.2 mmol). The reaction flask was fitted with a reflux condenser then heated to 60° C. while stirring for 2.5 h. The solution was cooled to 25° C. then diluted with water (30 mL) and extracted with EtOAc (3×20 mL). The organics were collected and dried with $Na_2SO_4$. The organics were filtered then concentrated under pressure and the residue was used crude in the next reaction. Rf=0.6 in 20% EtOAc in Hexanes.

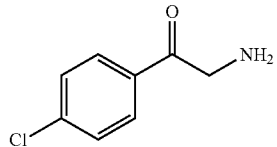 [SMILES: NCC(=O)c1ccc(Cl)cc1]

2-amino-1-(4-chlorophenyl)ethan-1-one (2.3): To a solution of 2-azido-1-(4-chlorophenyl)ethan-1-one (2.52 g, 12.9 mmol) in 65 mL of tetrahydrofuran (THF) was added $PPh_3$ (5.07 g, 19.35 mmol) and p-toluenesulfonic acid $H_2O$ (PTSA) (7.36 g, 38.7 mmol). The reaction flask was fitted with a reflux condenser then heated to 40° C. for 18 h. The solution was cooled to room temperature and filtered to collect 3.207 g (72.89% yield) of white solid (the PTSA salt of 2-amino-1-(4-chlorophenyl)ethan-1-one). 1H NMR (300 MHz, Methanol-d4) δ 8.02 (d, J=8.6 Hz, 2H), 7.70 (d, J=8.2 Hz, 2H), 7.60 (d, J=8.6 Hz, 2H), 7.23 (d, J=8.1 Hz, 2H), 4.58 (s, 2H), 2.37 (s, 3H).

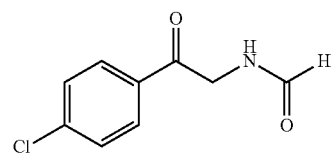 [SMILES: O=CNCC(=O)c1ccc(Cl)cc1]

N-(2-(4-chlorophenyl)-2-oxoethyl)formamide (2.4): To a flask of $Ac_2O$ (26.66 mL, 282 mmol) fitted with a drying tube was added formic acid (11.35 mL, mmol). The solution was headed to 60° C. while stirring for 2 h. The solution was cooled to 25° C. and 2-amino-1-(4-chlorophenyl)ethan-1-one·PTSA (3.207 g, 9.4 mmol) was added. The solution was stirred for 10 min. Sat. $NaHCO_3$(aq) (494 mL) was added dropwise. The solution was extracted with EtOAc (3×200 mL) then the organics were combined, washed with 300 mL sat. NaCl (aq) and dried with $Na_2SO_4$. The organics were filtered then concentrated under pressure to yield 2.57 g of an off-white crystalline solid which was used crude in the next reaction. Excess EtOAc was found in the NMR. 1H NMR (300 MHz, DMSO-d6) δ 8.16 (s, 1H), 8.01 (d, J=8.8 Hz, 2H), 7.62 (d, J=8.8 Hz, 2H), 4.67 (d, J=5.6 Hz, 2H).

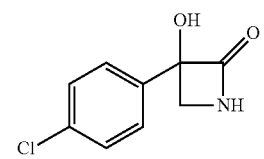 [SMILES: O=C1NCC1(O)c1ccc(Cl)cc1]

3-(4-chlorophenyl)-3-hydroxyazetidin-2-one (2.5): A solution of N-(2-(4-chlorophenyl)-2-oxoethyl)formamide (300 mg, 1.52 mmol) in 30 mL ACN was degassed with argon. The solution was split into 4 quartz test tubes (7.5 mL each) and the test tubes were flushed with argon then capped with parafilm. The quartz test tubes were put in a UV reaction box fitted with 300 nm light bulbs and exposed to UV light for a total of 4.5 h. The test tubes were combined and concentrated under pressure to yield 287 mg (95.6% yield) of a yellow crystalline solid. 1H NMR (300 MHz, Methanol-d4) δ 7.52 (d, J=8.9 Hz, 2H), 7.39 (d, J=8.8 Hz, 2H), 3.57 (d, J=5.4 Hz, 1H), 3.54 (d, J=5.4 Hz, 1H).

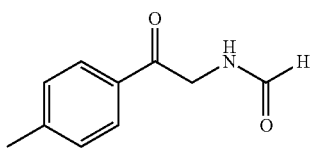

N-(2-oxo-2-(p-tolyl)ethyl)formamide (2.12): To a flask of Ac$_2$O (19.87 mL, mmol) fitted with a drying tube was added formic acid (8.45 mL, 224 mmol). The solution was headed to 60° C. while stirring for 2 h. The solution was cooled to 25° C. and 2-amino-1-(p-tolyl)ethan-1-one·PTSA (2.25 g, 7 mmol, prepared by J M) was added. The solution was stirred for 10 min. Sat. NaHCO$_3$(aq) (368 mL) was added dropwise. The solution was extracted with EtOAc (3×200 mL) then the organics were combined, washed with 300 mL sat. NaCl (aq) and dried with Na$_2$SO$_4$. The organics were filtered then concentrated under pressure to yield 1.58 g (93.4% yield) of an off-white crystalline solid (The AcOH salt of N-(2-oxo-2-(p-tolyl)ethyl)formamide which was used crude in the next reaction. 1H NMR (300 MHz, DMSO-d6) δ 11.96 (s, 1H), 8.16 (s, 1H), 7.89 (d, J=8.2 Hz, 2H), 7.35 (d, J=7.9 Hz, 2H), 4.64 (d, J=5.7 Hz, 2H), 2.39 (s, 3H).

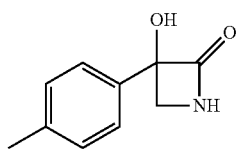

3-hydroxy-3-(p-tolyl)azetidin-2-one (2.13): In a 250 mL quartz round bottom flask, a solution of N-(2-oxo-2-(p-tolyl)ethyl)formamide·AcOH (100 mg, 0.42 mmol) in 30 mL ACN was degassed with argon. The flask was put into a UV reaction box fitted with 300 nm light bulbs and exposed to UV light for 2 h. The solution was concentrated under pressure to yield 70.4 mg (94.5% yield) of a yellow crystalline solid. 1H NMR (300 MHz, DMSO-d6) δ 8.19 (s, 1H), 7.33 (d, J=8.1 Hz, 2H), 7.18 (d, J=8.1 Hz, 2H), 6.60 (s, 1H), 3.4 (d, J=5.6 Hz, 1H), 3.36 (d, J=5.6 Hz, 1H), 2.29 (s, 3H).

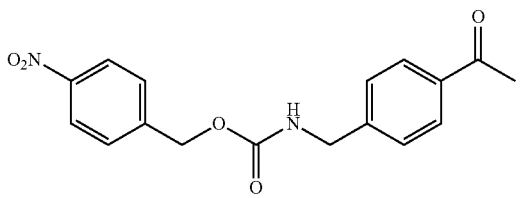 [SMILES: CC(=O)c1ccc(CNC(=O)OCc2ccc([N+](=O)[O-])cc2)cc1]

4-nitrobenzyl (4-acetylbenzyl)carbamate (2.16): To a solution of 2-(4-acetylphenyl)acetic acid (2 g, 11.2 mmol) in 60 mL Toluene was added diphenylphosphoryl azide (DPPA) (4.016 g, 14.6 mmol), triethylamine (TEA) (3.13 mL, 22.45 mmol) and (4-nitrophenyl)methanol (2.234 g, 14.6 mmol). The reaction flask was fitted with a reflux condenser and heated to reflux for 18 h. The solution was concentrated under pressure, dissolved in 60 mL of EtOAc then washed with 100 mL H$_2$O. The organics were dried with Na$_2$SO$_4$, filtered, and concentrated under pressure. The residue was run on a silica column (0-100% EtOAc in hexanes) to yield 770 mg (20.9% yield) of a yellow oil. Rf=0.2 in 50% EtOAc in hexanes. 1H NMR (300 MHz, Chloroform-d) δ 8.22 (d, J=8.4 Hz, 2H), 7.94 (d, J=7.8 Hz, 2H), 7.52 (d, J=8.1 Hz, 2H), 7.38 (d, J=7.8 Hz, 2H), 5.24 (s, 2H), 4.46 (d, J=6.0 Hz, 2H), 2.60 (s, 3H). [M+H]+=328+1=329.

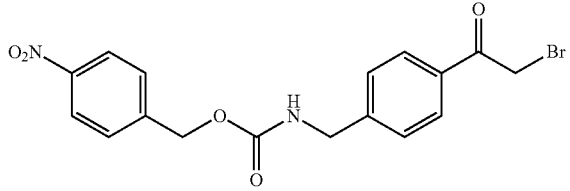 [SMILES: O=C(NCc1ccc(C(=O)CBr)cc1)OCc1ccc([N+](=O)[O-])cc1]

4-nitrobenzyl (4-(2-bromoacetyl)benzyl)carbamate (2.17): To a solution of CuBr2 (586 mg, 2.62 mmol) in 10 mL EtOAc was added a solution of 4-nitrobenzyl (4-acetylbenzyl)carbamate (430 mg, 1.31 mmol) in 10 mL chloroform. The reaction flask was fitted with a reflux condenser and heated to reflux for 18 h. The solution was cooled to 25° C., washed with 10 mL Sat. NaHCO$_3$(aq) and 10 mL Sat. NaCl (aq) then the organics were dried with Na$_2$SO$_4$. The organics were concentrated under pressure and used crude in the next reaction. NMR analysis showed a mixture of brominated product and starting material that were unable to be separated. [M+H]+=407+1=408.

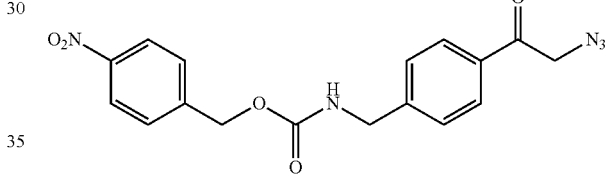

4-nitrobenzyl (4-(2-azidoacetyl)benzyl)carbamate (2.18): To a solution of impure 4-nitrobenzyl (4-(2-bromoacetyl)benzyl)carbamate (>1.31 mmol) in 7.5 mL ACN and 2.5 mL H$_2$O was added NaI (19.6 mg, 0.131 mmol) and NaN$_3$ (93.6 mg, 1.44 mmol). The reaction flask was fitted with a reflux condenser then stirred for 18 h at 60° C. The solution was cooled to 25° C. then diluted with water (10 mL) and extracted with EtOAc (3×10 mL). The organics were collected and dried with Na$_2$SO$_4$. The organics were filtered then concentrated under pressure and the residue was used crude in the next reaction. NMR analysis showed a mixture of 4-nitrobenzyl (4-acetylbenzyl)carbamate and 4-nitrobenzyl (4-(2-azidoacetyl)benzyl)carbamate that were unable to be separated.

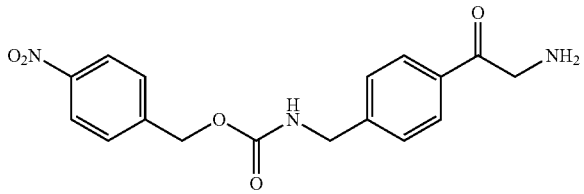 [SMILES: NCC(=O)c1ccc(CNC(=O)OCc2ccc([N+](=O)[O-])cc2)cc1]

4-nitrobenzyl (4-glycylbenzyl)carbamate (2.19): To a solution of impure 4-nitrobenzyl (4-(2-azidoacetyl)benzyl)carbamate (~0.655 mmol) in 20 mL THF was added PPh$_3$ (258 mg, 0.984 mmol) and p-toluenesulfonic acid·H$_2$O (PTSA) (374 g, 1.97 mmol). The reaction flask was fitted with a reflux condenser then heated to 40° C. for 18 h. The solution was cooled to room temperature and filtered to collect 86 mg (25.5% yield over the last 3 steps) of yellow solid (the PTSA salt of 4-nitrobenzyl (4-glycylbenzyl)carbamate). 1H NMR (300 MHz, DMSO-d6) b 8.25 (d, J=8.5 Hz, 2H), 7.99 (d, J=8.0 Hz, 2H), 7.62 (d, J=8.2 Hz, 2H), 7.08 (d, J=6.4 Hz, 2H), 5.20 (s, 2H), 4.58 (s, 2H), 4.32 (d, J=6.2 Hz, 2H). [M+H]+=343+1=345.

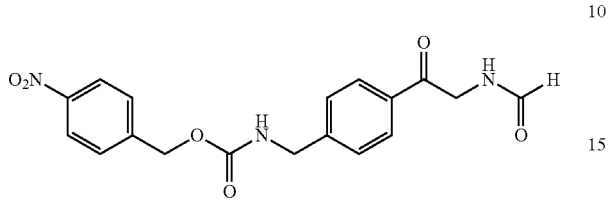

4-nitrobenzyl (4-(formylglycyl)benzyl)carbamate (2.20): To a flask of Ac$_2$O (473 µL, 5 mmol) fitted with a drying tube was added formic acid (201 µL, 5.34 mmol). The solution was headed to 60° C. while stirring for 2 h. The solution was cooled to 25° C. and 4-nitrobenzyl (4-glycylbenzyl) carbamate·PTSA (86 mg, 0.167 mmol) was added. The solution was stirred for 10 min. Sat. NaHCO$_3$(aq) (8.79 mL) was added dropwise. The solution was extracted with EtOAc (3×10 mL) then the organics were combined and dried with Na$_2$SO$_4$. The organics were filtered then concentrated under pressure to yield 45.9 mg (74% yield) of an off-yellow crystalline solid which was used crude in the next reaction. 1H NMR (300 MHz, DMSO-d6) δ 8.37 (s, 1H), 8.25 (d, J=8.3 Hz, 2H), 8.17 (s, 1H), 8.09 (t, J=6.1 Hz, 1H), 7.96 (d, J=8.4 Hz, 2H), 7.62 (d, J=8.3 Hz, 2H), 7.42 (d, J=8.0 Hz, 2H), 5.21 (s, 2H), 4.66 (d, J=5.7 Hz, 2H), 4.30 (d, J=6.2 Hz, 2H).

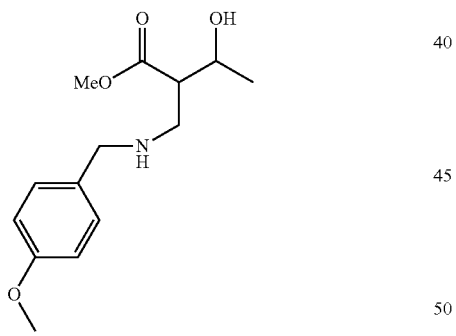

methyl 3-hydroxy-2-(((4-methoxybenzyl)amino)methyl) butanoate (2.23): To a solution of methyl 3-hydroxy-2-methylenebutanoate (2 g, 15.4 mmol) 48 in 20 mL of methanol (MeOH) was added (4-methoxyphenyl)methanamine (2.11 g, 15.4 mmol). The reaction was stirred at 25° C. for 48 h then concentrated under pressure. The residue was run on a silica column (isocratic 75% EtOAc in hexanes) to yield 3.991 g (97% yield) of a yellow oil. Rf=0.2 in 100% EtOAc. 1H NMR (300 MHz, Chloroform-d) δ 7.21 (d, J=8.5 Hz, 2H), 6.86 (d, J=8.4 Hz, 2H), 4.26-4.17 (m, 1H), 3.79 (s, 3H), 3.72 (s, 2H), 3.69 (s, 3H), 3.09-3.02 (m, 2H), 2.51-2.44 (m, 1H), 1.18 (d, J=6.2 Hz, 3H).

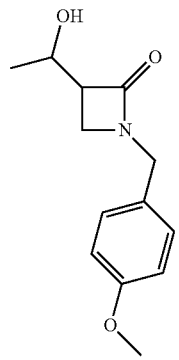 [SMILES: COc1ccc(CN2CC(C(C)O)C2=O)cc1]

3-(1-hydroxyethyl)-1-(4-methoxybenzyl)azetidin-2-one (2.24): To a 0° C. solution of methyl 3-hydroxy-2-(((4-methoxybenzyl)amino)methyl) butanoate (2.00 g, 7.48 mmol) in 15 mL dry THF was tert-butylmagnesium chloride (t-BMgCl) (14.96 mL of 2M in diethyl ether, 29.92 mmol). The solution was warmed to room temperature then stirred for 18 h. The solution was quenched with Sat. NH$_4$Cl (aq) then extracted with EtOAc (3×20 mL). The organics were dried with Na$_2$SO$_4$ then filtered. The organics were concentrated under pressure and the residue was run on a silica column (isocratic 100% EtOAc) to yield 1.264 g of a yellow oil. Rf=0.5 in 100% EtOAc. 1H NMR (300 MHz, Chloroform-d) δ 7.17 (d, J=8.8 Hz, 2H), 6.87 (d, J=8.7 Hz, 2H), 4.32 (q, J=14.9 Hz, 2H), 4.23-4.14 (m, 1H), 3.80 (s, 3H), 3.24-3.17 (m, 1H), 3.15 (d, J=4.1 Hz, 2H), 1.26 (d, J=6.4 Hz, 3H).

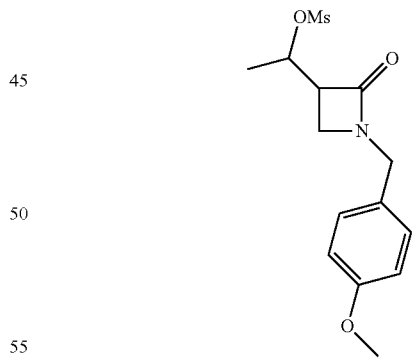

1-(1-(4-methoxybenzyl)-2-oxoazetidin-3-yl)ethyl methanesulfonate (2.25): To a solution of 3-(1-hydroxyethyl)-1-(4-methoxybenzyl)azetidin-2-one (1.264 g, 5.38 mmol) in 27 mL dichloromethane (DCM) was added MsCl (456 µL, 5.92 mmol) and triethylamine (TEA) (1.5 mL, 10.76 mmol). The solution was stirred at 25° C. for 2 h then diluted with 20 mL H$_2$O. The mixture was extracted with DCM (2×10 mL) then the organics were dried with Na$_2$SO$_4$, filtered, and concentrated under pressure to yield a yellow oil that was used crude in the next reaction.

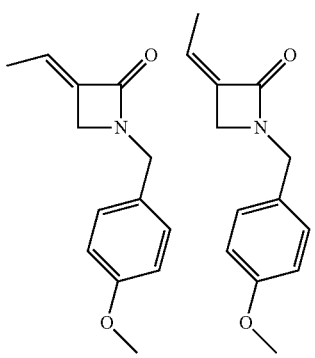

(E)-3-ethylidene-1-(4-methoxybenzyl)azetidin-2-one/
(Z)-3-ethylidene-1-(4-methoxybenzyl)azetidin-2-one
(2.26): To a solution of 1-(1-(4-methoxybenzyl)-2-oxoazetidin-3-yl)ethyl methanesulfonate (1.68 g, 5.38 mmol) in 27 mL toluene was added 1,8-Diazabicyclo[5.4.0]undec-7-ene (DBU) (1.19 mL, 7.69 mmol). The reaction vessel was fitted with a reflux condenser then stirred at 70° C. for 18 h. The solution was cooled to 25° C. then diluted with 20 mL H$_2$O. The mixture was extracted with EtOAc (3×20 mL) then the organics were dried with Na$_2$SO$_4$, filtered, and concentrated under pressure. The residue was run on a silica column (50-100% EtOAc in hexanes) to yield 1.0358 of a yellow oil. Rf=0.6 and 0.4 in 100% EtOAc). 1H NMR (300 MHz, Chloroform-d) δ 7.18 (d, J=8.7 Hz, 2H), 6.87 (d, J=8.7 Hz, 2H), 6.16 (qt, J=7.0, 1.6 Hz, 1H), 4.42 (d, J=3.0 Hz, 2H), 3.80 (s, 3H), 3.60 (dd, J=1.6, 0.8 Hz, 2H), 2.04 (d, J=7.1 Hz, 1H), 1.70 (d, J=7.0 Hz, 2H).

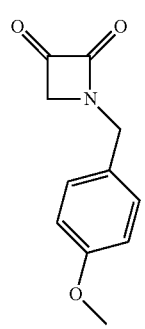

1-(4-methoxybenzyl)azetidine-2,3-dione (2.27): Ozone was bubbled through a mixture of E/Z-3-ethylidene-1-(4-methoxybenzyl)azetidin-2-one (250 mg, 1.15 mmol) dissolved in 10 mL MeOH and 5 mL DCM for 25 min. Me2S (84 μL, 1.15 mmol) was added to the solution under argon and the solution was stirred overnight at 25° C. The solution was concentrated under pressure and the residue was run on a silica column (50-100% EtOAc in hexanes) to yield 182.2 mg (77.3% yield) of a yellow oil. Rf=0.6 in 100% EtOAc. 1H NMR (300 MHz, Chloroform-d) b 7.21 (d, J=8.2 Hz, 2H), 6.91 (d, J=8.8 Hz, 2H), 4.71 (s, 2H), 3.81 (s, 3H), 3.76 (s, 2H).

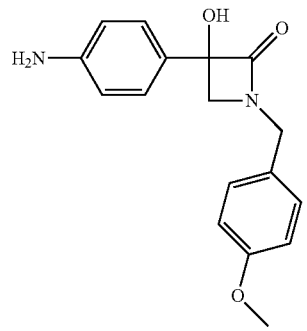 [SMILES: COc1ccc(CN2CC(O)(c3ccc(N)cc3)C2=O)cc1]

3-(4-aminophenyl)-3-hydroxy-1-(4-methoxybenzyl)azetidin-2-one (2.28): To a −78° C. solution of N-(4-bromophenyl)-1,1,1-trimethyl-N-(trimethylsilyl)silanamine (161 μL, 0.571 mmol) in 1 mL dry THF under argon was added n-BuLi (176 μL, 0.439 mmol). CeCl$_3$·7H$_2$O (204 mg, 0.549 mmol) was heated separately to 140° C. under vacuum then flushed with argon. The solution of N-(4-bromophenyl)-1,1,1-trimethyl-N-(trimethylsilyl)silanamine and n-BuLi was added to the CeCl$_3$ by cannula then stirred for 10 min. A separate solution of 1-(4-methoxybenzyl)azetidine-2,3-dione (90 mg, 0.439 mmol) in 1 mL dry THF under argon was added by cannula at −78° C. then the combined solutions were stirred at −78° C. for 1 h. The solution was quenched with dropwise addition of Sat. NH$_4$Cl (aq) until no gas evolved, then tetran-butylammonium fluoride (TBAF) (878 μL of 1M TBAF in H$_2$O, 0.878 mmol) was added dropwise while stirring. The mixture was stirred for 30 min then extracted with EtOAc (3×5 mL) and the organics were dried with Na$_2$SO$_4$, filtered, and concentrated under pressure. The residue was run on a silica column (0-100% EtOAc in hexanes) to yield 22.7 mg (17.3% yield) of a yellow oil. NMR analysis showed aniline coeluting with the product. Rf=0.2 in 50% EtOAc in hexanes. 1H NMR (300 MHz, Methanol-d4) δ 7.21 (d, J=8.3 Hz, 3H), 7.11 (d, J=8.5 Hz, 2H), 6.90 (d, J=8.6 Hz, 2H), 6.69 (d, J=8.4 Hz, 2H), 6.65 (d, J=8.4 Hz, 2H), 4.40 (s, 2H), 3.78 (s, 3H), 3.46 (d, J=5.6 Hz 1H), 3.39 (d, J=5.6 Hz 1H). [M+H]+=298+1=299.

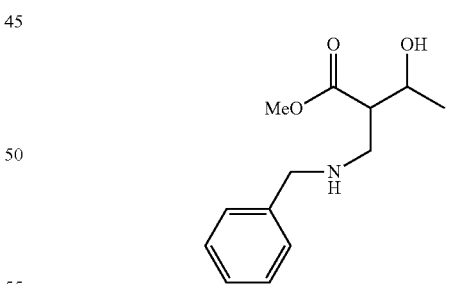

methyl 2-((benzylamino)methyl)-3-hydroxybutanoate (2.23'): To a solution of methyl 3-hydroxy-2-methylenebutanoate (3 g, 23 mmol) in 30 mL MeOH was added benzylamine (2.63 mL, 23 mmol). The reaction was stirred at 25° C. for 48 h then concentrated under pressure. The residue was run on a silica column (isocratic 80% EtOAc in hexanes) to yield 5.25 g (96% yield) of a yellow oil. Rf=0.4 in 50% EtOAc in hexanes. 1H NMR (300 MHz, Chloroform-d) δ 7.38-7.22 (m, 5H), 4.23 (p, J=6.3 Hz, 1H), 3.79 (s, 2H), 3.70 (s, 3H), 3.07 (qd, J=12.3, 5.5 Hz, 2H), 2.49 (td, J=6.7, 4.0 Hz, 1H), 1.19 (d, J=6.3 Hz, 3H).

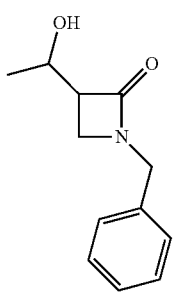

1-benzyl-3-(1-hydroxyethyl)azetidin-2-one (2.24'): To a 0° C. solution of methyl 2-((benzylamino)methyl)-3-hydroxybutanoate (5.25 g, 22.1 mmol) in 100 mL dry THF was tertbutylmagnesium chloride (t-BMgCl) (56.925 mL of 2M in diethyl ether, 28.46 mmol). The solution was warmed to room temperature then stirred for 18 h. The solution was quenched with Sat. NH$_4$Cl (aq) then extracted with EtOAc (3×100 mL). The organics were dried with Na$_2$SO$_4$ then filtered. The organics were concentrated under pressure and the residue was run on a silica column (0-100% EtOAc in hexanes) to yield 3.8 g (83.7% yield) of a yellow oil. Rf=0.2 in 50% EtOAc in hexanes. 1H NMR (300 MHz, Chloroform-d) δ 7.40-7.18 (m, 5H), 4.47-4.31 (m, 2H), 4.19 (d, J=6.5 Hz, 1H), 3.27-3.20 (m, 1H), 3.19 (d, J=4.4 Hz, 2H), 1.27 (d, J=6.3 Hz, 3H).

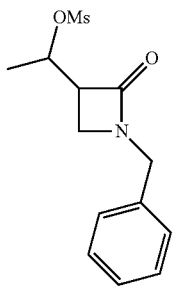 [SMILES: CC(OS(C)(=O)=O)C1CN(Cc2ccccc2)C1=O]

1-(1-benzyl-2-oxoazetidin-3-yl)ethyl methanesulfonate (2.25'): To a solution of 1-benzyl-3-(1-hydroxyethyl)azetidin-2-one (3.8 g, 18.5 mmol) in 93 mL dichloromethane (DCM) was added MsCl (1.56 mL, 20.4 mmol) and triethylamine (TEA) (5.15 mL, 37 mmol). The solution was stirred at 25° C. for 2 h then diluted with 10 mL H$_2$O. The mixture was extracted with DCM (2×100 mL) then the organics were dried with Na$_2$SO$_4$, filtered, and concentrated under pressure to yield a yellow oil that was used crude in the next reaction.

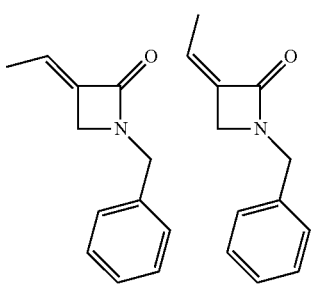

(E)-1-benzyl-3-ethylideneazetidin-2-one/(Z)-1-benzyl-3-ethylideneazetidin-2-one (2.26'): To a solution of 1-(1-benzyl-2-oxoazetidin-3-yl)ethyl methanesulfonate (5.24 g, 18.5 mmol) in 84 mL toluene was added 1,8-Diazabicyclo[5.4.0]undec-7-ene (DBU) (2.9 mL, 19.4 mmol). The reaction vessel was fitted with a reflux condenser then stirred at 70° C. for 18 h. The solution was cooled to 25° C. then diluted with 20 mL H$_2$O. The mixture was extracted with EtOAc (3×20 mL) then the organics were dried with Na$_2$SO$_4$, filtered, and concentrated under pressure. The residue was run on a silica column (0-100% EtOAc in hexanes) to yield 2.954 g (85% yield) of a yellow oil. 1H NMR (300 MHz, Chloroform-d) δ 7.39-7.21 (m, 5H), 6.22-6.12 (m, 1H), 4.49 (s, 2H), 3.63 (d, J=0.8 Hz, 2H), 2.05 (d, J=6.6 Hz, 1H), 1.70 (d, J=7.0 Hz, 2H).

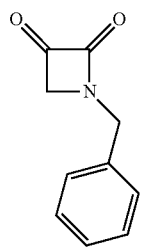 [SMILES: O=C1CN(Cc2ccccc2)C1=O]

1-benzylazetidine-2,3-dione (2.27'): Ozone was bubbled through a mixture of E/Z-1-benzyl-3-ethylideneazetidin-2-one (286.3 mg, 1.53 mmol) dissolved in 10 mL MeOH and 5 mL DCM for 25 min. Me2S (112.4 µL, 1.53 mmol) was added to the solution under argon and the solution was stirred overnight at 25° C. The solution was concentrated under pressure and the residue was run on a silica column (isocratic 75% EtOAc in hexanes) to yield 221.8 mg (83% yield) of a yellow oil. Rf=0.7 in 100% EtOAc. 1H NMR (300 MHz, Chloroform-d) δ 7.47-7.33 (m, 5H), 4.77 (s, 2H), 3.79 (s, 2H).

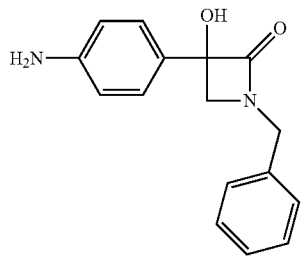 [SMILES: Nc1ccc(C2(O)CN(Cc3ccccc3)C2=O)cc1]

3-(4-aminophenyl)-1-benzyl-3-hydroxyazetidin-2-one (2.28'): To a −78° C. solution of N-(4-bromophenyl)-1,1,1-trimethyl-N-(trimethylsilyl)silanamine (431 µL, 1.36 mmol) in 2 mL dry THF under argon was added n-BuLi (419 µL, 1.048 mmol). CeCl$_3$·7H$_2$O (488 mg, 1.31 mmol) was heated separately to 140° C. under vacuum then flushed with argon. The solution of N-(4-bromophenyl)-1,1,1-trimethyl-N-(trimethylsilyl)silanamine and n-BuLi was added to the CeCl$_3$ by 2-0 cannula then stirred for 10 min. A separate solution of 1-benzylazetidine-2,3-dione (183.4 mg, 1.048 mmol) in 2 mL dry THF under argon was added by cannula at −78° C. then the combined solutions were stirred at −78° C. for 1 h. The solution was quenched with dropwise addition of Sat. NH$_4$Cl (aq) until no gas evolved, then tetra-n-butylammonium fluoride (TBAF) (2.096 mL of 1M TBAF in H₂O, 2.096 mmol) was added dropwise while stirring. The mixture was stirred for 30 min then extracted with EtOAc (3×5 mL) and the organics were dried with Na₂SO₄, filtered, and concentrated under pressure. The residue was run on a silica column (0-100% EtOAc in hexanes) to yield 55 mg (19.58% yield) of a yellow oil. 1H NMR (300 MHz, Methanol-d4) δ 7.42-7.26 (m, 5H), 7.22 (d, J=8.5 Hz, 2H), 6.70 (d, J=8.7 Hz, 2H), 4.48 (s, 2H), 3.50 (d, J=5.5, 1H), 3.43 (d, J=5.5, 1H). [M+H]+=268+1=269.

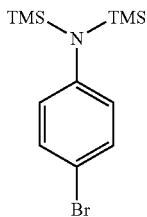 [SMILES: C[Si](C)(C)N(c1ccc(Br)cc1)[Si](C)(C)C]

N-(4-bromophenyl)-1,1,1-trimethyl-N-(trimethylsilyl)silanamine (2.30): To a −78° C. solution of 4-bromoaniline (1 g, 5.81 mmol) in 25 mL dry THF was added n-BuLi (4.65 mL of 2M n-BuLi in THF, 11.6 mmol) dropwise. The solution was stirred for 1 h then TMS-Cl (1.695 mL, 13.3 mmol) was added dropwise. The solution was allowed to raise to 25° C. and stirred overnight. The solution was concentrated under light vacuum to only remove the THF, then a syringe filter was used to remove any residual solid, leaving 1.64 mL (63.3% yield) of product. 1H NMR (300 MHz, Chloroform-d) δ 7.30 (d, J=8.5 Hz, 2H), 6.75 (d, J=8.6 Hz, 2H), 0.05 (s, 18H).

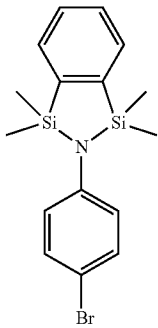

2-(4-bromophenyl)-1,1,3,3-tetra methyl-2,3-dihydro-1H-benzo[c][1,2,5]azadisilole (2.31): To a solution of 4-bromoaniline (510 mg, 3 mmol) in 2.5 mL toluene was added (Ph₃P)₃RhCl (5 mg, 0.0054 mmol) and 1,2-bis(dimethylsilyl)benzene (738 mg, 3.8 mmol). The reaction flask was fitted with a reflux condenser and heated to reflux while stirring overnight. The solution was cooled to room temperature, then diluted with 2 mL of 50/50 hexanes/EtOAc as well as 2 m of phosphate buffer (0.1M sodium phosphate in H₂O, pH=7). The organics were separated and concentrated under pressure. The residue was recrystallized by dissolving it in a minimum of 50/50 hexanes/EtOAc then cooling in the −2° C. freezer for 1 h, followed by filtration to yield 698.9 mg (64.5% yield) of product. 1H NMR (300 MHz, Chloroform-d) δ 7.64-7.58 (m, 2H), 7.45 (dd, J=5.4, 3.2 Hz, 2H), 7.37 (d, J=8.7 Hz, 2H), 6.91 (d, J=8.8 Hz, 2H), 0.38 (s, 12H).

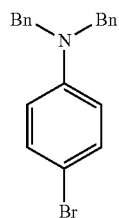

N,N-dibenzyl-4-bromoaniline (2.32): To a solution of 4-bromoaniline (1.5 g, 8.72 mmol) in 15 mL dimethylformamide (DMF) was added K₂CO₃ (2.41 g, 17.44 mmol) and benzyl bromide (4.47 g, 26.16 mmol). The reaction flask was fitted with a reflux condenser then heated to 110° C. overnight while stirring. The solution was cooled to room temperature, diluted with 10 mL H₂O then extracted with EtOAc (3×20 mL). The organics were combined, dried with Na₂SO₄, filtered, and concentrated under pressure. The residue was run on a silica column (100% hexanes) and the Rf=0.2, 0.3, and 0.4 spots (100% hexanes) were combined and recrystallized in an ice bath from a minimum volume of EtOAc/hexanes to yield 1.0816 g (35.3% yield) of a yellow oil. 1H NMR (300 MHz, Chloroform-d) δ 7.38-7.26 (m, 7H), 7.23 (dd, J=7.4, 5.1 Hz, 5H), 6.59 (d, J=9.1 Hz, 2H), 4.63 (s, 4H).

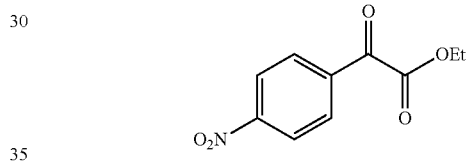

ethyl 2-(4-nitrophenyl)-2-oxoacetate (2.39): To a solution of ethyl 3-(4-nitrophenyl)-3-oxopropanoate (5.0 g, 21.08 mmol) in 25 mL AcOH was added CuBr (302 mg, 21.08 mmol) and TEMPO (6.59 g, 42.16 mmol). The reaction flask was fitted with a reflux condenser and the mixture was heated to 100° C. while stirring for 18 h. The mixture was cooled to room temperature then diluted with 50 mL H₂O then Sat. NaHCO₃(aq) was added until the AcOH was neutralized. The aqueous later was extracted with DCM (3×100 mL) then the organics were combined, dried with Na₂SO₄, filtered, and concentrated under pressure. The residue was run on a silica column (0-50% EtOAc in hexanes) to yield 1.495 g (31.7% yield) of a yellow oil. 1H NMR (500 MHz, DMSO-d6) δ 8.39 (d, J=8.8 Hz, 2H), 8.24 (d, J=8.9 Hz, 2H), 4.42 (q, J=7.1 Hz, 2H), 1.34 (t, J=7.1 Hz, 3H). 13C NMR (126 MHz, DMSO-d6) δ 184.35, 161.69, 150.67, 137.08, 131.42, 123.92, 62.63, 13.80.

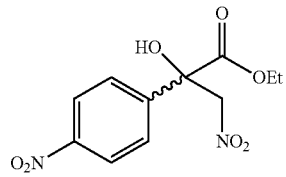 [SMILES: CCOC(=O)C(O)(C[N+](=O)[O-])c1ccc([N+](=O)[O-])cc1]

ethyl 2-hydroxy-3-nitro-2-(4-nitrophenyl)propanoate (2.40): To a solution of ethyl 2-(4-nitrophenyl)-2-oxoacetate (1.25 g, 5.61 mmol) in 40 mL THF was added MeNO₂ (6.07 mL, 112 mmol) and 1,2,3,4-tetrahydro-1,1'-biisoquinoline (145 mg, 0.561 mmol). The solution was stirred at 25° C. for 18 h then concentrated under pressure. The residue was run on a silica column (0-40% EtOAc in hexanes) to yield 1.55 g (97.2% yield) of a yellow oil. Rf=0.25 in 20% EtOAc in hexanes). 1H NMR (500 MHz, DMSO-d6) δ 8.27 (d, J=9.0 Hz, 2H), 7.85 (d, J=9.0 Hz, 2H), 7.23 (d, J=0.8 Hz, 1H), 5.60 (dd, J=13.6, 0.9 Hz, 1H), 5.02 (d, J=13.6 Hz, 1H), 4.20 (qd, J=7.1, 1.1 Hz, 2H), 1.19 (t, J=7.1 Hz, 3H). 13C NMR (126 MHz, DMSO-d6) δ 170.17, 147.50, 145.50, 127.17, 123.44, 81.30, 76.44, 62.14, 13.72. [M+H]+=284+1=285.

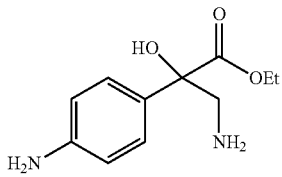 [SMILES: CCOC(=O)C(O)(CN)c1ccc(N)cc1]

ethyl 3-amino-2-(4-aminophenyl)-2-hydroxypropanoate (2.41): To a solution of ethyl 2-hydroxy-3-nitro-2-(4-nitrophenyl)propanoate (1.45 g, 5.1 mmol) in 25 mL MeOH was added PTSA·$H_2O$ (1.068 g, 5.62 mmol) and Pd/C (145 mg). The solution was put in a parr shaker and 45 psi of $H_2$ gas was applied for 18 h. The solution was degassed with argon then filtered through celite. The solution was put onto a DEAE Sepharaose Fast Flow Anion Exchange Resin column (~0.11 mmol/mL of resin) and eluted with an excess of EtOH to yield 1.16 g of a yellow solid. NMR analysis shows some PTSA still left but the material was used in the next reaction. 1H NMR (500 MHz, DMSO-d6) δ 7.12 (d, J=8.6 Hz, 2H), 6.59 (s, 1H), 6.56 (d, J=8.7 Hz, 2H), 4.13 (dd, J=7.1, 3.6 Hz, 2H), 3.40 (d, J=13.1 Hz, 1H), 3.06 (d, J=13.0 Hz, 1H), 1.17 (t, J=7.0 Hz, 3H). [M+H]+=224+1=225.

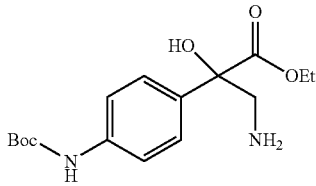 [SMILES: CCOC(=O)C(O)(CN)c1ccc(NC(=O)OC(C)(C)C)cc1]

ethyl 3-amino-2-(4-((tert-butoxycarbonyl)amino)phenyl)-2-hydroxypropanoate (2.42): To a solution of ethyl 3-amino-2-(4-aminophenyl)-2-hydroxypropanoate (1.066 g, 4.76 mmol) in a solution of 50 mL 10% AcOH in water and 50 mL 1,4-dioxane was added $Boc_2O$ (1.09 g, 4.998 mmol) and the mixture was stirred at 25° C. overnight. The reaction was quenched with Sat. $NaHCO_3$(aq) then extracted with DCM (3×50 mL). The organics were dried with $Na_2SO_4$, filtered, and concentrated under pressure. The residue was run on a silica column (0-20% MeOH in DCM) to yield 675.6 mg (44% yield) of a yellow oil. Rf=0.2 in 25% MeOH in DCM. 1H NMR (300 MHz, Methanol-d4) δ 7.50-7.36 (m, 4H), 3.30 (d, J=13.0 Hz, 1H), 2.95 (d, J=13.4 Hz, 1H), 1.51 (s, 9H). 13C NMR (126 MHz, DMSO-d6) δ 172.02, 152.75, 138.86, 134.21, 125.71, 117.73, 79.01, 78.51, 60.82, 49.87, 28.10, 13.94. [M+H]+=324+1=325

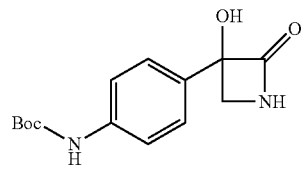 [SMILES: CC(C)(C)OC(=O)Nc1ccc(C2(O)CNC2=O)cc1]

tert-butyl (4-(3-hydroxy-2-oxoazetidin-3-yl)phenyl)carbamate (2.43): To a 0° C. solution of ethyl 3-amino-2-(4-((tert-butoxycarbonyl)amino)phenyl)-2-hydroxypropanoate (116 mg, 0.358 mmol) in 5 mL dry THF was added tert-butylmagnesium chloride (2.15 mL of 1.0 M in THF solution, 2.15 mmol). The solution was allowed to warm to 25° C. then stirred for 90 h. The reaction was quenched with Sat. $NH_4Cl$ (aq) then the mixture was extracted with EtOAc (3×10 mL). The combined organics were dried with $Na_2SO_4$, filtered, then concentrated under pressure. The residue was run on a silica column (0-100% EtOAc in hexanes) to yield 18.7 mg (22% yield) of a yellow oil. Rf=0.2 in 70% EtOAc in hexanes). 1H NMR (300 MHz, Methanol-$d_4$) δ 7.45 (s, 4H), 3.59 (d, J=5.6, 1H), 3.54 (d, J=5.6, 1H), 1.54 (s, 9H). [M+H]+=278+1=279.

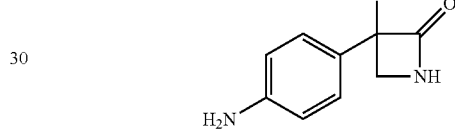

3-(4-aminophenyl)-3-hydroxyazetidin-2-one (2.44): To a solution of tert-butyl (4-(3-hydroxy-2-oxoazetidin-3-yl)phenyl)carbamate (6.9 mg, 0.0248 mmol) in 500 μL DCM was added dry TFA (38 μL, 0.496 mmol). The solution was stirred & for 3 h at 25° C. then concentrated under pressure to yield a quantitative amount of a yellow oil. 1H NMR (500 MHz, DMSO-d6) δ 8.24 (5, 1H), 7.42 (d, J=8.5 Hz, 2H), 7.12 (d, J=8.2 Hz, 2H), 3.41 (d, J=5.7, 1H), 3.37 (d, J=5.7, 1H). 13C NMR (126 MHz, DMSO-d6) δ 170.44, 126.42, 120.18, 86.24, 52.94. COSY, HSQC, and HMBC correlations in TABLE 4. [M+H]+=178+1=179.

TABLE 4

| 2D NMR correlations for compound 2.44. 2D Assignments | | | | |
|---|---|---|---|---|
| Atom | δ (ppm) | COSY | HSQC | HMBC |
| 1 C | 120.25 | | 1 | 3 |
| H | 7.12 | 6 | 1 | 3, 5 |
| 2 C | | | | |
| 3 C | 120.25 | | 3 | 1 |
| H | 7.12 | 4 | 3 | 1, 5 |
| 4 C | 126.46 | | 4 | 6 |
| H | 7.42 | 3 | 4 | 5, 6, 8 |
| 5 C | 142.15 | | | 1, 3, 4, 6, 9', 9" |
| 6 C | 126.46 | | 6 | 4 |
| H | 7.42 | 1 | 6 | 4, 5, 8 |
| 7 N | | | | |
| H2 | | | | |
| 8 C | 85.46 | | | 4, 6, 9', 9" |
| 9 C | 42.88 | | 9', 9" | 10 |
| H' | 3.41 | 9" | 9 | 5, 8, 11 |
| H" | 3.37 | 9' | 9 | 5, 8, 11 |
| 10 N | | | | |

TABLE 4-continued

2D NMR correlations for compound 2.44.

| Atom | δ (ppm) | COSY | HSQC | HMBC |
|---|---|---|---|---|
| H | 8.24 | | | 9 |
| 11 C | 170.43 | | | 9', 9" |
| 12 O | | | | |
| H | | | | |
| 13 O | | | | |

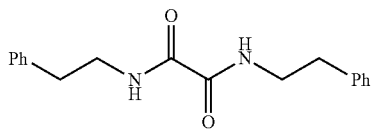 [SMILES: O=C(NCCc1ccccc1)C(=O)NCCc1ccccc1]

N1,N2-diphenethyloxalamide (2.47): To a solution of 2-phenylethan-1-amine (20 g, 165 mmol) in 80 mL ethanol (EtOH) was added diethyl oxalate (11.2 mL, 82.5 mmol) in 15 ml EtOH dropwise. The mixture was stirred at 25° C. for 4 h then concentrated under pressure. The residue was washed with cold hexanes and filtered to yield 23.384 g (95.1% yield) of a white crystalline solid. 1H NMR (300 MHz, Chloroform-d) δ 7.36-7.16 (m, 10H), 3.57 (q, J=7.1 Hz, 4H), 2.86 (t, J=7.2 Hz, 4H)

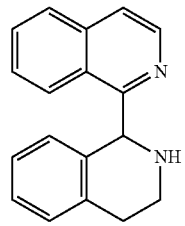 [SMILES: c1ccc2c(c1)CCNC2c1nccc2ccccc12]

1,2,3,4-tetrahydro-1,1'-biisoquinoline (2.48): To N1,N2-diphenethyloxalamide (3.57 g, 12.07 mmol) was added 24.27 mL of polyphosphoric acid. The reaction flask was fitted with a reflux condenser and the mixture was heated to 190° C. while stirring for 18. The mixture was cooled to 25° C. and diluted with 30 mL H$_2$O then 10% NaOH in H$_2$O was added until the pH=(approx. 450 mL). The mixture was extracted with DCM (4×50 mL) then the combined organics were dried with Na$_2$SO$_4$, filtered, and concentrated under pressure. The residue was recrystallized from a minimum of EtOAc to yield 2.265 g (72% yield) of a white powder. 1H NMR (300 MHz, Chloroform-d) δ 8.44 (d, J=5.7 Hz, 1H), 8.28 (d, J=8.5 Hz, 1H), 7.92 (d, J=8.1 Hz, 1H), 7.82-7.66 (m, 3H), 7.24-7.18 (m, 2H), 7.00 (t, J=7.2 Hz, 1H), 6.65 (d, J=7.9 Hz, 1H), 6.43 (s, 1H), 3.74-3.59 (m, 2H), 3.31 (ddd, J=14.4, 9.1, 5.3 Hz, 1H), 3.16 (dt, J=16.6, 5.1 Hz, 1H).

Example 2: Folate Biosynthetic Enzymes

The activity of four enzymes from the folate biosynthetic pathway in *E. coli* was reconstituted in vitro using purified recombinant proteins. 7,8-Dihydro-6-hydroxymethylpterinpyrophosphokinase (HPPK), dihydropteroate synthase (DHPS), and dihydrofolate reductase (DHFR) were successfully used to chemoenzymatically incorporate 3-(para-NH$_2$-phenyl)-3-HβL into the folate biosynthetic pathway without inhibiting flux through these steps. An assay for measuring real time dihydrofolate synthetase (DHFS) rates was developed using a coupled enzyme assay with pyruvate kinase (PK) and lactate dehydrogenase (LDH) to convert ADP and PEP to ATP and pyruvate, respectively, with consumption of NADH during the subsequent reduction of pyruvate to lactate.

Introduction

Synthesis and incorporation of the 3-HβL warhead into the PABA analog 3-(para-NH$_2$-phenyl)-3-HβL allowed for testing of the general hypothesis that the 3-HβL warhead can act as a transition state inhibitor of dihydrofolate synthetase (DHFS). DHFS was strategically selected as the enzyme target for inhibition as it comes from the superfamily of ATP-dependent carboxylateamine ligases. Similar to glutamine synthetase, these enzymes convert a carboxylic acid to the corresponding acyl phosphate via phosphate transfer from ATP. The acyl phosphate is then captured by a nucleophile, L-Glu for DHFS, resulting in the release of ADP, Pi, and the amide product. Inhibition of DHFS by a 3-HβL transition state mimetic would represent the first demonstration that the 3-HβL warhead can serve as a general pharmacophore for inhibiting enzymes in this superfamily. To date, tabtoxinine-β-lactam from *P. syringae* is the only known 3-HβL inhibitor of glutamine synthetase. The 3-hydroxy group of the 3-HβL of tabtoxinine-β-lactam is phosphorylated in the GS active site generating a non-covalent, tight-binding transition state inhibitor. It was hypothesized that incorporation of 3-(para-NH$_2$-phenyl)-3-HβL into the folate scaffold may generate a compound capable of the same conversion to a transition state inhibitor in the DHFS active site.

Figure 14:
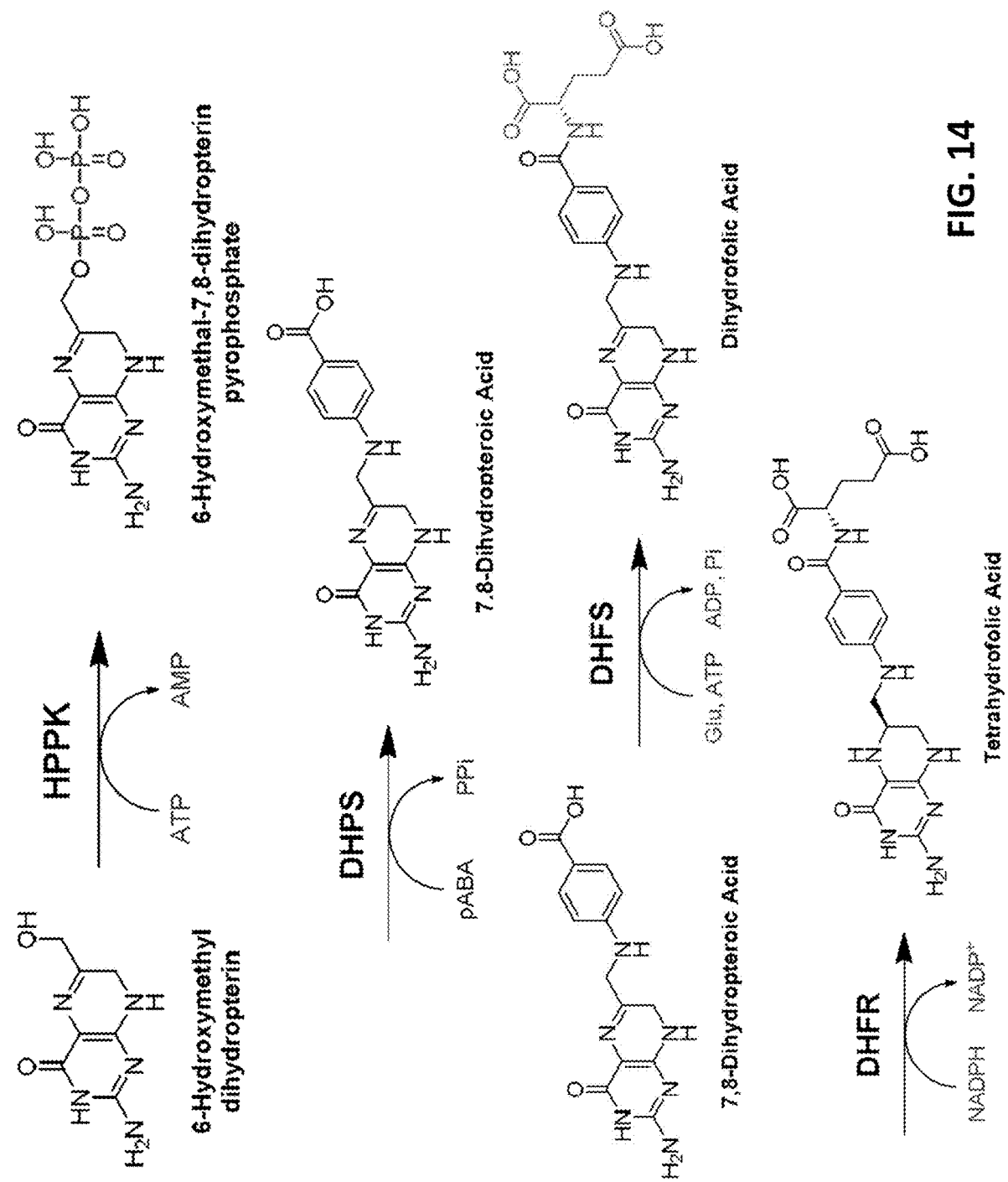
FIG. 14 is a schematic showing four enzyme folate biosynthetic sequence for the conversion of 6-Hydroxymethyl dihydropterin to Tetrahydrofolic acid in accordance with the present disclosure.

To test this hypothesis, in vitro enzyme assays were established that reconstitute the DHFS biosynthetic reaction. The entire folate biosynthetic pathway is comprised of nine enzymes, but only a subset of these enzymes is closely involved in making dihydrofolic acid and tetrahydrofolic acid. To this end, the 4-enzyme sequence in FIG. 14 was examined. 7,8-dihydro-6-hydroxymethylpterinpyrophosphokinase (HPPK), which catalyzes the di-phosphorylation of 6-hydroxymethyldihydropterin, combines with dihydropteroate synthase (DHPS), which catalyzes the addition of p-amino-benzoic acid (PABA) to 6-hydroxymethyl-7,8-dihydropterin pyrophosphate (HPP), to produce 7,8-dihydropteroic acid (7,8-DHP). It is this 7,8-dihydropteroic acid is one of the main substrates of dihydrofolate synthetase (DHFS), which catalyzes the condensation with L-glutamate onto the benzoic acid group of 7,8-DHP5 in an ATP dependent manner (see e.g., FIG. 14). Dihydrofolate reductase (DHFR) then reduces the N—C bond in the B ring of the pterin moiety in an NADPH dependent manner (see e.g., FIG. 14). Herein is described the investigation of these four enzymes (HPPK, DHPS, DHFS, and DHFR), the results of which lead to the chemoenzymatic production of potential inhibitors of DHFS, and an assay capable of measuring DHFS activity.

DHFS and 7,8-DHP

Figure 15:
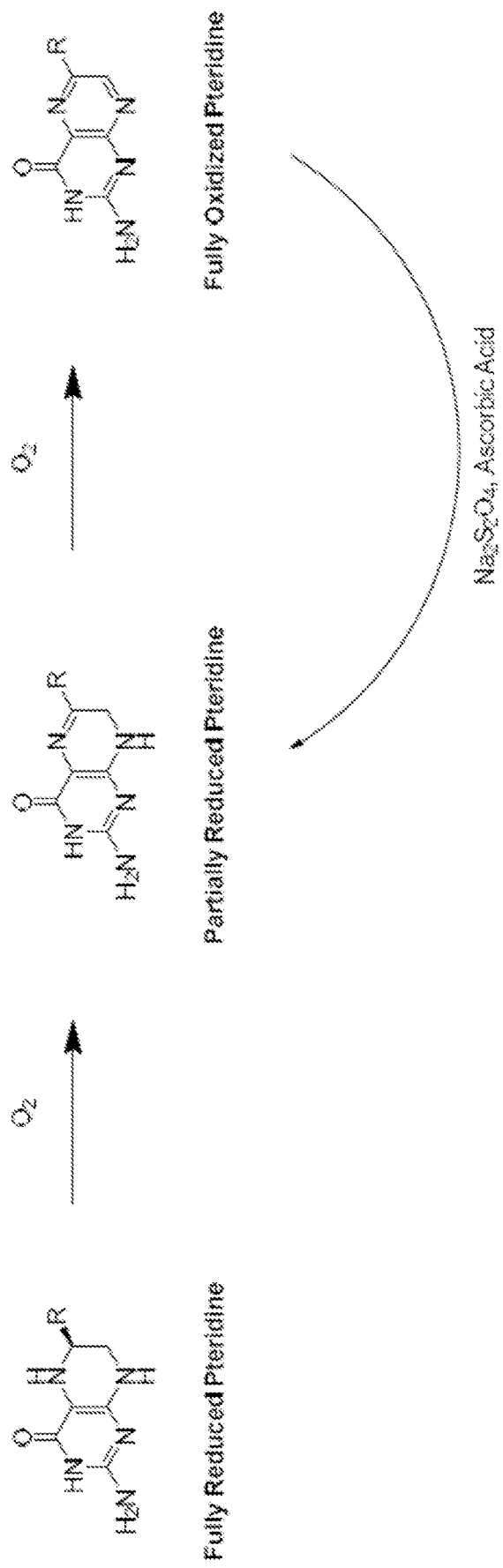
FIG. 15 is a schematic showing the oxidation and reduction of pteridine ring systems in accordance with the present disclosure.

It was possible to purchase pure 7,8-dihydropteroic acid as late as 2010, as there are studies of folate biosynthetic enzymes that utilized pure 7,8-DHP, but the specialized company that produces pteridines suitable for biochemical assays (Schircks Laboratories) discontinued production of pure 7,8-DHP. Endemic to biological pteridines suitable for biochemical assays is the atmospheric oxidation pathway exemplified in FIG. 15. This oxidation happens readily in regular laboratory atmosphere, and all partially reduced pterin rings are stored in inert atmosphere boxes then kept under as much inert atmosphere as possible when used. DHFS does not readily use pteridines that are not in the correct oxidation state as substrates. This oxidation can be partially reversed using sodium dithionite and L-ascorbic acid, allowing the purchase and storage of the inert pteroic acid and chemical reduction prior to use. However, the ascorbate necessary for reduction inhibits the enzyme lactate dehydrogenase, and separating the ascorbate from the newly formed 7,8-DHP takes time during which the 7,8-DHP re-oxidizes. This re-oxidation is so quick that inconsistency in concentration of 7,8-DHP from batch-to-batch may compromise the reproducibility of DHFS activity in assays.

Figure 16:
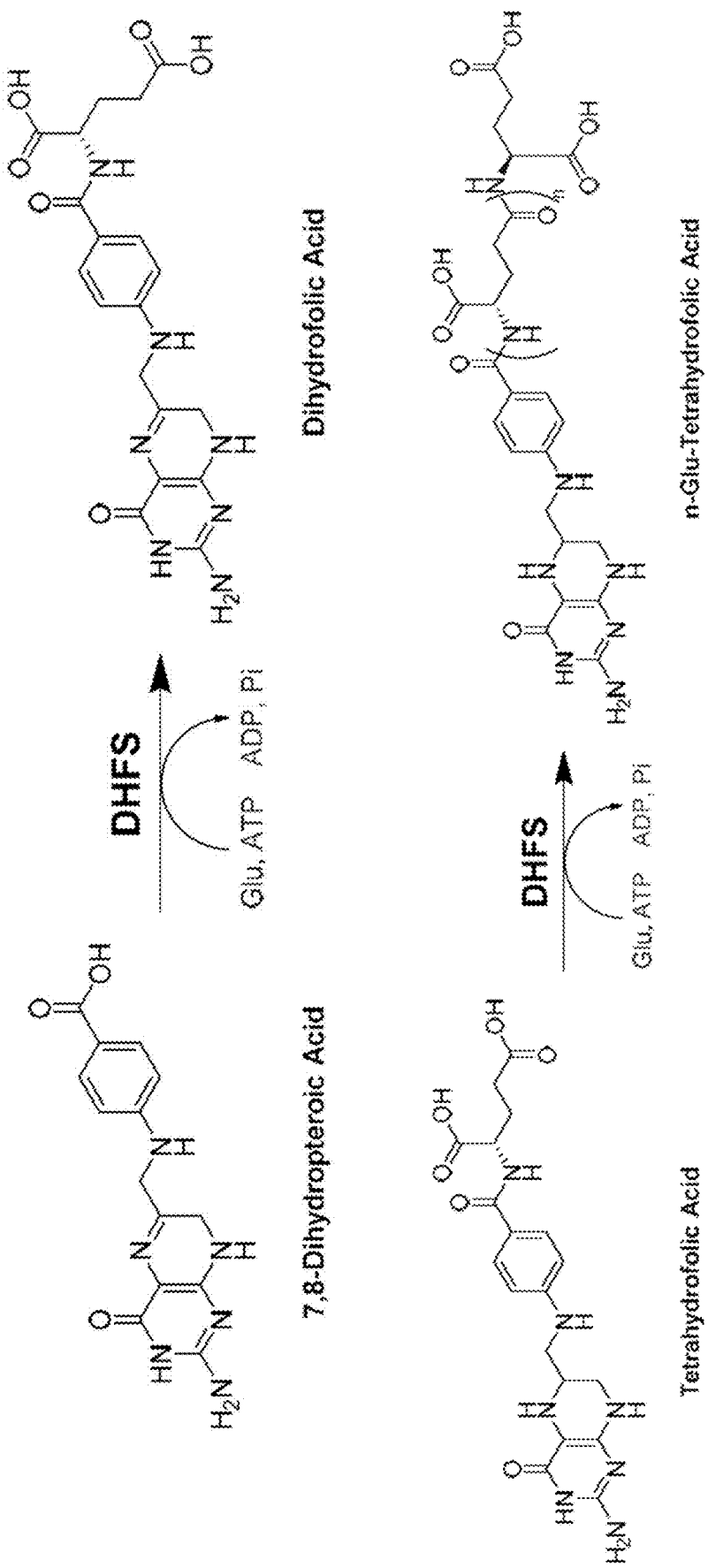
FIG. 16 is a schematic showing DHFS-catalyzed reactions leading to the single and poly-glutamylation of 7,8-DHP and THFA, respectively, in accordance with the present disclosure.

Therein lies the two problems that were the impetus for the work described herein: 1) 7,8-DHP cannot be readily synthesized in sufficient purity for reproducible assays; 2) 7,8-DHP cannot be purchased and stored in inert atmosphere conditions until use. However, tetrahydrofolic acid (THFA) is commercially available, providing a potential solution. *E. coli* uses DHFS to add a single glutamate to 7,8-DHP, but also uses DHFS to add multiple glutamates to the terminal carboxylic acid moieties of THFA (see e.g., FIG. 16), in a process which gives DHFS its second name: folylpolyglutamate synthetase. As such, it is not necessary to use 7,8-DHP as the substrate for DHFS when THFA is available. While also vulnerable to the same atmospheric oxidation that 7,8-DHP is, it is possible to purchase large enough quantities of THFA that is stored under inert atmosphere until use.

HPPK, DHPS, and DHFR

Owing to the atmospheric oxidation problem described above, the production of a potential inhibitor using a biologically similar pterin moiety and the 3-HβL synthesized herein may run into a pitfall of pterin oxidation states. However, the 3-HβL synthesized herein was purposely designed to be a structural mimic of PABA, and DHPS is well known to have a very accommodating active site. DHPS catalyzes N-alkylation of sulfonamide antibiotics with HPP to generate the pterin-sulfonamide adduct with loss of PPi. It is this pterin-sulfonamide adduct that inhibits DHPS and downstream folate biosynthesis. If HPPK and DHPS are harnessed to chemoenzymatically synthesize a pterin-3-HβL using the biological pterin donor molecule HPP, then a potential inhibitor may be made in situ then used immediately (a prodrug strategy). In order to investigate this possibility, the following questions were asked about the HPPK/DHPS system: 1) Can pure 6-hydroxymethyl-7,8-dihydropterin be phosphorylated then ligated to PABA in a biochemical setting? 2) Can DHPS use a 3-HβL instead of PABA as a substrate? 3) If DHPS can assemble the 3-HβL-pterin compound, how fast does it do this chemistry compared to its natural process of PABA-pterin ligation?

Figure 17:
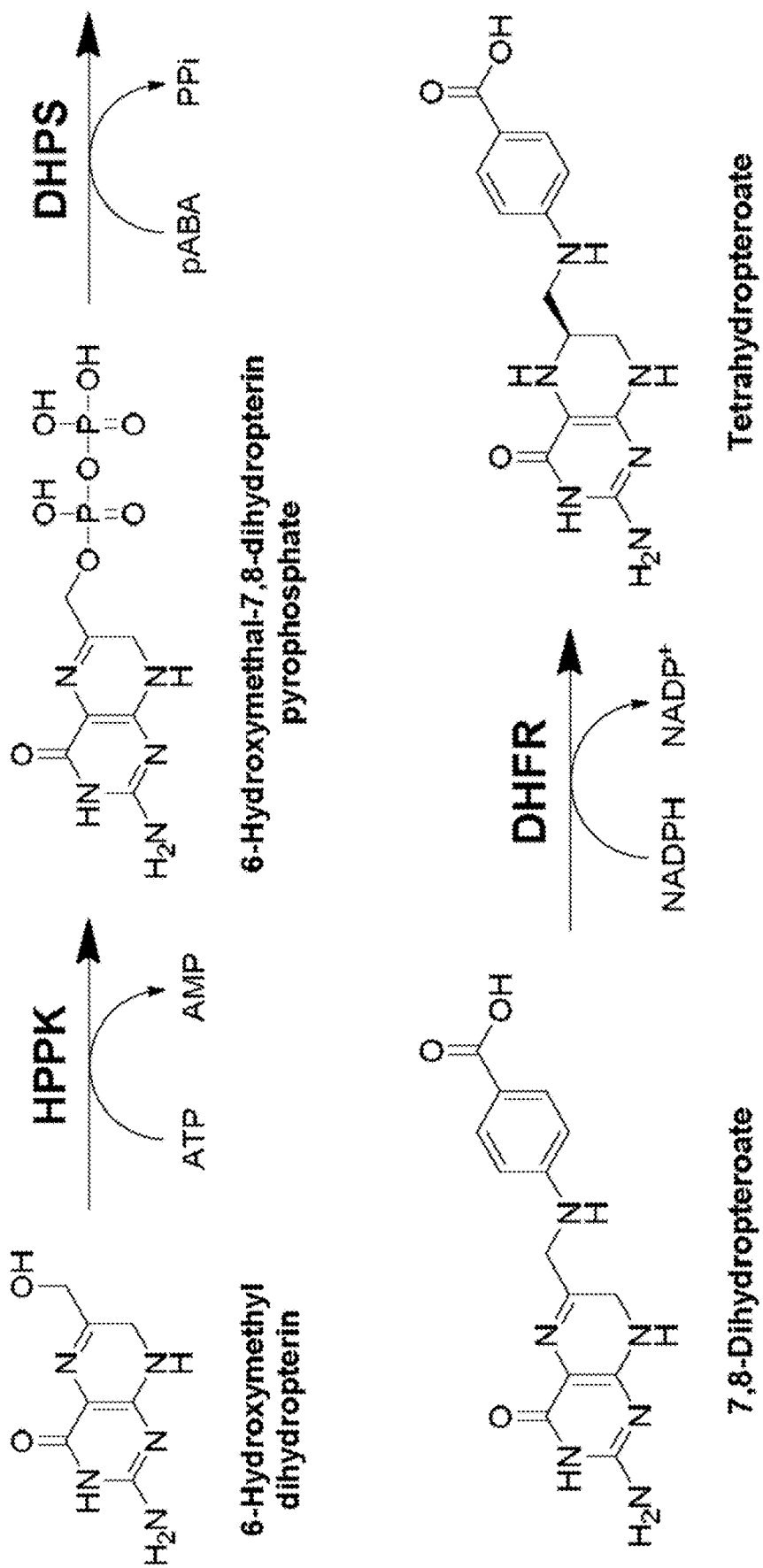
FIG. 17 is a schematic showing three enzyme sequence for determining steady state kinetics for DHPS by measuring optical absorbance at 340 nm (NADPH consumption) in accordance with the present disclosure.
Figure 18:
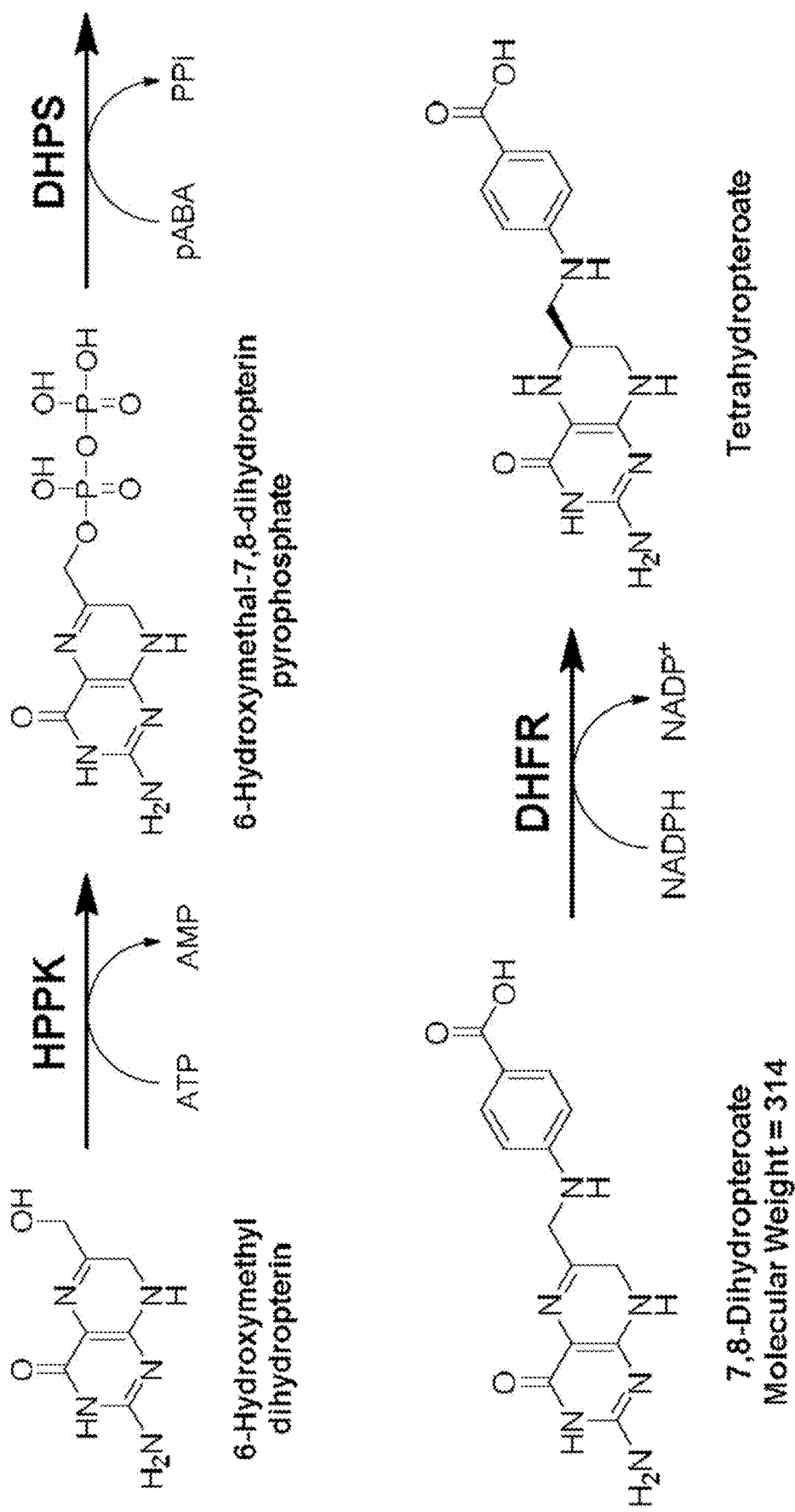
FIG. 18 is a schematic showing the three-enzyme sequence for the potential production of a 3-HβL-pterin adduct produced by DHPS, and detection of the 3-HβL-pterin product by DHFR-catalyzed consumption of NADPH in accordance with the present disclosure.

Fernley, Iliades, and Macreadie developed an assay in 2006 to measure DHPS steady-state kinetic activity by coupling DHFR activity to the reaction catalyzed by HPPK and DHPS (see e.g., FIG. 17). These methods were adapted herein. The rapid reduction of the pterin moiety by DHFR after DHPS action resulted in a reproducible decrease in absorbance at 340 nm over time (as NADPH was oxidized to NADP$^+$). DHFR would only reduce dihydropteroic acid, not 6-hydroxymethyl-7,8-dihydropterin, and as long as the DHFR rate was not slower than the DHPS rate, then the rate limiting step of DHPS is represented by the decrease in absorbance at 340 nm overtime. Removal of enzymes via filtration through a molecular weight cutoff (MWCO) filter and analysis of the reaction mixtures by LC-MS confirm production of both 7,8-DHP and the desired pterin-3-HβL product (see e.g., FIG. 18).

Steady-State Determination of DHFS Activity

Figure 19:
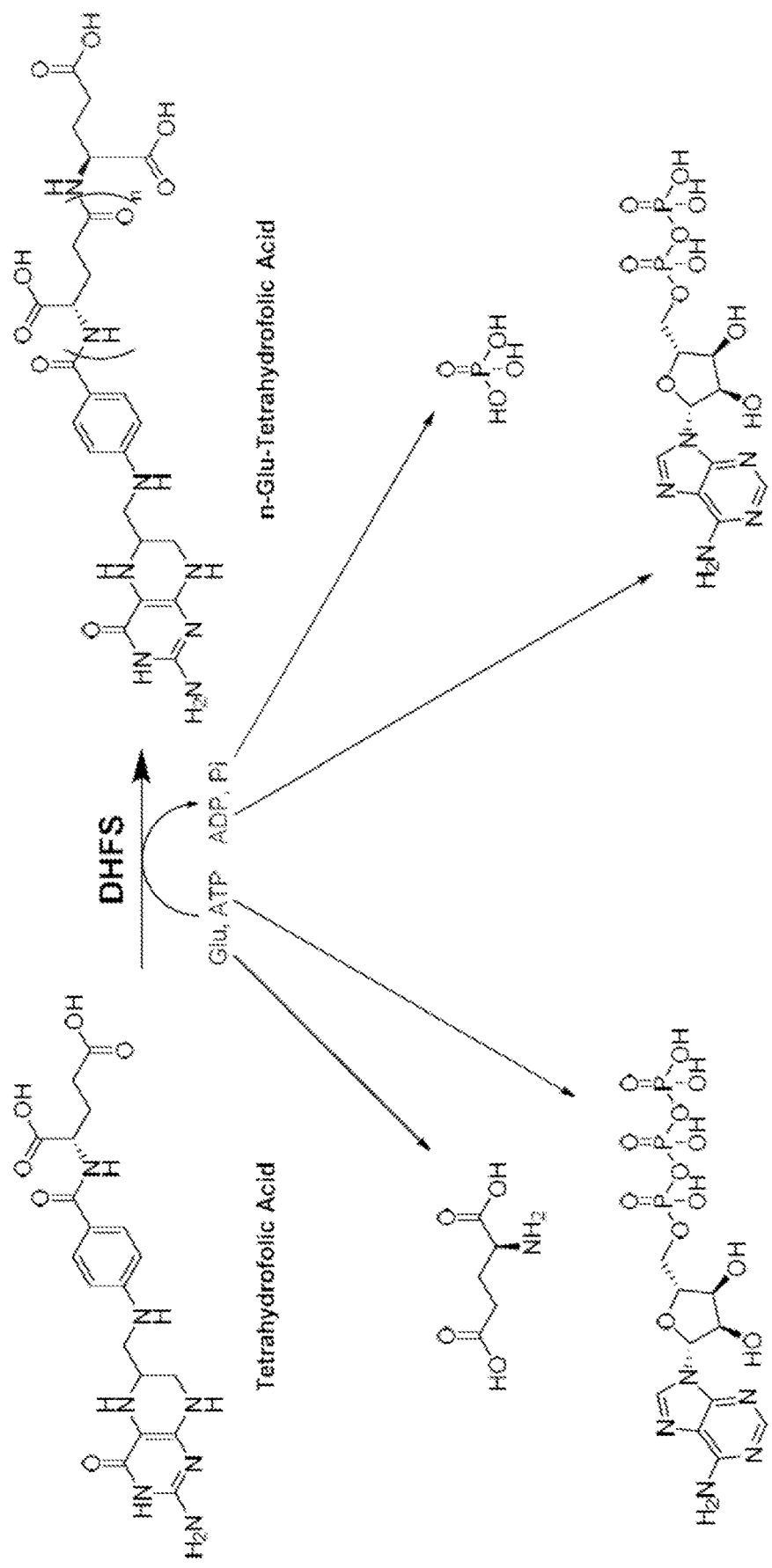
FIG. 19 is a schematic showing DHFS and its associated cosubstrates and coproducts in accordance with the present disclosure.

With a suitable DHFS substrate in hand (THFA), conditions to measure the rate of DHFS action were investigated. To ensure a real time rate determination (so as to not rely on end point analysis via mass spectrometry or UV spectroscopy, which do not capture subtle changes in rate as the reaction develops), the DHFS reaction was coupled to a reaction that results in a decrease in optical absorbance over time. Given none of the substrates or cofactors of DHFS (see e.g., FIG. 19) would be suitable for absorbance change detection, a coupled enzyme reaction with pyruvate kinase/lactate dehydrogenase (PK/LDH) was chosen. In the presence of ADP (in this case produced by DHFS), PK would convert phosphoenolpyruvate (PEP) to pyruvate, reforming ATP in the process (see e.g., FIG. 20A). The pyruvate would then be reduced by LDH in a NADH dependent manner (see e.g., FIG. 20B). The oxidation of NADH to NAD$^+$ would cause a decrease in absorbance at 340 nm, which can be measured as a rate of DHFS activity as long as the PK/LDH process was not the rate limiting step of the pathway from THFA to NAD$^+$.

Results

Figure 21A:
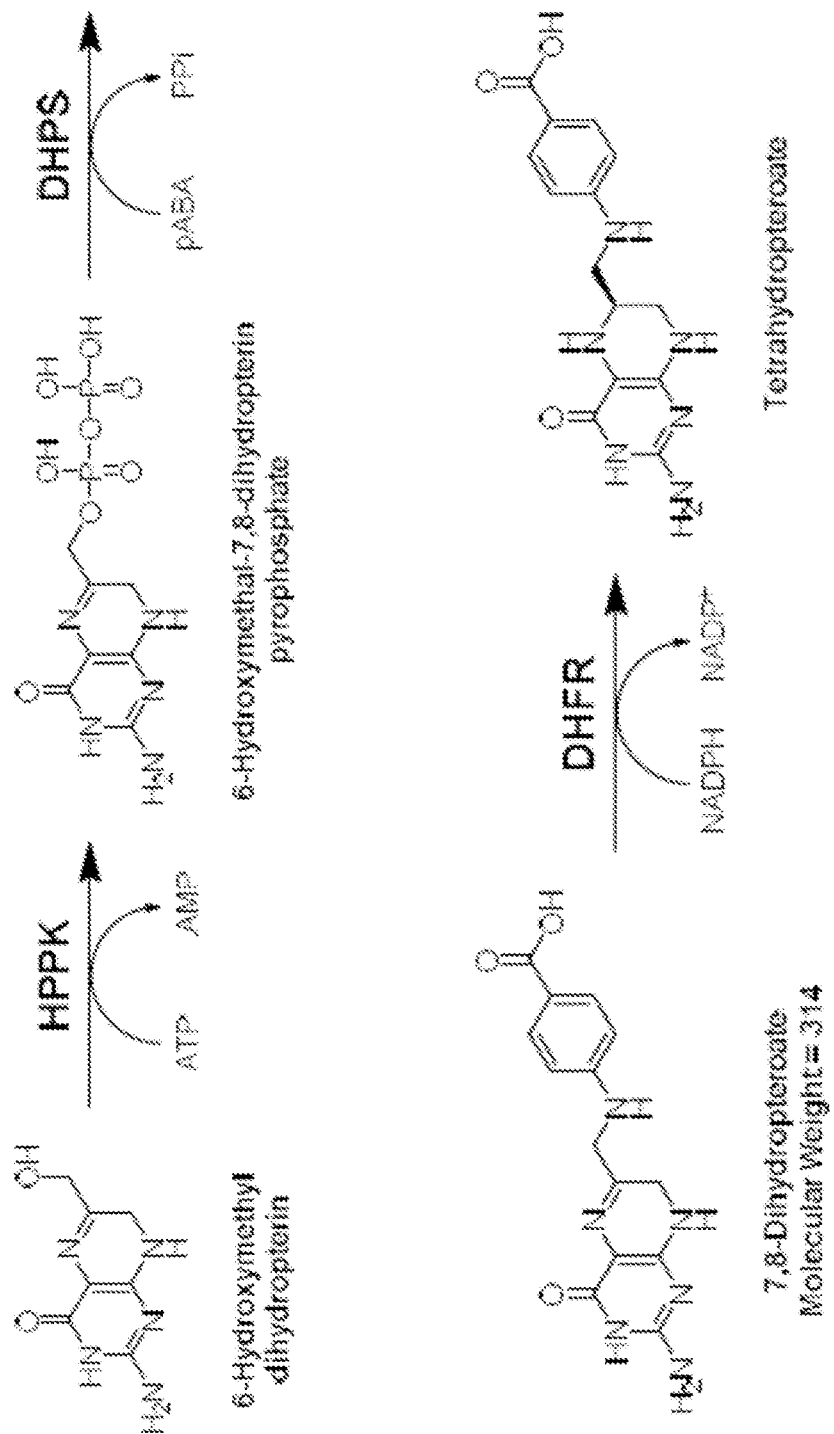
FIG. 21A-FIG. 21C is an exemplary embodiment showing the results of the HPPK/DHPS/DHFR assay for detection of DHPS activity in accordance with the present disclosure.
Figure 21B:
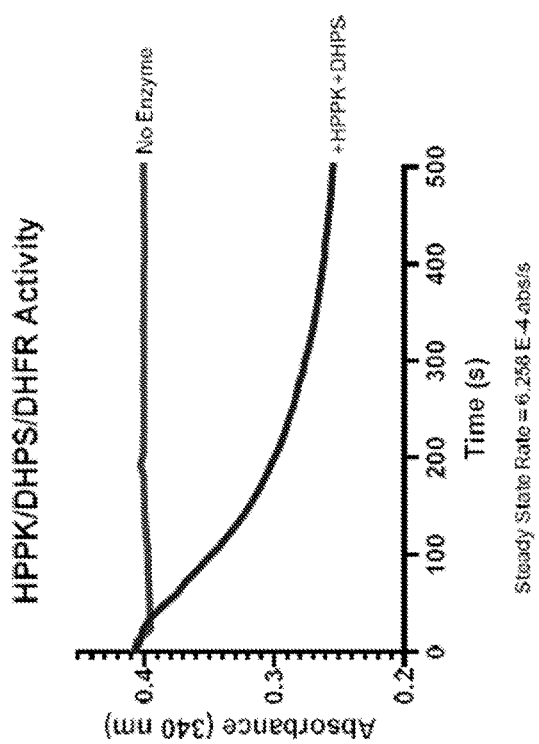
Figure 21C:
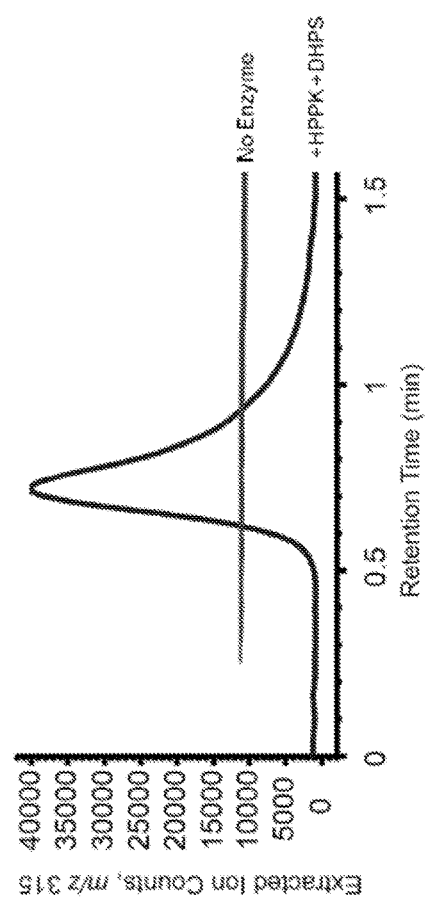
Figure 22B:
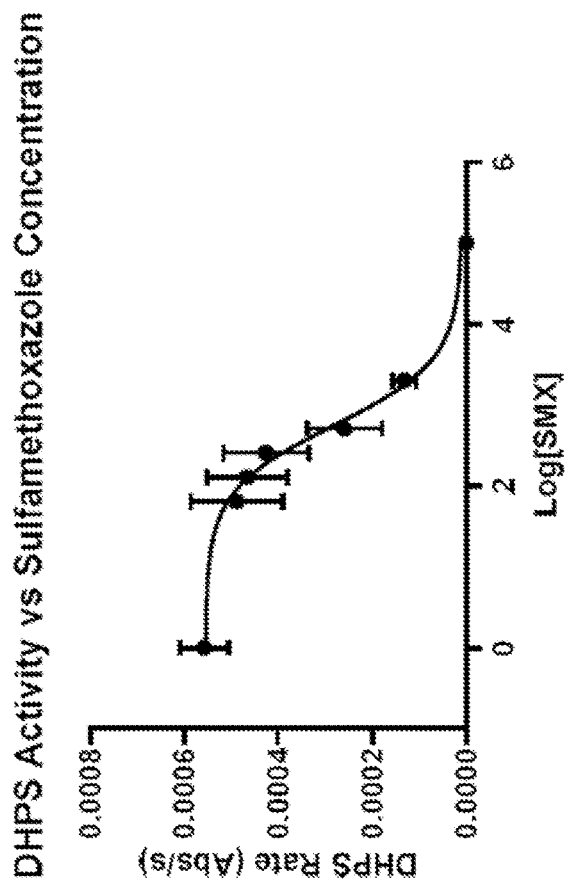
FIG. 22A-FIG. 22B is an exemplary embodiment showing the inhibition profile of known and possible inhibitors of DHPS in accordance with the present disclosure.
Figure 22A:
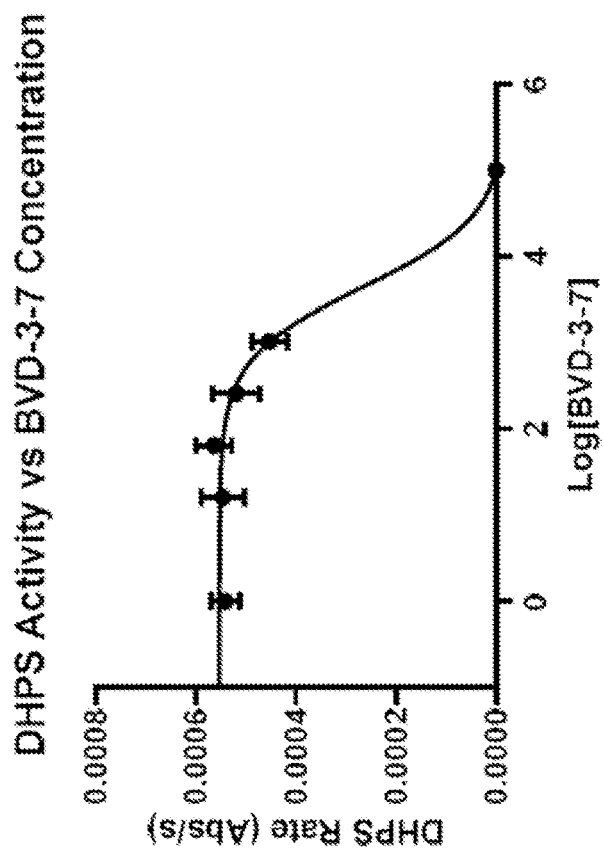
Figure 23A:
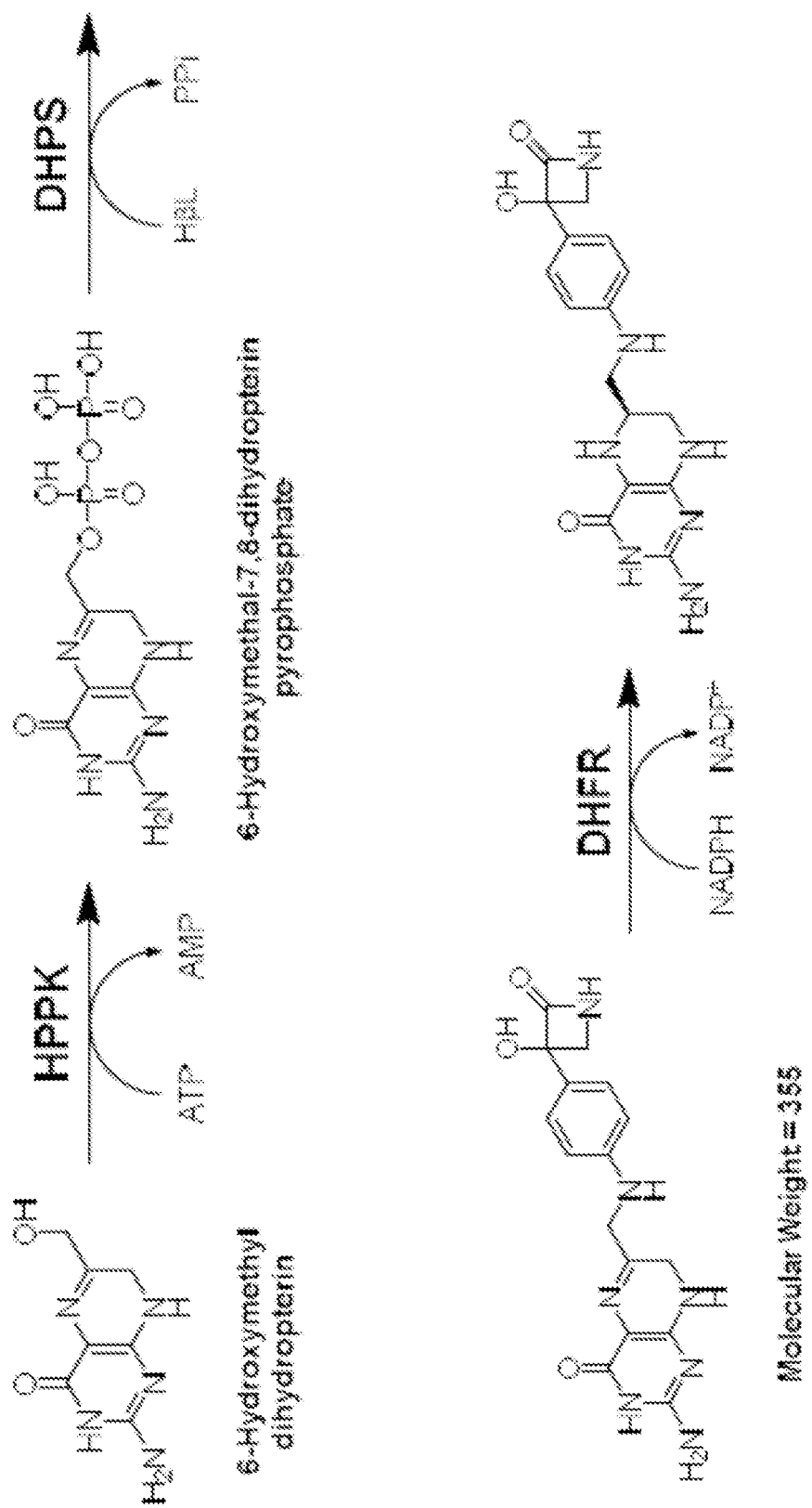
FIG. 23A-FIG. 23C is an exemplary embodiment showing use of HPPK/DHPS to produce and detect a 3-(para-$NH_2$-phenyl)-3-HβL-pterin adduct in accordance with the present disclosure.
Figure 23B:
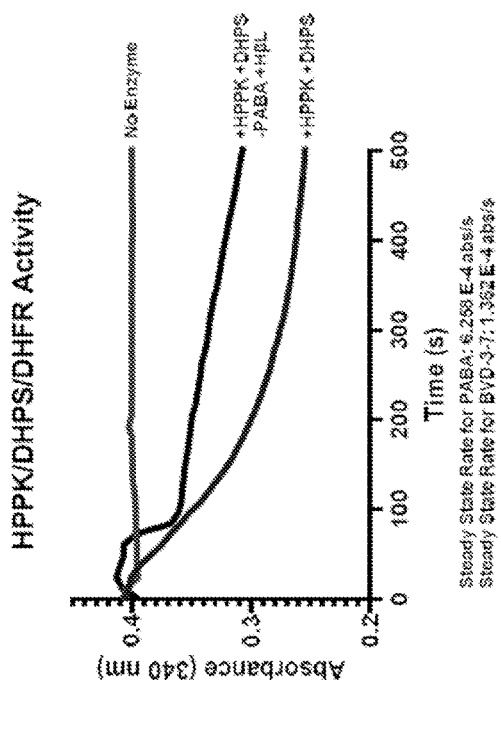
Figure 23C:
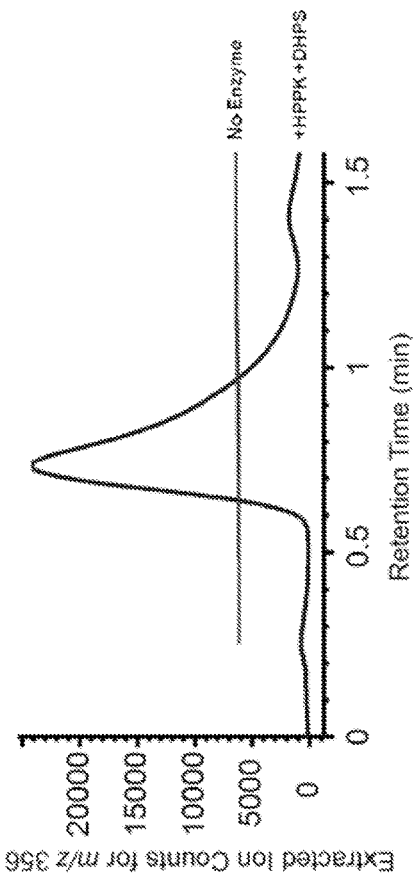

HPPK, DHPS, DHFR and all their associated cosubstrates (ATP, PABA, NADPH) were combined in suitable buffer conditions (pH=7.5) and the optical absorbance at 340 nm was measured over time (see e.g., FIG. 21A). The enzymes were filtered out using 10 kDa MWCO centrifugal filters and the samples were analyzed via LCMS to detect the predicted [M+H]+ molecular ion corresponding to 7,8-DHP (expected m/z=315) (see e.g., FIG. 21C). An apparent steady-state rate of 6.258 E$^{-4}$ abs/s was observed when DHPS was present compared to the control reaction lacking DHPS (see e.g., FIG. 21B). The same assay was run with variable amounts of sulfamethoxazole (a known DHPS inhibitor) included, showing a dose-dependent inhibitory response with an apparent IC50 of 558 µM±200 µM (see e.g., FIG. 22A). The same assay was run with variable amounts of 3-(para-NH$_2$-phenyl)-3-HβL 2.44 and the calculations for an apparent IC50 returned values of 4.39 mM±5.203 mM (see e.g., FIG. 22B) indicating 2.44 is not an inhibitor of DHPS. Complete replacement of PABA by 2.44 showed a reduced but still measurable rate of DHPS action (see e.g., FIG. 23A and FIG. 23B) relative to PABA alone (a steady-state approximation rate of 1.362 E$^{-4}$ abs/s). Analysis of the reaction by LCMS revealed a strong peak in the extracted ion chromatogram with the expected m/z value (356) corresponding to the [M+H]+ molecular ion of the desired 3-HβL-pterin product (see e.g., FIG. 23C).

Figure 24A:
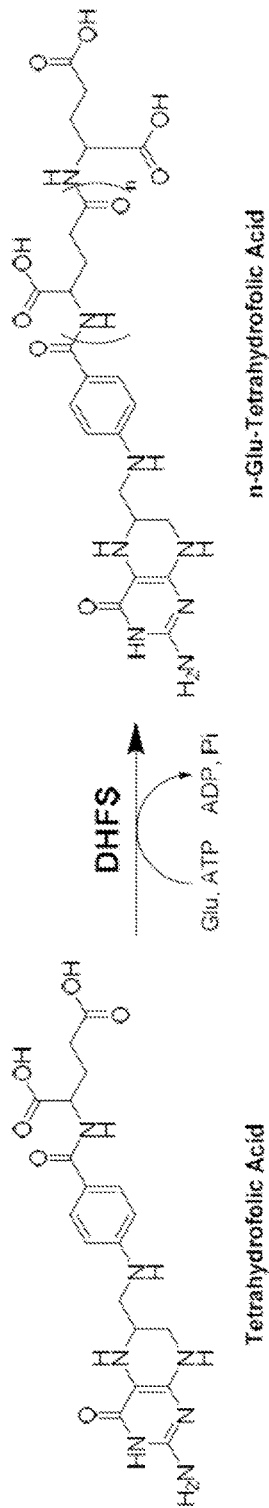
FIG. 24A-FIG. 24B is an exemplary embodiment showing the steady-state rate determination of DHFS in accordance with the present disclosure.
Figure 24B:
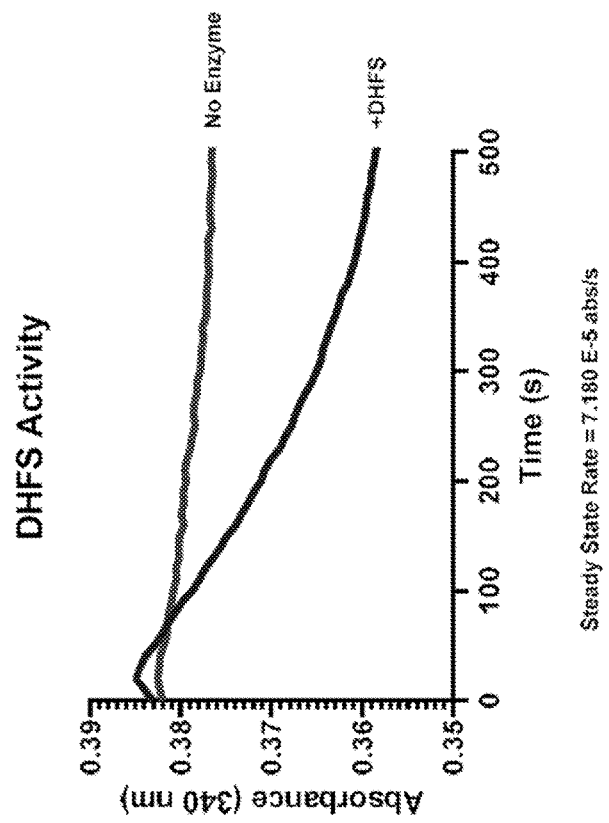
Figure 25A:
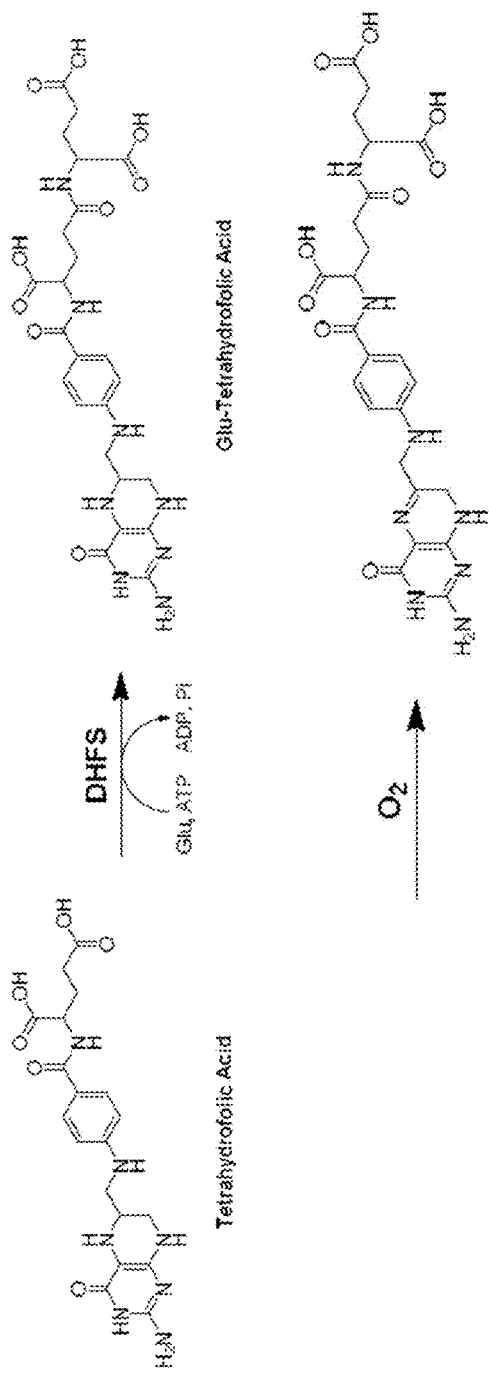
FIG. 25A-FIG. 25B is an exemplary embodiment showing DHFS glutamylation of THFA in accordance with the present disclosure.
Figure 25B:
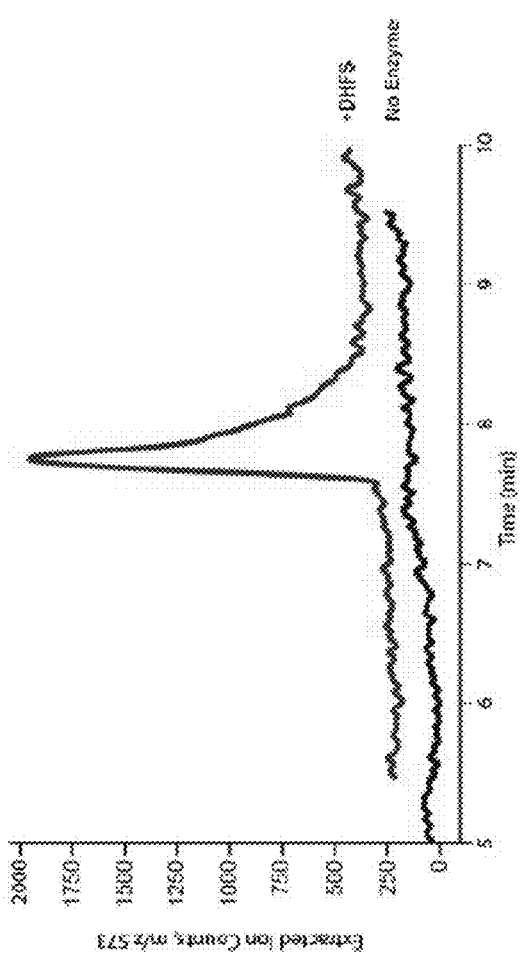

THFA and its associated cofactors (L-Glu, ATP) were dissolved in degassed buffer solution (pH=7.5) to reconstitute DHFS activity with coupling to PK/LDH activity in the presence of excess cosubstrates (PEP, NADH) (see e.g., FIG. 24A). The optical absorbance at 340 nm was measured over time and a steady-state approximation of DHFS rate (7.18 E-5 abs/s) was determined (see e.g., FIG. 24B). Once the reaction had progressed for 20 minutes, 1 M HCl was added to quench the reaction and KCl+MeOH was added to agglutinate the protein and solubilize the pterin-containing metabolites. The vials were heated for 1 h at 70° C. and centrifuged to remove precipitated enzymes. The supernatant solution was spiked with a fixed concentration of Fmoc-alanine as an internal standard for LCMS analysis. A significant peak with apparent m/z=573 corresponding to the expected [M+H]+ molecular ion of the partially reduced THF-Glu product was observed in the extracted ion chromatogram (see e.g., FIG. 25A-FIG. 25B).

Discussion

A suitable substrate for DHPS, the 3-(para-NH$_2$-phenyl)-3-HβL tested, resulted in slower rates of DHPS action. If harnessing the native HPPK/DHPS pathway in bacteria as a prodrug approach to assemble a 3-HβL-pterin compound in vivo, it may be subsumed by the much greater production of 7,8-DHP and downstream THE by those same enzymes. Given intracellular concentrations of PABA can be upregulated in response to stress, it may be difficult to allow enough 3-HβL into a cell to outcompete the 7,8-DHP production rate.

However, the chemoenzymatic synthesis of the 3-HβL-pterin compound in vitro shows the potential for chemoenzymatic routes in the production of antifolates. The reduced pterin ring in the 3-HβL-pterin synthesized would likely be more challenging to access through conventional synthetic methods, or at the very least prohibitively difficult to make and purify on any type of scale.

A remaining challenge for pterin-based antifolate molecules is the solubility profile of the biological pteridine molecules, typically requiring strong base (pH=13) for dissolution. The partially reduced and fully reduced pterin rings have better solubility at assay buffer conditions, but high enough working concentrations were not achievable, and thus comparatively large volumes of pteridine solutions were used to achieve suitable assay final concentrations. The addition of DMSO as a cosolvent to the buffer for the DHFS-catalyzed reaction increases the rate of ADP formation according to end point analysis with the PK/LDH coupled assay (Not shown). This may be due to the increased solubility of pteridines in the buffer conditions. However, large quantities of DMSO in the buffer conditions seem to decrease the rate of the PK/LDH coupled reaction making this coupled step rate limiting. As such, the rate for DHFS measured is likely not the maximum rate of the enzyme in the reaction matrix. More likely it is the maximum rate that can be measured by ADP detection coupled enzyme assays. Previous work to detect the product of DHFS activity by Mikol and coworkers indicates that DHFS can have quick rates at pH=9.5 but this pH was not compatible with the PK/LDH coupled reaction in this assay. There is also a background rate of ADP production in the coupled enzyme assay that may be attributed to the nonenzymatic hydrolysis of ATP to ADP at high pH; however, this background rate is minimal in the conditions listed, and may easily be subtracted out of all the rates to generate background correction kinetic data sets. In conclusion, inclusion of potential inhibitors in the DHFS reaction with coupled regeneration of ATP from ADP via the coupled PK/LDH reaction may be performed without DMSO cosolvent levels exceeding what is tolerated by the PK/LDH enzymes.

Conclusion

Several key discoveries were made and a suitable enzyme assay for real time rate detection of DHFS activity was developed herein. 3-(para-NH$_2$-phenyl)-3-HβL is a substrate, but not an inhibitor of DHPS enabling a prodrug strategy. Incorporation of 3-HβL-pterins into the folate biosynthetic pathway is similar to the classic mechanism of the sulfa drugs, but without product inhibition of DHPS. However, the rates of incorporation of the 3-(para-NH$_2$-phenyl)-3-HβL PABA mimic are slower compared to PABA, which will also be presumably present in the cell at competitively high concentration, challenging some embodiments of this prodrug strategy in vivo. The optimized DHFS steady-state kinetic assay reported herein may be used to determine if the inhibitors hypothesized herein are feasible and potent.

Materials and Methods

All chemicals and solvents were purchased from reputable vendors (. Sigma Aldrich, Oakwood, Enamine, Thermo Fisher). All prep-HβLC was performed using an Agilent/HP 1050 quaternary pump module with an Agilent/HP MWD module with a Phenomenex Luna 10 u C18(2) 100A column, 250×21.20 mm, 10 μm with guard column. All LCMS was performed on an Agilent 6130 quadrupole LC-MS with G1313 autosampler or G1367B autosampler, G1315 diode array detector, and 1200 series solvent module. A Phenomenex Gemini C18 column, 50×2 mm, 5 μm with guard column was used for all LC-MS separations. Mobile phases for prep-HβLC and LCMS were 0.1% formic acid in (A) H$_2$O and (B) CH$_3$CN, and data were processed using ChemStation software (Agilent). NMR was performed on either an Agilent DD2 600 MHz, an Agilent DD2 500 MHz, or a Varian Unity Plus 300 MHz instrument and data was processed using MestraNova. All optical absorption plate readings were performed on either a Spectra Max Plus 384 or a Fisher AccuSkan Go.

Enzyme Expression and Purification

The E. coli HPPK gene was cloned into pET28 protein expression vector and transformed into E. coli BL21 for over expression as the N-His6-tagged construct. An overnight culture of HPPK E. coli BL21 in LB broth was grown then 500 μL of this overnight culture was added to an autoclaved flask containing 900 mL Terrific Broth (12 g tryptone, 24 g yeast extract, 5 g glycerol), 99 mL phosphate buffer (2.314 g KH2PO4, 1.24 g K2HPO4) and 1 mL of Kanamycin sulfate (50 mg/mL).

Figure 26:
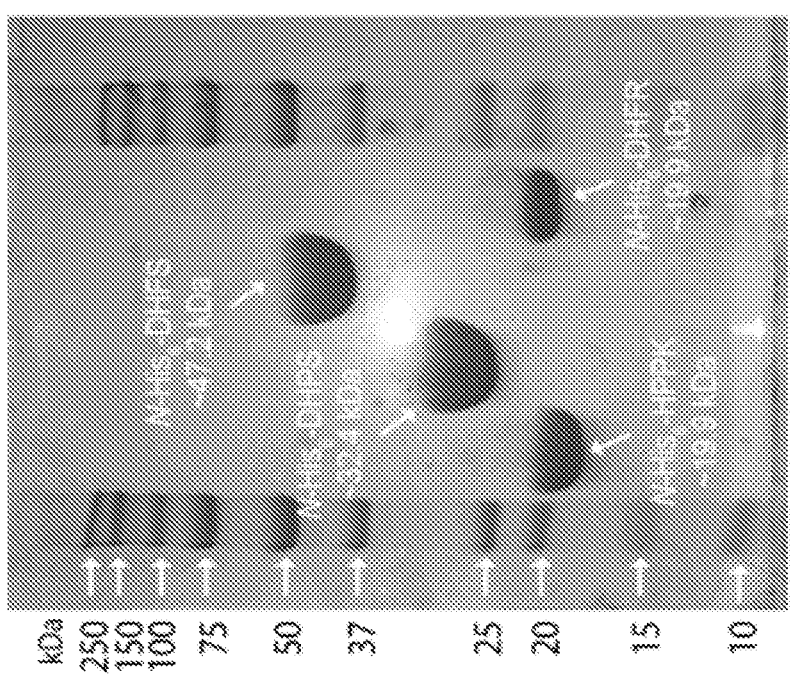
FIG. 26 is an image showing SDS-Page gel of purified folate biosynthetic enzymes in accordance with the present disclosure.

The culture was incubated at 37° C., spinning at 225 rpm, until the OD600 4–0=0.5-0.9 (~4.5 h). The flasks were cooled then induced with IPTG and incubated overnight at 15° C., spinning at 225 rpm. The flask was divided into 4 parts and centrifuged for 35 min, at 4° C., at 4996 rpm. To 100 mL lysis buffer (50 mM K2HPO4, 500 mM NaCl, 20 mM Imidazole, 10% glycerol by volume, and 5 mM β-mercaptoethanol, pH=8.0) was added protease inhibitor and the solution was used to dilute the cells leftover after decanting the centrifuge vials. The cells were flash frozen in liquid nitrogen then thawed and put through a cell homogenizer, washing with lysis buffer. The cells were centrifuged at 45 k rpm, 4° C., for 35 min then poured on a Ni column that had been washed with lysis buffer. The column was shaken for 1 h, then allowed to settle. The column flow through was collected then the column was washed with 2×40 mL lysis buffer and 4×15 mL elution buffer (50 mM K2HPO4, 500 mM NaCl, 300 mM Imidazole, 10% glycerol by volume, and 5 mM β-mercaptoethanol, pH=8.0). The elution buffer fractions were collected and put in a size exclusion membrane for soaking in size exclusion buffer (50 mM K2HPO4, 500 mM NaCl, 1 mM DTT, pH=8.0) overnight. The protein solution was concentrated by centrifugation in MWCO filter falcon tubes to yield pure HPPK (MW=17.842 kDa). DHPS (MW=30.615 kDa), DHFS (MW=47.495 kDa) and DHFR (MW=18.69 kDa) were purified in the same manner (see e.g., FIG. 26).

HPPK/DHPS/DHFR Steady State Kinetics

Stock solutions of all reagents were made using 100 mM Tris buffer (pH=7.5) and stored in fractions in a −80° C. freezer until use (see e.g., TABLE 5).

TABLE 5

Biochemical conditions for the HPPK/DHPS/DHFR kinetics assay.

|  | Stock concentration (µM) | Stock volume (µL) | Final concentration (µL) |
|---|---|---|---|
| MgCl$_2$ | 250000 | 3 | 5000 |
| β-mercaptoethanol | 1000000 | 3 | 20000 |
| Bovine Serum Albumin | 10 mg/mL | 15 | 1 mg/mL |
| 6-hydroxymethyl-7,8-dihydropterin | 500 | 45 | 150 |
| PABA | 2500 | 9 | 150 |
| ATP | 5000 | 9 | 300 |
| NADPH | 5000 | 4.5 | 150 |
| HPPK/DHPS/DHFR | 22.42/13.07/21.4 | 7.5 | 1.121/0.6535/1.07 |
| Tris buffer pH = 7.5 |  | 54 | 0 |

An assay stock solution containing everything except the enzymes was made and 142.5 µL was distributed to each well (6 total) on a quartz 96-well plate that had been flushed with argon. To each of the first three wells was then added 7.5 µL of the enzyme solution containing HPPK/DHPS/DHFR, and to each of the last 3 wells was added 7.5 µL of 100 mM Tris-buffer. The 96-well plate was put into a UV/Vis plate reader and incubated at 37° C. while the optical absorbance at nm was read every 10 s for 1 h. The apparent reaction rate for absorbance decrease was measured from between 0-5 min. Each well was combined with their triplicate partners and the solutions were centrifuge filtered through a molecular weight cutoff (MWCO) to remove any enzymes. The solutions then run on an LCMS with single ion monitoring methods to detect the various oxidation states of products.

HPPK/DHPS/DHFR Steady State Kinetics Inhibition

Stock solutions of all reagents were made using 100 mM Tris-buffer (pH=7.5) and stored in fractions in a −80° C. freezer until use (see e.g., TABLE 6).

TABLE 6

Biochemical conditions for the HPPK/DHPS/DHFR inhibition kinetics assay.

|  | Stock concentration (µM) | Stock volume (µL) | Final concentration (µL) |
|---|---|---|---|
| MgCl$_2$ | 250000 | 3 | 5000 |
| β-mercaptoethanol | 1000000 | 3 | 20000 |
| Bovine Serum Albumin | 10 mg/mL | 15 | 1 mg/mL |
| 6-hydroxymethyl-7,8-dihydropterin | 500 | 45 | 150 |
| PABA | 2500 | 9 | 150 |
| ATP | 5000 | 9 | 300 |
| NADPH | 5000 | 4.5 | 150 |
| HPPK/DHPS/DHFR | 22.42/13.07/21.4 | 7.5 | 1.121/0.6535/1.07 |
| Tris buffer pH = 7.5 + Inhibitor |  | 54 | 0 |

An assay stock solution containing everything except the HPPK/DHPS/DHFR solution and the Tris buffer+Inhibitor was made and 88.5 µL was distributed to each well (in triplicate) of a quartz 96-well plate to be used. 54 µL of a Tris buffer solution containing the inhibitor in appropriate concentrates to have final assay concentrations as shown in TABLE was added to each well. 7.5 µL of the enzyme solution containing HPPK/DHPS/DHFR was added to each well and the plate was put into a UV/Vis plate reader and incubated at 37° C. while the optical absorbance at 340 nm was read every 10 s for 1 h. The apparent reaction 1-9 rate for absorbance decrease was measured from between 0-5 min.

HPPK/DHPS/DHFR Steady State Kinetics with a 3-HG3L as a Substrate Stock solutions of all reagents were made using 100 mM Tris buffer (pH=7.5) and stored in fractions in a −80° C. freezer until use (see e.g., TABLE 7).

TABLE 7

Biochemical conditions for the HPPK/DHPS/DHFR kinetics assay with 3-HβL as a substrate.

|  | Stock concentration (µM) | Stock volume (µL) | Final concentration (µL) |
|---|---|---|---|
| MgCl$_2$ | 250000 | 3 | 5000 |
| β-mercaptoethanol | 1000000 | 3 | 20000 |
| Bovine Serum Albumin | 10 mg/mL | 15 | 1 mg/mL |
| 6-hydroxymethyl-7,8-dihydropterin | 500 | 45 | 150 |
| 3-HβL | 2500 | 9 | 150 |
| PABA | 2500 | 9 | 150 |
| ATP | 5000 | 9 | 300 |
| NADPH | 5000 | 4.5 | 150 |
| HPPK/DHPS/DHFR | 22.42/13.07/21.4 | 7.5 | 1.121/0.6535/1.07 |
| Tris buffer pH = 7.5 + Inhibitor |  | 54 | 0 |

An assay stock solution containing everything except the enzymes was made and 142.5 µL was distributed to each well (6 total) on a quartz 96-well plate that had been flushed with argon. To each of the first three wells was then added 7.5 µL of the enzyme solution containing HPPK/DHPS/DHFR, and to each of the last 3 wells was added 7.5 µL of 100 mM Tris-buffer. The 96-well plate was put into a UV/Vis plate reader and incubated at 37° C. while the optical absorbance at nm was read every 10 s for 1 h. The apparent reaction rate for absorbance decrease was measured from between 0-5 min. Each well was combined with 1-0 their triplicate partners and the solutions were centrifuge filtered through a molecular weight cutoff (MWCO) to remove any enzymes. The solutions then run on an LCMS with single ion monitoring methods to detect the various oxidation states of products.

DHFS Steady State Kinetics

Stock solutions of all reagents were made using 100 mM Tris buffer (pH=7.5) and stored in fractions in a −80° C. freezer until use (see e.g., TABLE 8).

TABLE 8

Biochemical conditions for the DHFS kinetics assay.

|  | Stock concentration (µM) | Stock volume (µL) | Final concentration (µM) |
|---|---|---|---|
| MgCl$_2$ | 250000 | 6 | 10000 |
| DTT | 250000 | 3 | 5000 |
| BSA | 10 mg/mL | 15 | 1 mg/ml |
| Glycine | 1250000 | 6 | 50000 |
| PEP | 7500 | 3 | 150 |
| NADH | 5000 | 4.5 | 150 |
| Pk/Ld | 600/900 unit/mL | 25 | 100/150 unit/mL |
| ATP | 15000 | 1.5 | 150 |
| Glutamate | 7500 | 2 | 100 |
| THF | 2000 | 3.75 | 50 |
| DHFS | 100 | 4.5 | 3 |
| 100 mM Tris pH = 7.5 | Total volume w/o DHFS | 69.75 |  |

An assay stock solution containing everything except DHFS and the Tris buffer was made and 69.75 µL was distributed to each of 6 wells (flushed with argon) of a quartz 96-well plate. 75.75 µL Tris buffer was added to each well. The 96-well plate was incubated at 37° C. for 10 min then 4.5 µL of DHFS solution was added to 3 wells and 4.5 µL of Tris buffer was added to the other three. The 96-well plate was put into a UV/Vis plate reader and incubated at 37° C. while the optical absorbance at 340 nm was read every 10 s for 1 h. The apparent reaction rate for absorbance decrease was measured from between 0-5 min. Each well 1-9 was combined with their triplicate partners and the solutions were centrifuge filtered through a molecular weight cutoff (MWCO) to remove any enzymes. The solutions then run on an LCMS with single ion monitoring methods to detect the various oxidation states of products.

Example 3: Inhibition of Dhfs

The 3-(para-NH$_2$-phenyl)-3-Hβ L synthesized herein was ligated to pterin mimics, both synthetically and chemoenzymatically, and tested to determine the dose-dependent inhibition of DHFS under steady-state conditions. Two compounds were found to be biochemical inhibitors of DHFS, one with low micromolar IC50 values that is capable of 100% inhibition. The 3-Hβ L moiety proved vital to potent DHFS inhibition, though the precise mechanism of inhibition is not fully elucidated. No compound proved to have any effect against the growth of bacterial cells (*E. coli* and *S. aureus*).

Introduction

The synthesis of a 3-(para-NH$_2$-phenyl)-3-Hβ L compound 2.44 and the development of biochemical assays to determine if derivatives of 2.44 are inhibitors of dihydrofolate synthetase (DHFS) are discussed above. Herein is described the efforts to develop potent inhibitors of DHFS with potential antimicrobial activities.

Molecular Docking Efforts Towards Understanding Potential DHFS Inhibitors

Figure 27A:
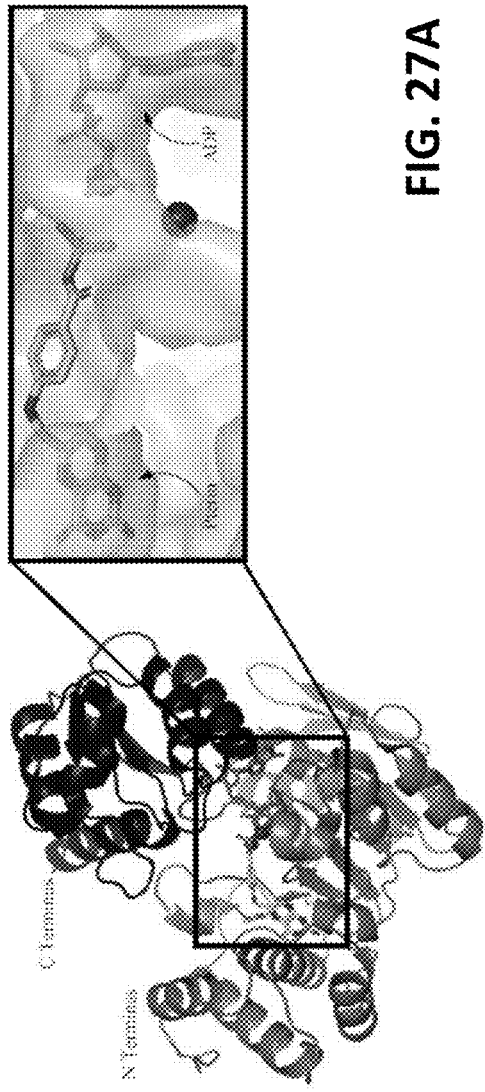
FIG. 27A-FIG. 27B is an exemplary embodiment showing 7,8-dihydropteroate phosphate and ADP bound to DHFS (PDB 1W78) in accordance with the present disclosure.
Figure 27B:
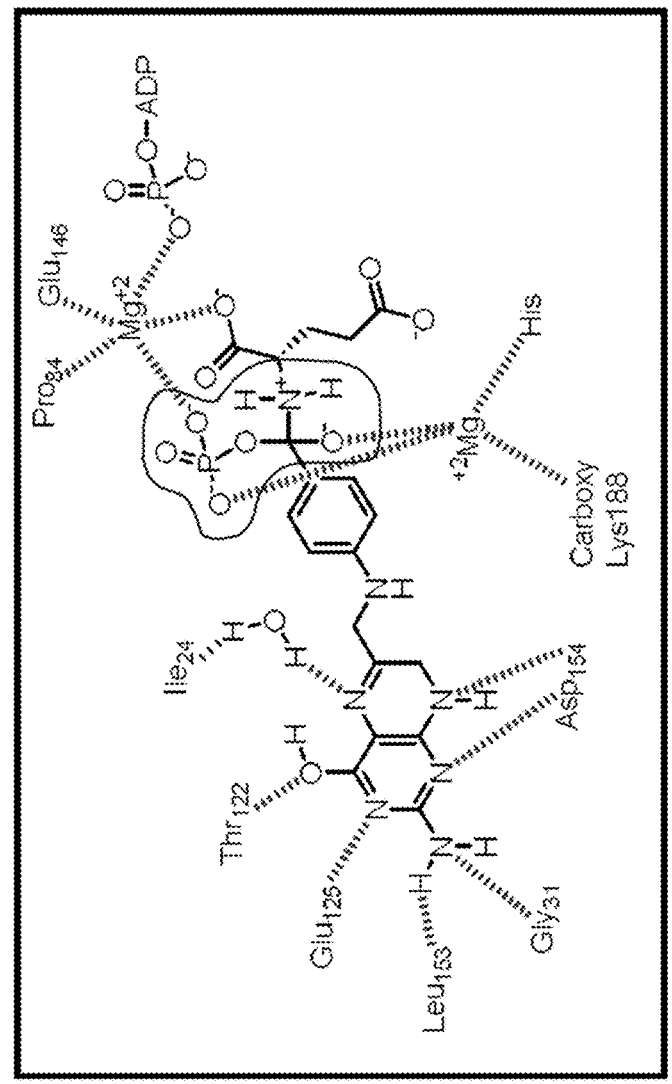

The various crystal structures of DHFS available on the PDB were investigated for potential use as molecular docking scaffolds. The pterin moiety of 7-8-dihydropteroic acid (7,8-DHPA) seems to function as an anchor, due to its tight binding pocket and multitude of electrostatic interactions with the active site (see e.g., FIG. 27A-FIG. 27B). Is this pterin moiety necessary to position the 3-Hβ L warhead properly in the active site? Is the native pterin heterocycle the only aromatic heterocyclic system that can properly position the PABA moiety in the DHFS active site? In the 3-(para-NH$_2$-phenyl)-3-Hβ L 2.44, there is a stereocenter at 3C of the β-lactam ring. What is the optimal stereochemistry for 3C? What if the 3-Hβ L has substituents at 4C, does that change the optimal stereochemistry?

Figure 28A:
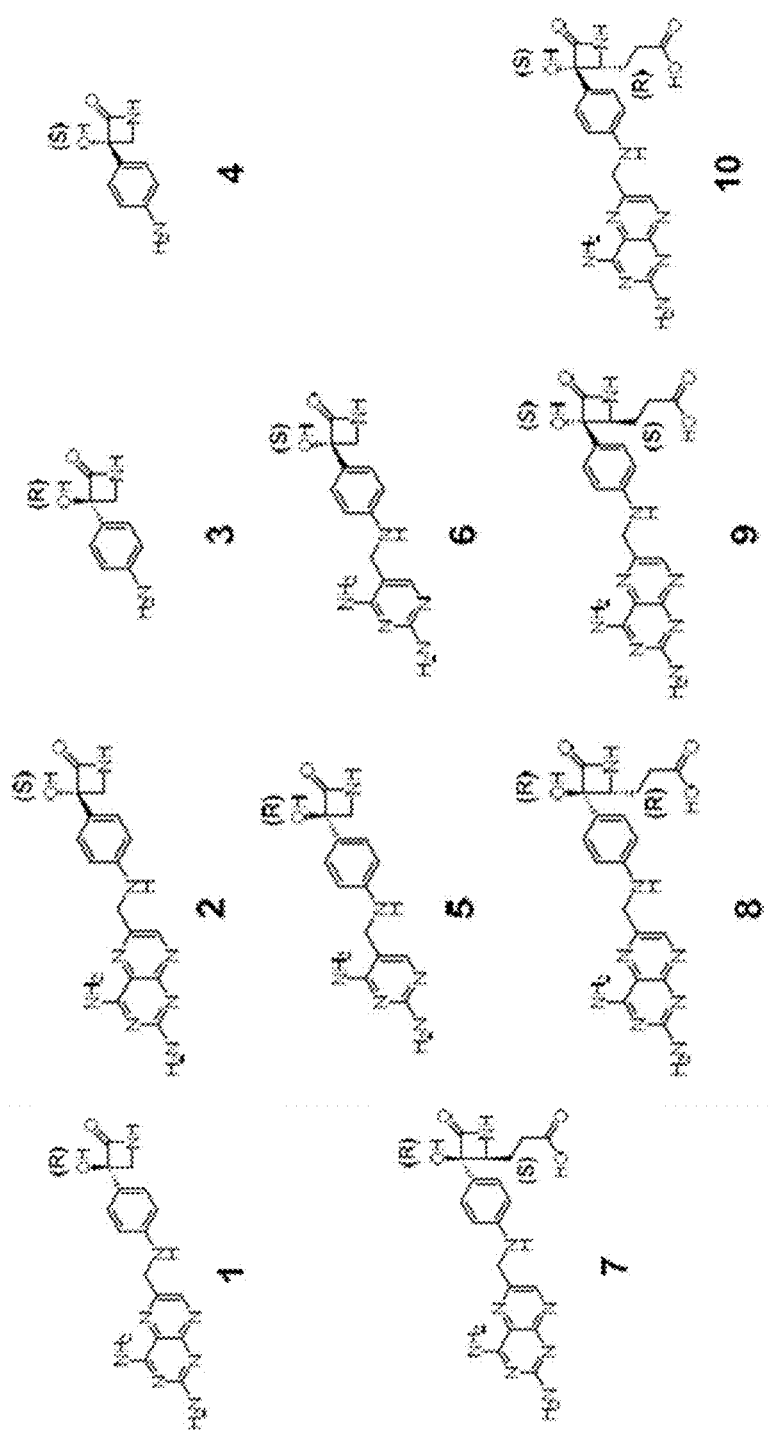
FIG. 28A-FIG. 28G is an exemplary embodiment showing the docking campaign in accordance with the present disclosure.
Figure 28B:
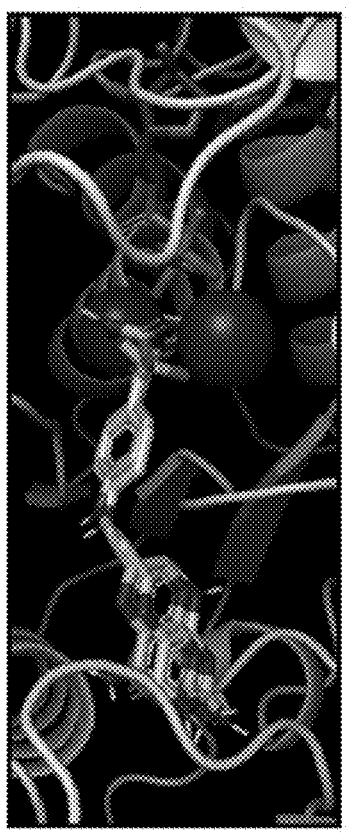
Figure 28D:
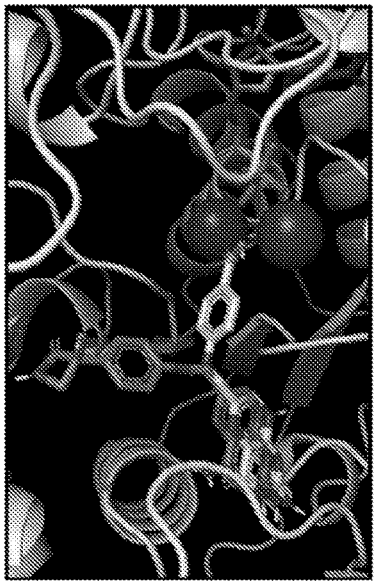
Figure 28F:
Figure 28C:
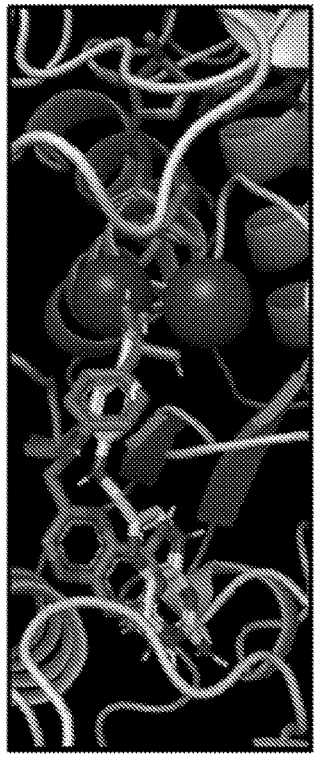
Figure 28E:
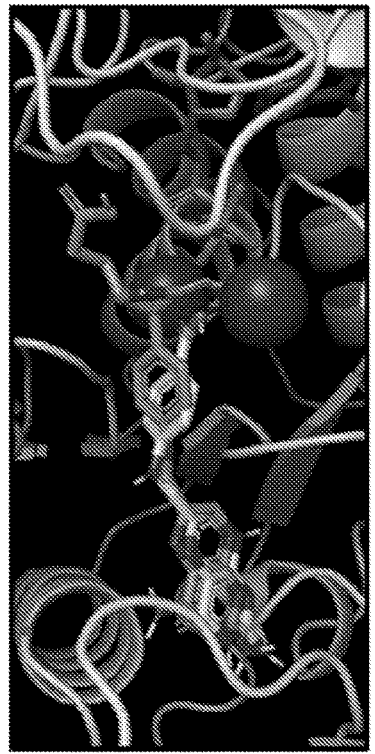
Figure 28G:
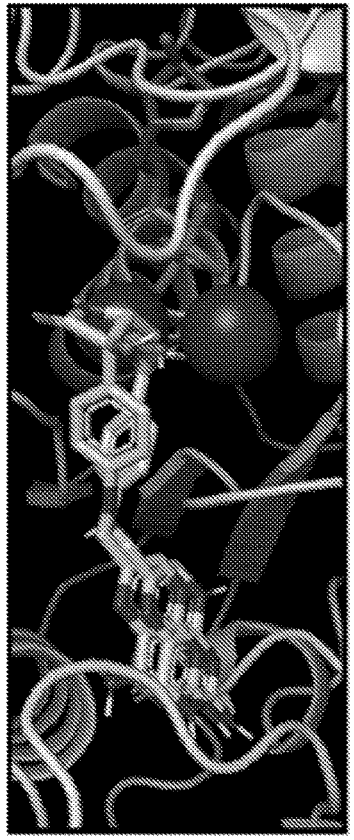

These questions were, collectively, the impetus behind a molecular docking campaign using AutoDock Vina to inform potential synthetic routes to inhibitors. Using a model of DHFS derived from the PDB (1W78) and bound ATP, 10 potential compounds were investigated for potential binding (see e.g., FIG. 28A). 7,8-DHP was docked to the DHFS model for confirmation of model integrity, having a binding affinity of −9.5 kcal/mol. Given the drop off in binding between compounds 1+2 (9.1 and 8.7 kcal/mol respectively) (see e.g., FIG. 28B-FIG. 28C) and 3+4 (6.2 and 6.0 kcal/mol respectively) (not shown), it seems that some sort of pterin on the aniline ring is important for binding. The pterin ring accounts for a large proportion of the binding affinity, given the difference between compound 2 and compound 2 out-pose (see e.g., FIG. 28C-FIG. 28D) is only 0.1 kcal/mol (8.7 and 8.6 kcal/mol respectively). A shortened pterin-moiety (see e.g., FIG. 28E) maintained high binding affinity (8.5 kcal/mol) as compared to compound 1 but was unable to place the 3-hydroxy group of the β-lactam towards the ATP, a key part of the hypothesis for activity. Once a substituent was placed at the 4C position, the stereochemistry at the 3C position greatly affected the binding mode. When the stereochemistry at 3C and 4C was opposite (compound 7 is (R) at 3C and (S) at 4C) the preferred binding mode pointed the 4C substituent out towards solvent in order to put the 3-hydroxy back towards the ATP (see e.g., FIG. 28F). When the stereochemistry at 3C and 4C was the same (compound 8 is (R) at 3C and (R) at 4C) the preferred binding mode put the 4C substituent deep into the active site and pointed the 3-hydroxy group out towards solvent (see e.g., FIG. 28G). Given the high binding affinity for compounds 7 and 8 (9.4 and 9.1 kcal/mol respectively) relative to an unsubstituted β-lactam ring (compound 1), the active site of DHFS may be capable of binding a large array β-lactam compounds. Whether these differentiated β-lactam rings can be phosphorylated in the active site remains to be seen. It is clear that, if phosphorylation at the 3-hydroxy group is important, a shortened pterin moiety may result in a drastic loss of potency for any potential inhibitor.

Synthetic Efforts Towards 3-(para-NH$_2$-phenyl)-3-Hβ L Pterin Mimics

Figure 29B:
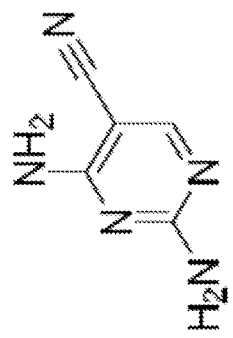
FIG. 29A-FIG. 29B is an exemplary embodiment showing the starting materials for pterin mimic chemistry in accordance with the present disclosure.
Figure 29A:
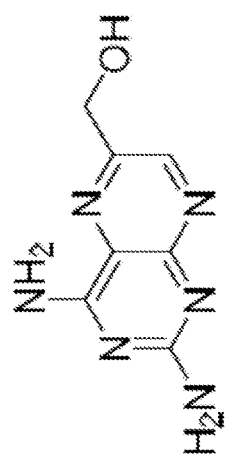

As described herein, the biological pterin heterocycle is prone to rapid air oxidation. Hence, two air stable heterocyclic mimics of the pterin moiety were chosen based on the molecular docking discussed above for the synthesis of 3-Hβ L antifolates. The first heterocycle was the pteridine moiety found in the anticancer agent methotrexate. The pteridine heterocycle is readily available for purchase and a proven clinically relevant pharmacophore able to mimic the natural pterin in folate, 2,4-diamino-6-(hydroxymethyl) pteridine (see e.g., FIG. 29A). The second pterin mimic was derived from the antimicrobial agent trimethoprim. Like methotrexate, the 2,4-diaminopyrimidine-5-carbonitrile heterocycle (see e.g., FIG. 29B) is readily available for purchase in large quantities from commercial suppliers. Further, the trimethoprim pterin mimic is another clinically proven pharmacophore able to mimic the natural pterin in folate. These two heterocyclic ring systems enabled testing of the preference of folate biosynthetic enzymes for different pterin mimics which presumably drive ligand binding of the designed synthetic inhibitors.

Figure 30:
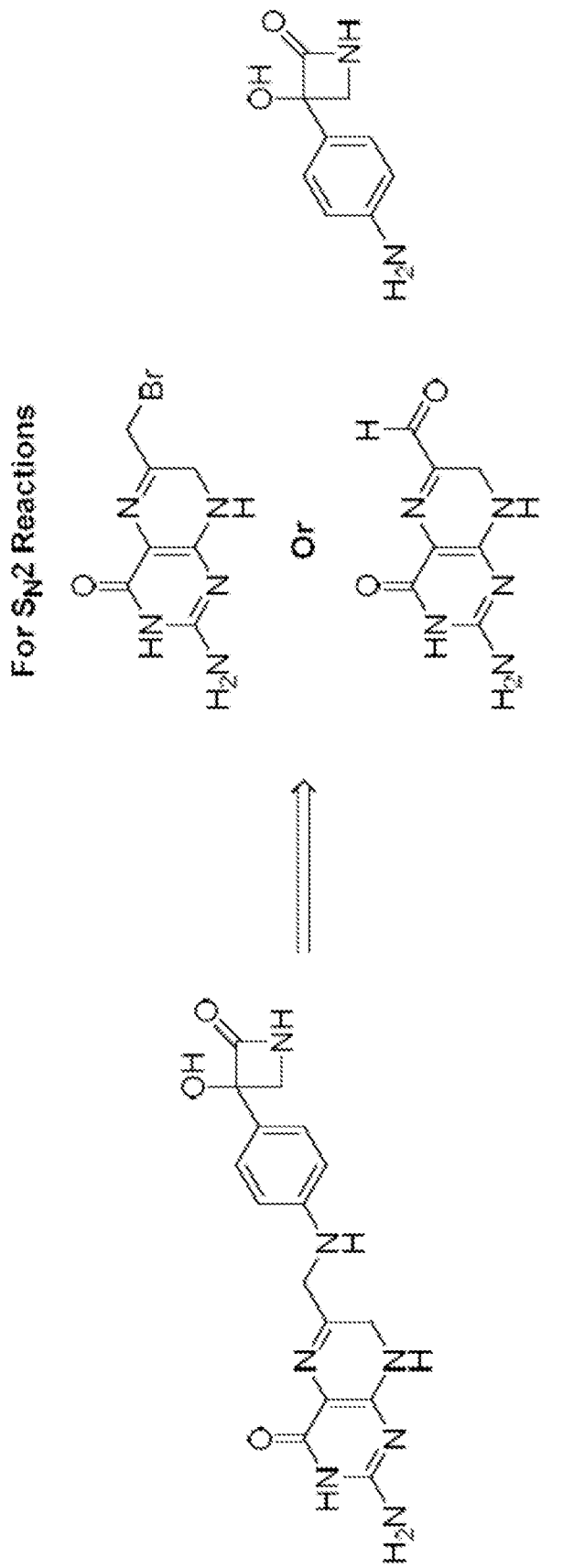
FIG. 30 is a schematic showing retrosynthesis for a pterin-3-(para-$NH_2$-phenyl)-3-HβL compound in accordance with the present disclosure.
Figure 31:
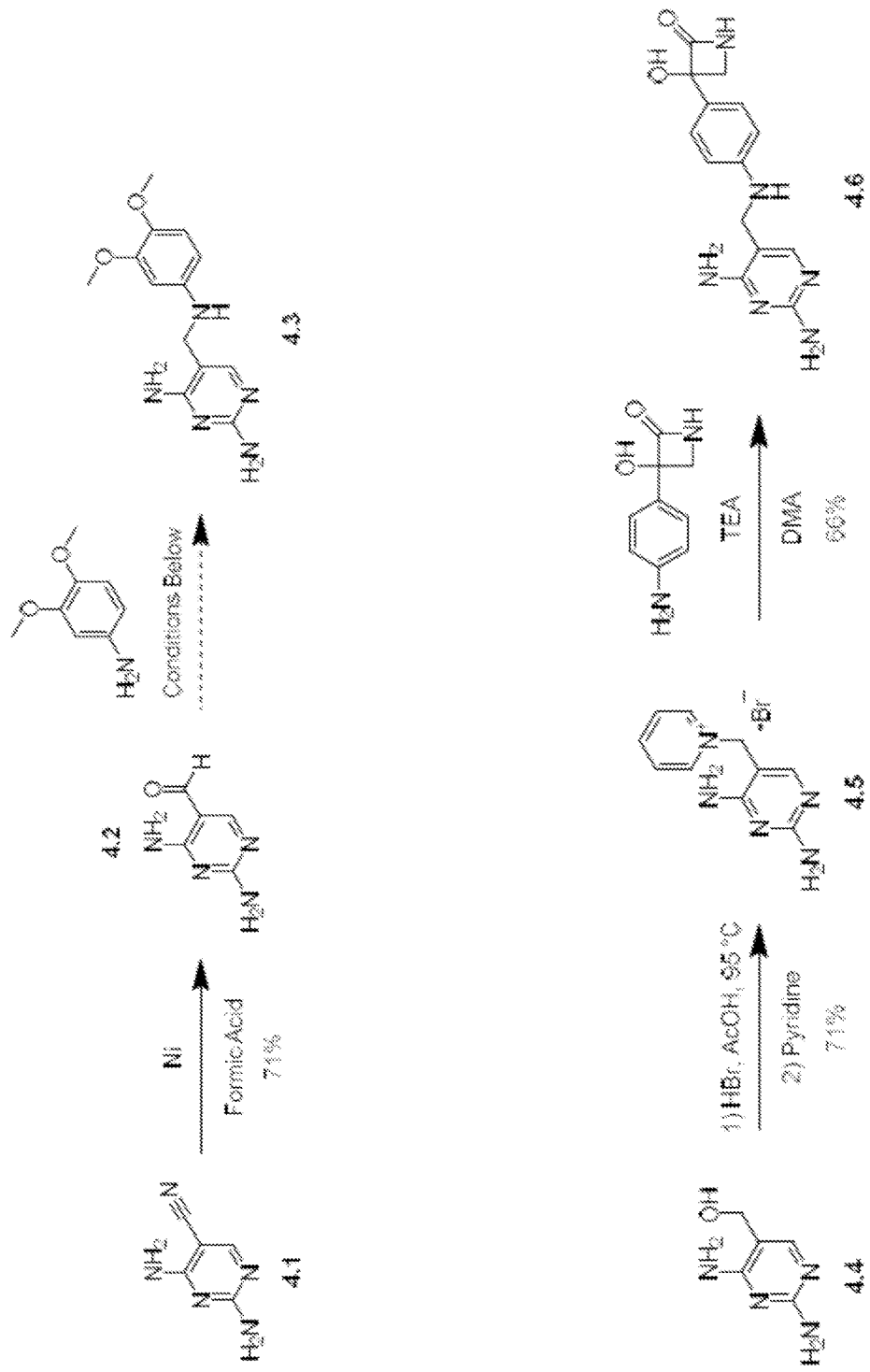
FIG. 31 is a schematic showing the synthetic efforts towards a pterin mimic-3-(para-$NH_2$-phenyl)-3-HβL using the pterin mimic from trimethoprim in accordance with the present disclosure. Reductive amination attempts were unsuccessful, but bromination followed by SN2 displacement provide the desired product.

Retrosynthetic analysis of the target inhibitors revealed a synthetic strategy starting from commercially available pterin mimics with electrophilic activation at the benzylic positions (see e.g., FIG. 30). Two potential electrophiles for the forward reaction ligation of the 3-(para-NH$_2$-phenyl)-3-Hβ L and the pterin mimic were envisioned. The first was an aldehyde suitable for reductive amination and the second was an alkyl halide suitable for SN2 chemistry. Costi and coworkers demonstrated the use of a benzylic bromide as the electrophile in SN2 reactions with a variety of alkyl and aryl amine nucleophiles. Aldrich and coworkers demonstrated the use of a pterin aldehyde as the electrophile in reductive amination reactions with aniline derivatives. 2,4-diaminopyrimidine-5-carbonitrile was reduced to aldehyde 4.2 using transfer hydrogenation (see e.g., FIG. 31 and TABLE 9).

TABLE 9

Synthetic efforts towards a pterin mimic-3-(para-NH$_2$-phenyl)-3-H$\beta$L using the pterin mimic from trimethoprim.

| Reaction Attempt | Reagents | Solvent | Temperature | Result |
|---|---|---|---|---|
| 1 | 1 equiv NaCNBH$_3$ | MeOH | 25° C. | No Reaction |
| 2 | 2 equiv Na(CH$_3$COOH)$_3$BH, 1 equiv CH$_3$COOH | THF | 25° C. | No Reaction |
| 3 | 6 equiv Na(CH$_3$COOH)$_3$BH, 3 equiv CH$_3$COOH | DCE | 25° C. | No Reaction |
| 4 | 1 equiv Diludine, 0.1 equiv PTSA | H$_2$O | 25° C. | No Reaction |
| 5 | 1.5 equiv NaCNBH$_3$, 1.5 equiv PTSA | EtOH | 25° C. | No Reaction |

At the time of these synthetic efforts 3-(para-NH$_2$-phenyl)-3-HP$\beta$L 2.44 was prepared in small quantities (<10 mgs) so a model commercially available aniline was used as a test substrate for the reductive amination. All the trials failed to produce product, due in large part to solubility issues of both the aldehyde and reducing agent in the solvents listed in FIG. 30. To facilitate SN2 reaction with aniline substrates, the aldehyde 4.2 was reduced using sodium borohydride to alcohol 4.4 then brominated using HBr and was crystalized as the corresponding pyridine salt 4.5. Addition of 3-(para-NH$_2$-phenyl)-3-HP$\beta$L 2.44 along with 1-0 triethylamine resulted in quick formation of the desired pterin mimic-3-(para-NH$_2$-phenyl)-3-H$\beta$L adduct 4.6.

Figure 32:
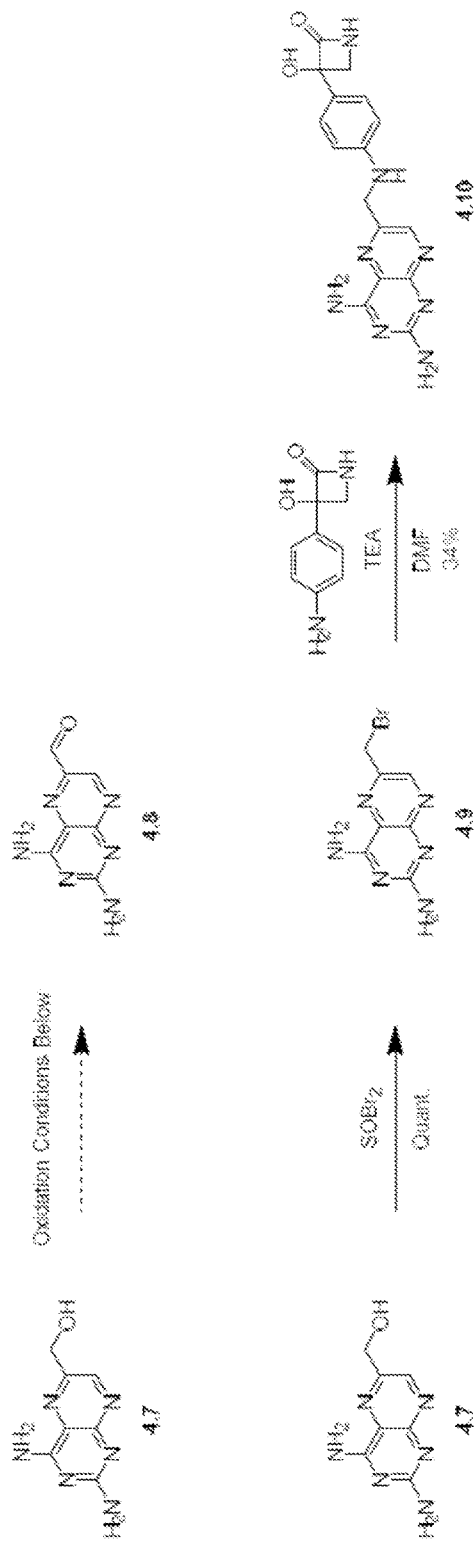
FIG. 32 is a schematic showing the synthetic efforts towards a pterin mimic-3-(para-NH$_2$-phenyl)-3-HβL using the pterin mimic from methotrexate in accordance with the present disclosure. Oxidation to an aldehyde for the purposes of reductive amination was unsuccessful, but bromination followed by SN2 displacement provided the desired product.

Attempts to directly oxidize 2,4-diamino-6-(hydroxymethyl)pteridine to the corresponding aldehyde 4.8 were unsuccessful (see e.g., FIG. 32 and TABLE 6).

TABLE 6

The synthetic efforts towards a pterin mimic-3-(para-NH$_2$-phenyl)-3-H$\beta$L using the pterin mimic from methotrexate.

| Reaction Attempt | Reagents | Solvent | Temperature | Result |
|---|---|---|---|---|
| 1 | 1.5 equiv DMP | DCM | 25° C. | No Reaction |
| 2 | 3 equiv DCC, 0.5 equiv H$_3$PO$_4$ | DMSO | 25° C. | No Reaction |
| 3 | 3 equiv DCC, 1.5 equiv H$_3$PO$_4$ | DMSO | 25° C. | No Reaction |

However, bromination with thionyl bromide followed by treatment with 3-(para-NH$_2$-phenyl)-3-H$\beta$L and triethylamine in dimethylformamide (DMF) readily provided pterin mimic-3-(para-NH$_2$-phenyl)-3-H$\beta$L adduct 4.10. This SN2 reaction is solvent dependent and does not proceed in dimethyl sulfoxide (DMSO) or dimethylacetamide (DMA). Both final compounds 4.6 and 4.10 can be purified by preparative RP-C18H$\beta$LC and recovered product was lyophilized to provide the final compounds for biochemical assays.

Biochemical Assay Results

Figure 33A:
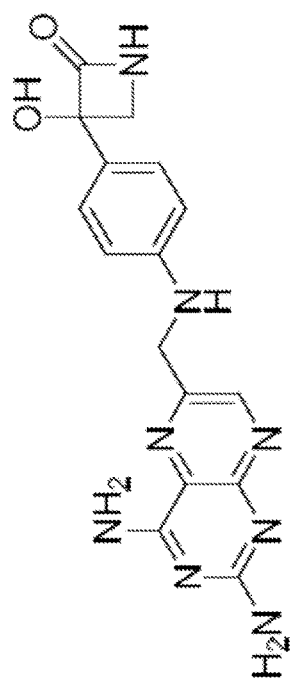
FIG. 33A-FIG. 33C is an exemplary embodiment showing the compounds used to investigate inhibition of DHFS in accordance with the present disclosure.
Figure 33B:
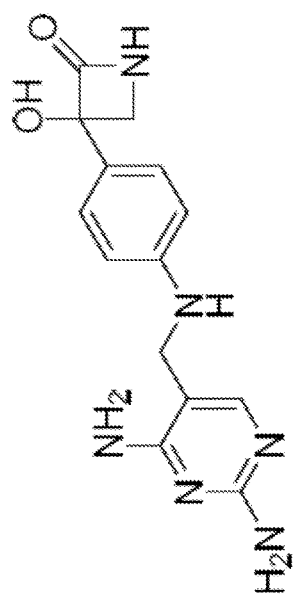
Figure 33C:
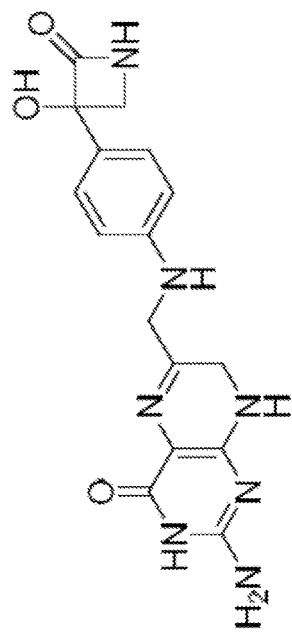

Three compounds were assessed as potential inhibitors in the DHFS steady state kinetics assay described herein (see e.g., FIG. 33A-FIG. 33C). The first two were the pterin mimic-3-(para-NH$_2$-phenyl)-3-H$\beta$L adducts 4.6 and 4.10 synthesized above, while the last was the pterin mimic-3-(para-NH$_2$-phenyl)-3-H$\beta$L adduct 4.11 that was chemoenzymatically synthesized herein.

Figure 34B:
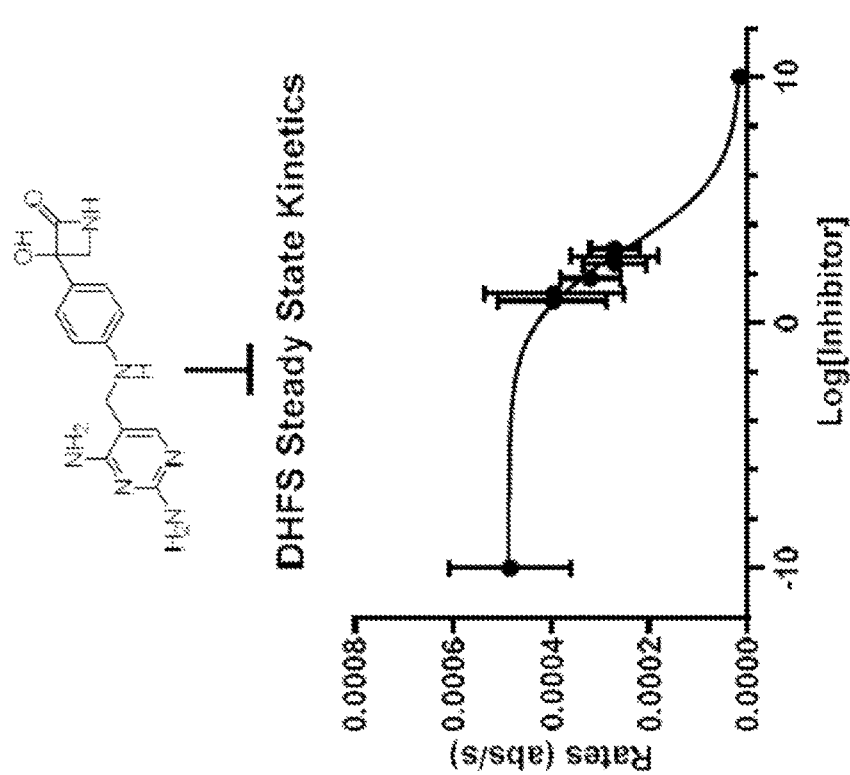
FIG. 34A-FIG. 34B is an exemplary embodiment showing IC50 curves for DHFS inhibition by two pterin mimic-3-(para-NH$_2$-phenyl)-3-HβL adducts in accordance with the present disclosure.
Figure 34A:
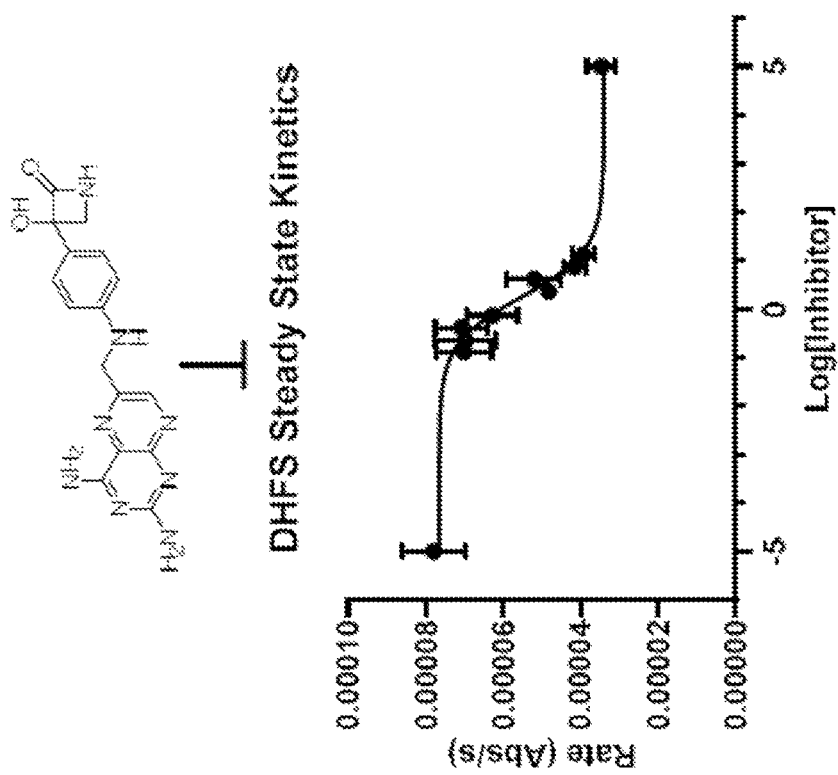
Figure 35A:
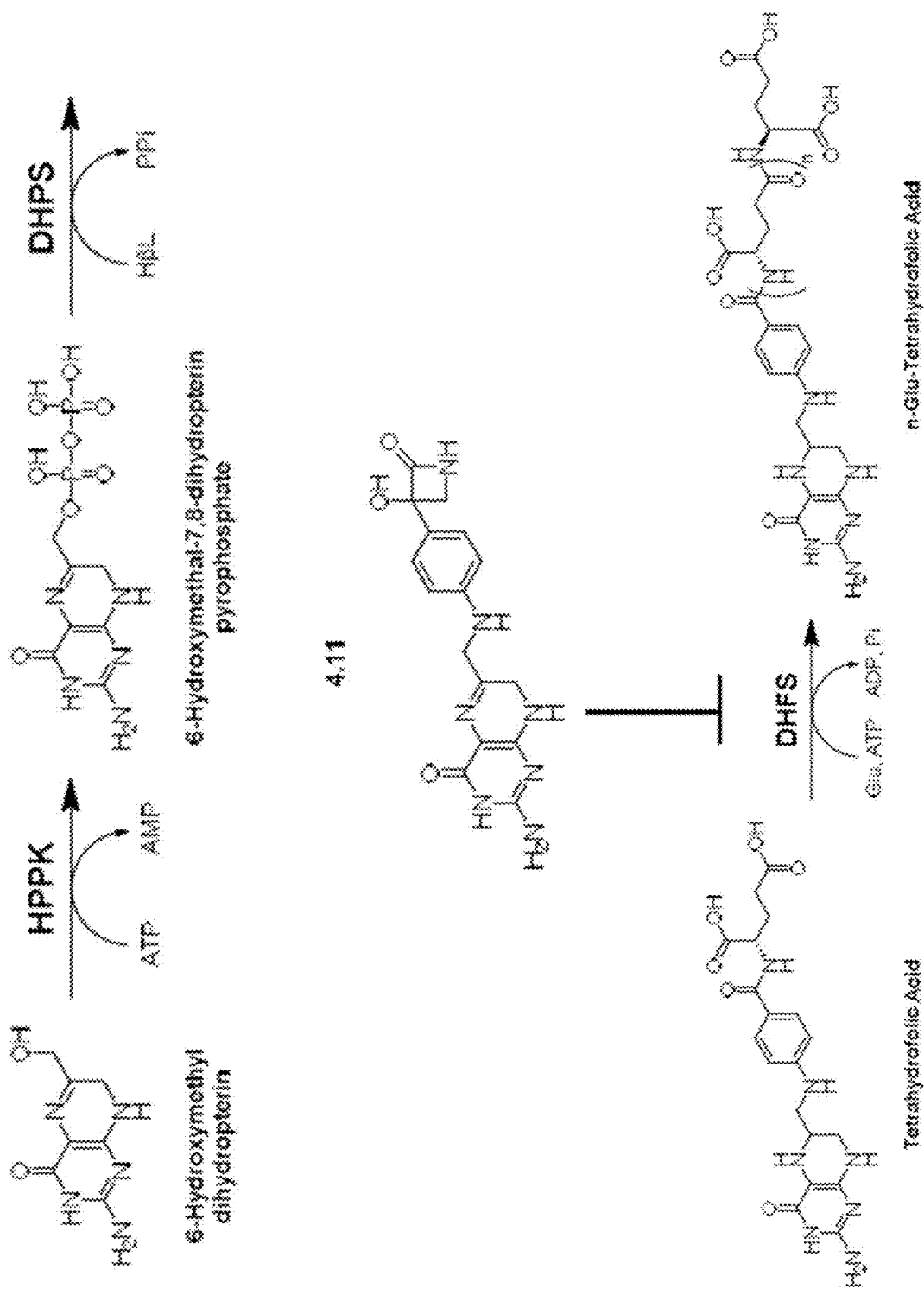
FIG. 35A-FIG. 35B is an exemplary embodiment showing inhibition of DHFS steady state kinetics with the chemoenzymatically derived pterin-3-(para-NH$_2$-phenyl)-3-HβL 4.11 in accordance with the present disclosure.
Figure 35B:
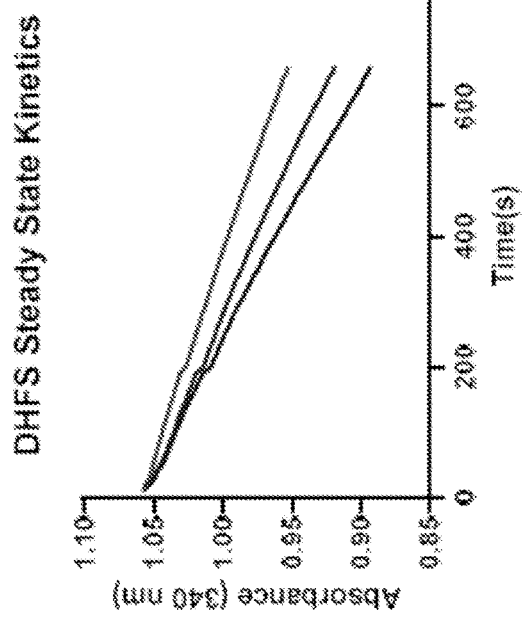

The two synthetically derived compounds 4.6 and 4.10 were dosed into the DHFS steady state kinetics assay at variable concentrations and the apparent reaction rates for each concentration were determined via continuous measurement of optical absorbance at 340 nm (see e.g., FIG. 34A-FIG. 34B). A dose-dependent inhibitory response to compound 4.10 was observed with an apparent IC50 of 1.77 µM±0.672 µM. In similar conditions, compound 4.6 had an apparent IC50 of 962 µM±1381 µM, indicating no apparent dose dependent inhibition of DHFS. Compound 4.10 showed close to 100% rate inhibition at double digit micromolar concentrations. Given the shared 3-(para-NH$_2$-phenyl)-3-H$\beta$L pharmacophore, DHFS has a clear preference for binding pterin mimetic preferring the methotrexate-derived pteridine over the trimethoprim-derived 2,4-diaminopyrimidine. To build up a suitable stock of compound 4.11, 3-(para-NH$_2$-phenyl)-3-H$\beta$L 2.44 was incubated overnight with HPPK/DHPS and their associated co-substrates at 37° C. This solution (which contained at most 150 µM of 4.11) was then dosed into the DHFS steady state kinetics assay in variable amounts (see e.g., FIG. 35A-FIG. 35B). Owing to the oxidation of the biological pterin moiety, accurate concentrations of 4.11 were not determined. However, as the same solution was used in variable amounts, the amount of 4.11 in each assay can be assumed to be related to how much of the solution was doped in versus a control solution containing everything except 3-(para-NH$_2$-phenyl)-3-H$\beta$L 2.44. In this way, a dose dependent inhibitory response is seen when 4.11 is added to DHFS (the three slopes are statistically different with P<0.0001), but an accurate IC50 may not be determined without knowing the starting concentration of the inhibitor. This finding is consistent with the conclusion that DHFS inhibitors may beneficially contain a pterin or pteridine heterocycle.

The Importance of the $\beta$-Lactam Ring

The central hypothesis herein is that the 3-H$\beta$L ring is an important structural feature needed to mimic the tetrahedral intermediate of an ATP-dependent carboxylate-amine ligase enzyme. In the case of tabtoxinine-$\beta$-lactam (T$\beta$L), as discussed herein, when the ring is hydrolyzed open, T$\beta$L lost all potency as an inhibitor of glutamine synthetase. The same could be true for compound 4.10, the newly minted 3-H$\beta$L based inhibitor of DHFS. It could also be that the hydrolyzed ring-opened version of 4.10 has similar if not near-identical potency.

Figure 36:
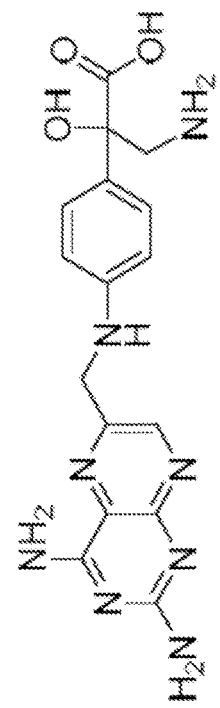
FIG. 36 is a schematic showing the acid catalyzed hydrolysis of the 3-HβL of compound 4.10 in accordance with the present disclosure.
Figure 36:
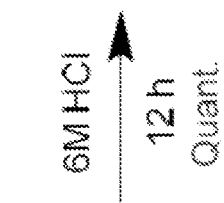
Figure 36:
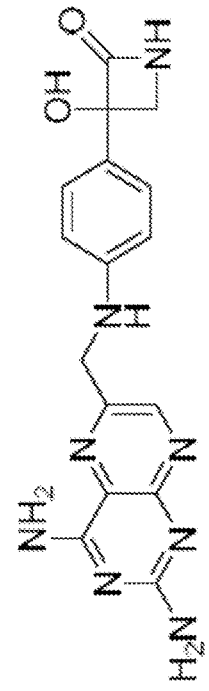

To prove that the 3-H$\beta$L pharmacophore is important, compound 4.10 was treated with strong aqueous acid to purposely ring-open the $\beta$-lactam (see e.g., FIG. 36). The now ring-opened compound 4.12 and ring-closed compound 4.10 were sent head-to-head in the DHFS steady state kinetics assay (see e.g., FIG. 37A-FIG. 37B). Across the same concentration gradient, ring-closed compound 4.10 had an apparent IC50 of 2.6 µM±1.1 µM while the ring-opened compound 4.12 had an apparent IC50 of 71.5 µM±62.1 µM. Notably, the higher concentrations of the ring-closed compound showed 100% DHFS inhibition with no product detected by LCMS of the reaction mixtures, while the DHFS reactions containing ring-opened compound dosed assay still showed some product by LCMS (see e.g., FIG. 38A-FIG. 38B). This result is consistent with the pteridine moiety being important for binding and the 3-H$\beta$L moiety being important for inhibition.

Is the 3-H$\beta$L being Phosphorylated by DHFS?

Figure 39:
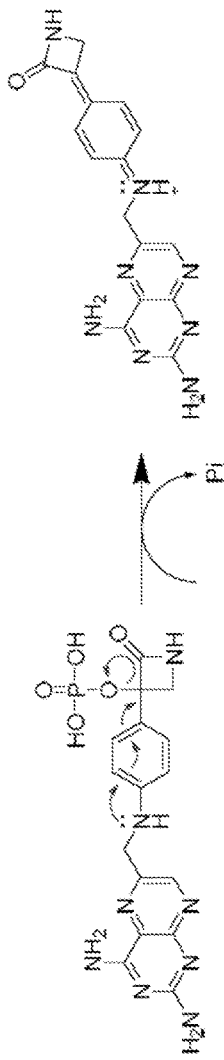
FIG. 39 is a schematic showing a mechanism for the production of a quinone-imine-methide following the proposed phosphorylation of the 3-hydroxy moiety of a 3-HβL inhibitor by DHFS in accordance with the present disclosure.
Figure 40A:
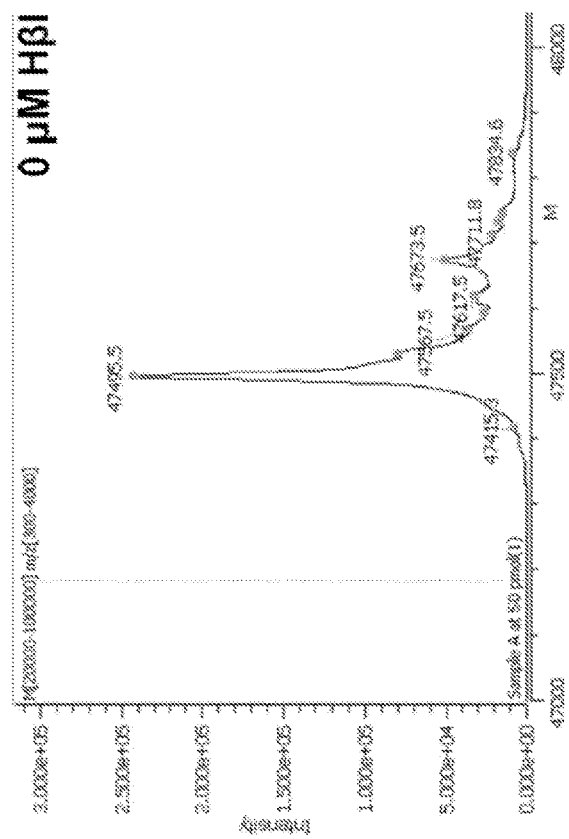
FIG. 40A-FIG. 40C is an exemplary embodiment showing protein mass spectrometry showing no 3-HβL—DHFS adducts formed with variable concentrations of the 3-HβL 4.10 in accordance with the present disclosure.
Figure 40B:
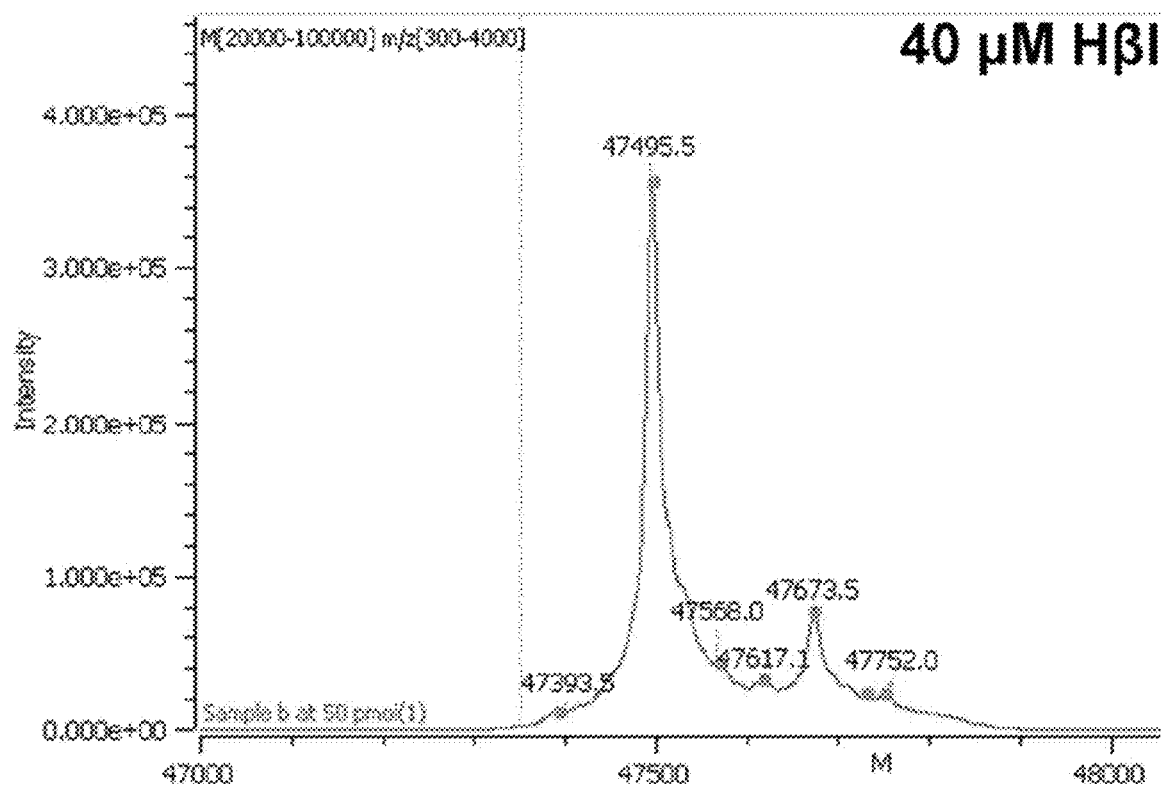
Figure 40C:
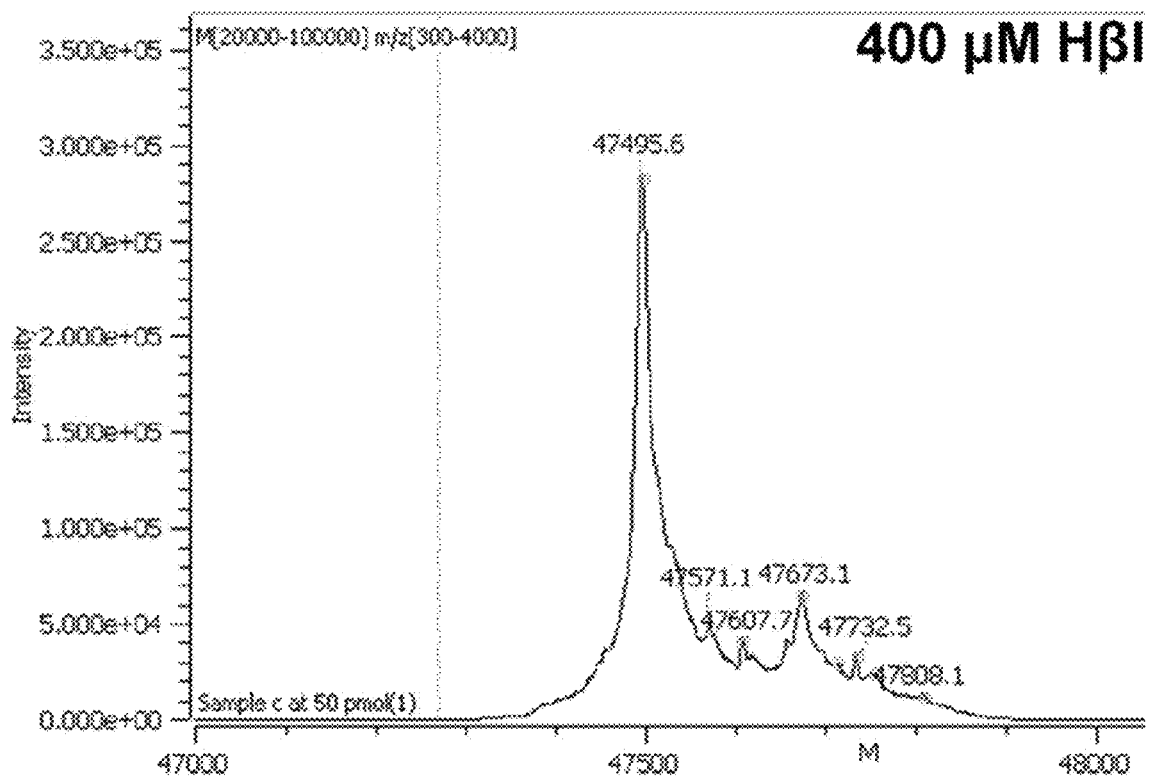

Once the importance of the $\beta$-lactam ring was established, the next questions to be answered were: 1) Why is the $\beta$-lactam important for biochemical potency?2) Is the mechanism for DHFS inhibition by a 3-H$\beta$L the same as T$\beta$L inhibition of glutamine synthetase (phosphorylation of the 3-hydroxyl group)?LCMS analysis of samples from DHFS kinetic assays never showed an apparent signal for m/z=433 corresponding to the expected [M+H]+ for the phosphorylated inhibitor 4.10); whereas, in the case of TβL and GS, the phosphorylated TβL could be seen by LCMS after precipitation of the enzyme inhibitor complex in methanolic water containing KCl. If DHFS is indeed phosphorylating the 3-hydroxyl group of the 3-HβL warhead, then why was it not detected by LCMS analysis? The possibility was considered that the higher concentrations of compound 4.10 resulting in 100% DHFS inhibition might be consistent with covalent modification of the enzyme by the inhibitor. This could happen by a variety of different mechanisms including the canonical β-lactam suicide inhibition mechanism through acylation of nucleophilic amino acid side chains. However, there is a potentially novel mechanism at play when considering the reactivity of an activated benzylic position of para-aniline derivatives. The presence of a leaving group at the benzylic position of para-anilines results in the formation of reactive quinone-imine-methide species. If the 3-hydroxy group of inhibitor 4.10 is phosphorylated in the DHFS active site, it could serve as a leaving group leading to spontaneous formation of a quinone-imine-methide that might react with nearby amino acid side chains. This transformation could also take place within the mass spec, making detection of the phosphorylated inhibitor impossible (see e.g., FIG. 39). Herein, the benzylic carbon of the aniline ring was found to be very active in expelling leaving groups during the Henry reaction, which is consistent with the potential for quinone-imine-methide formation. The Powers group was previously able to detect the adduct of thrombin with an inhibitor (4-chloro-3-ethoxy-7-guanidinoisocoumarin) which arose from a quinone-imine-methide formation followed by a covalent reaction with the thrombin active site. Quinone methide species can be trapped by biological nucleophiles including glutathione. The DHFS reactions contained dithiothreitol (DTT) as a reducing agent that can also serve as a nucleophilic thiol. Hence, the LCMS samples were analyzed for the presence of potential adducts between a quinone-iminemethide intermediate and DTT (a [M+H]+ of 489) but nothing was found. There is precedent for quinone-imine-methides to form covalent adducts with both DNA and enzyme active sites. As such, solutions of DHFS were made with variable amounts of inhibitor 4.10 and submitted for protein mass spectrometry. However, no apparent peaks corresponding to DHFS+ 334 mass units (the molecular weight for the quinone-imine-methide) were found (see e.g., FIG. 40A-FIG. 40C). The LCMS samples were also analyzed for the presence of a reaction product between the 3-HβL and L-Glu, but no masses which could match this description were found. If the 3-HβL was getting phosphorylated in the active site of DHFS, then it should, in principle, be possible to detect a difference in 31 P NMR signals for phosphates in a solution of DHFS and inhibitor. To this end, standard solutions of ATP, ADP, DHFS, and 4.10 were made, along with solutions containing 4.10 and DHFS (along with its associated cofactors) were made. These samples were subjected to 31P NMR conditions in 10% D2O with the intention of seeing a new phosphorus peak corresponding to a phosphate on the 3-HβL.

Whole Cell Antibacterial Susceptibility Test with Inhibitor 4.10

With in vitro activity confirmed against DHFS and apparent potency established for inhibitor 4.10, the next step was to determine if inhibition of bacterial cell growth could be demonstrated. Bacterial growth curves were determined for E. coli using two compounds—inhibitor 4.10 and trimethoprim (positive control). A 96-well plate format was used to achieve serial dilution of the test compounds and included a DMSO control to simulate the concentration of DMSO required to solubilize the test compounds in the growth medium (not shown). No significant inhibition of bacterial growth was observed in the presence of inhibitor 4.10 beyond that observed for the DMSO control. Trimethoprim showed a MIC (minimum inhibitory concentration) of 2 µM. Given that trimethoprim and inhibitor 4.10 have a shared mechanism (inhibition of folate biosynthesis, albeit by acting on different protein targets) similar whole cell activity was expected. The lack of whole cell activity could be due in part by a lack of cell permeability, which is a common problem for antibiotic molecules given the difficulty of passive diffusion through the thick bacterial cell envelope.

Figure 41:
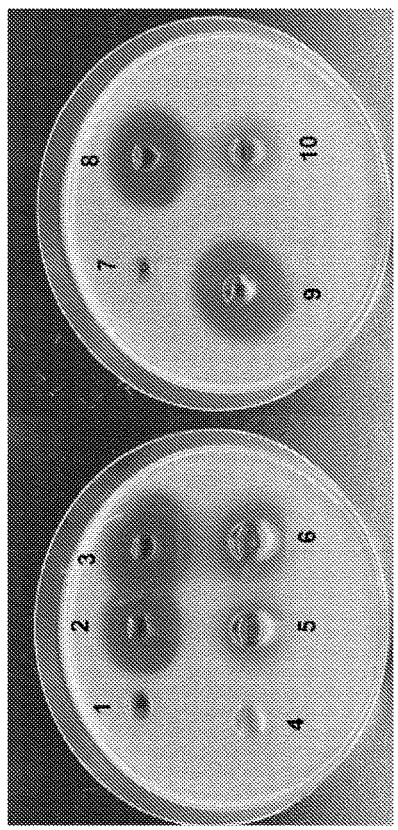
FIG. 41 includes images showing agar diffusion assay using E. coli and variable concentrations and combinations of 3-HβL 4.10, sulfamethoxazole (SMX), and trimethoprim (TMP) in accordance with the present disclosure. There is no apparent effect on E. coli growth by 3-HβL 4.10 either alone or in combination with SMX or TMP respectively.
Figure 42:
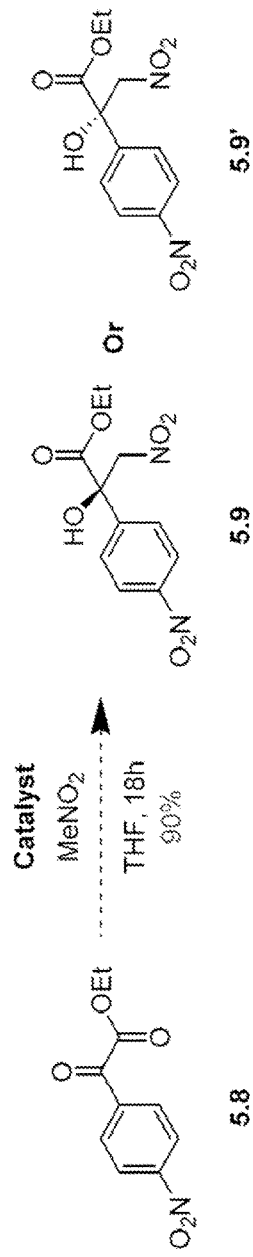
FIG. 42 is a schematic showing asymmetric Henry reaction possibilities to expand SAR in accordance with the present disclosure.
Figure 42:
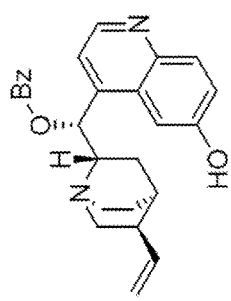
Figure 42:
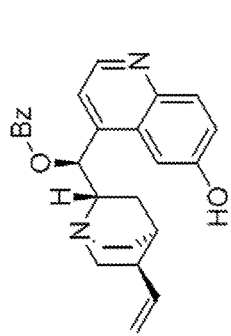
Figure 43:
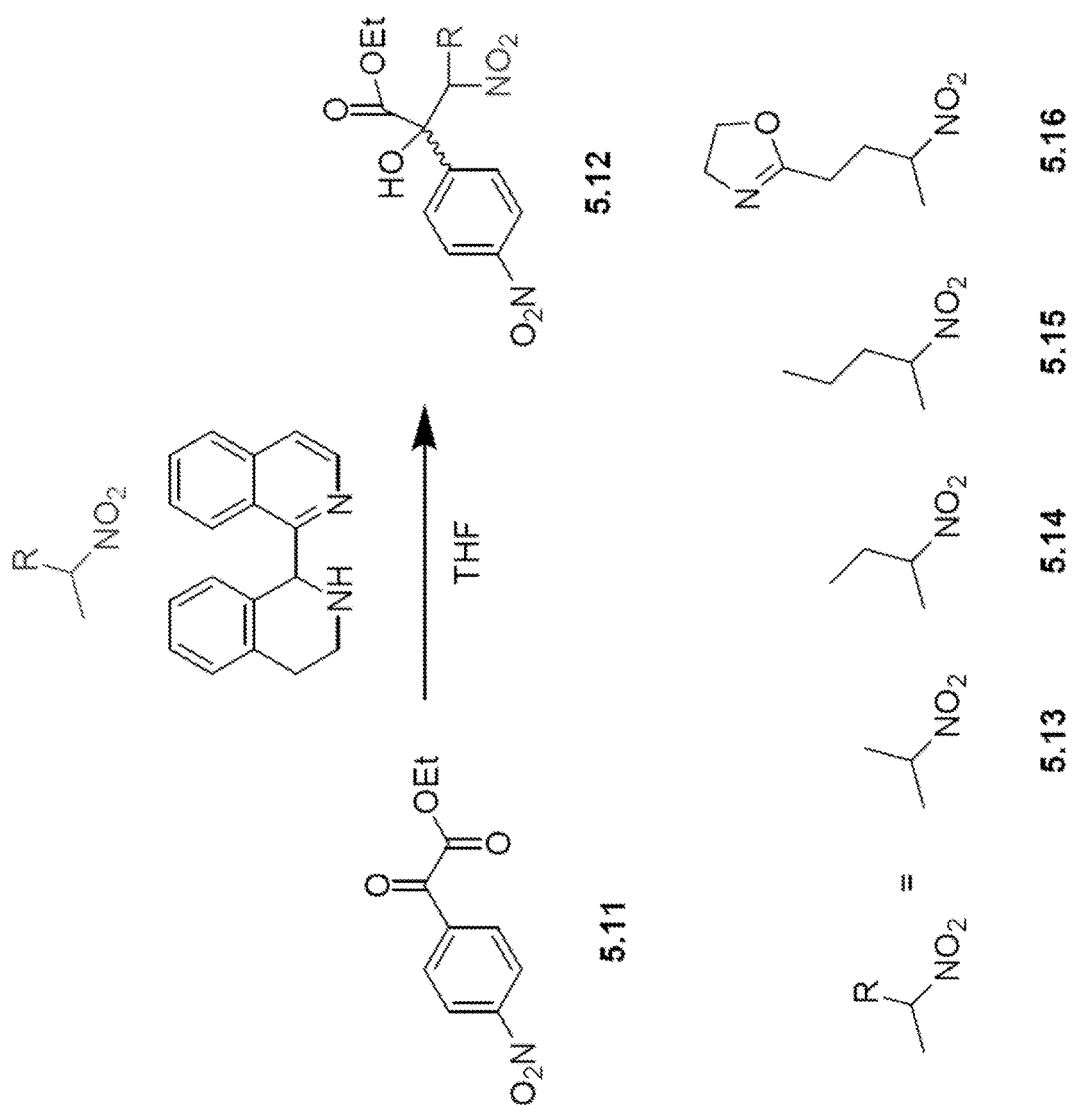
FIG. 43 is a schematic showing Henry reaction substrate scope expansion to facilitate 4C substitution on the 3-HβL pharmacophore in accordance with the present disclosure.
Figure 44A:
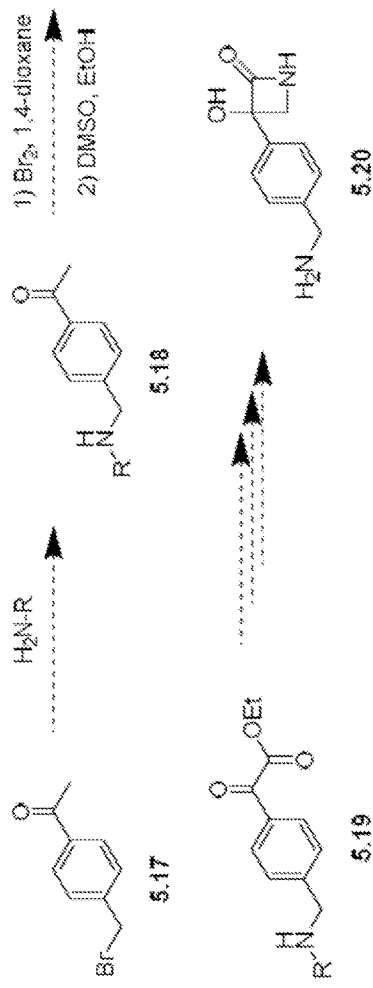
FIG. 44A-FIG. 44C is an exemplary embodiment showing proposed synthesis of 3-HβL inhibitors with expanded pterin-3-HβL linkers in accordance with the present disclosure.
Figure 44B:
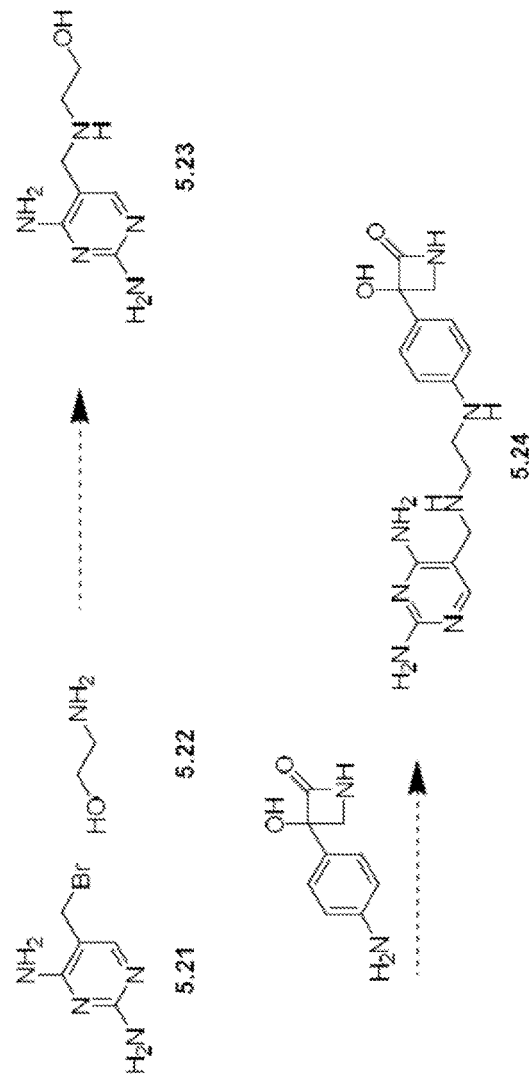
Figure 44C:
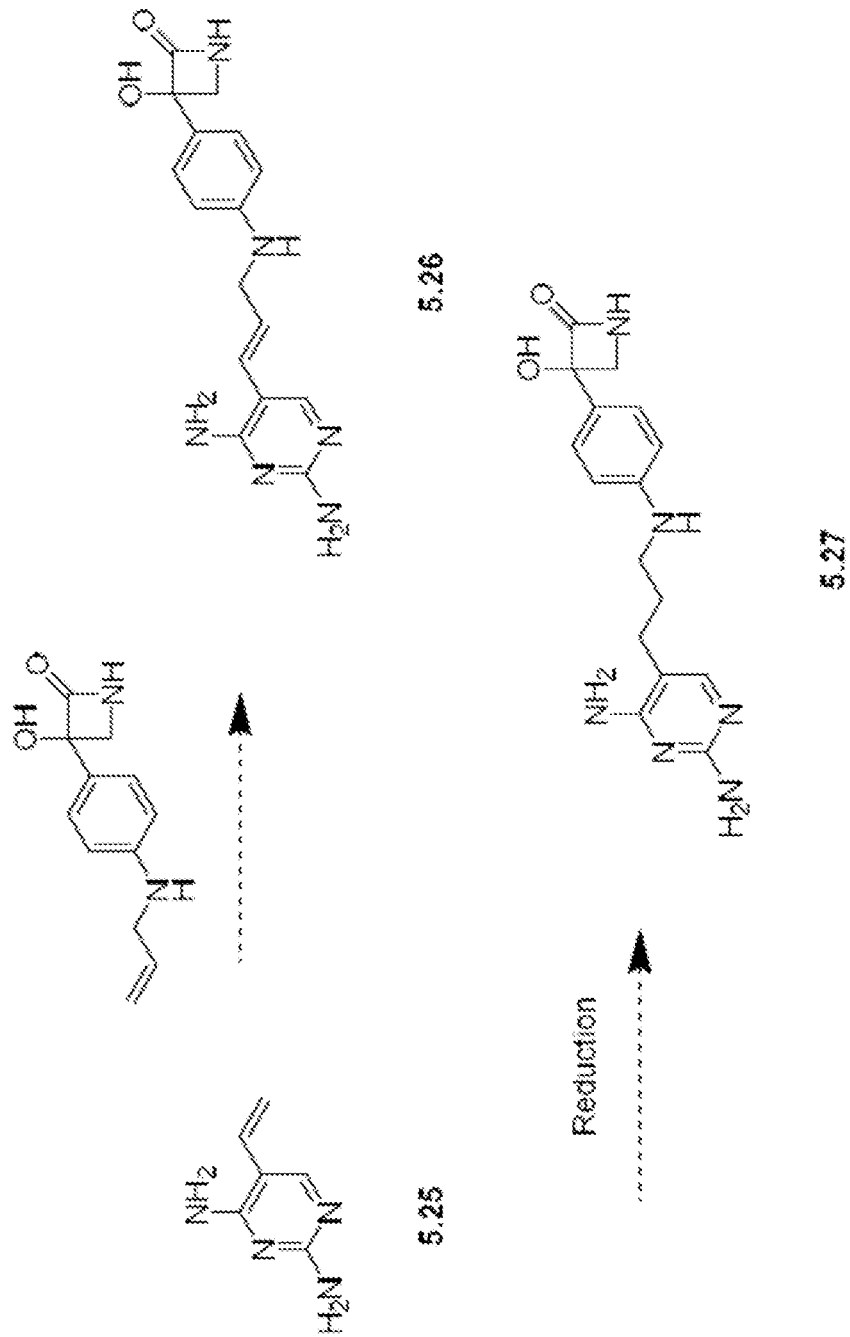
Figure 46A:
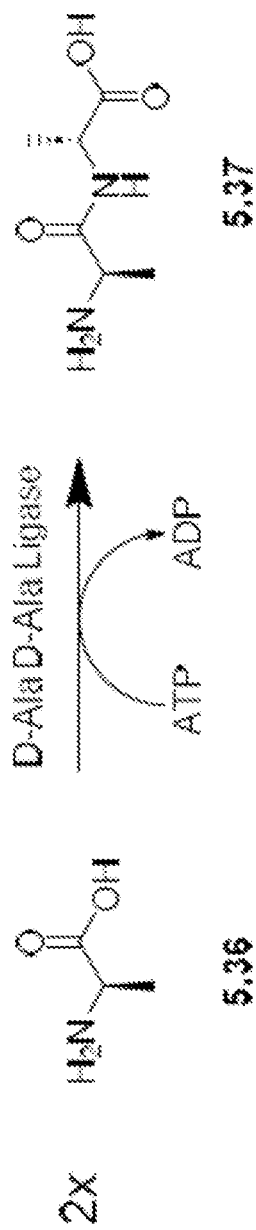
FIG. 46A-FIG. 46D is an exemplary embodiment showing D-alanine D-alanine Ligase (DDL) proposal in accordance with the present disclosure.
Figure 46B:
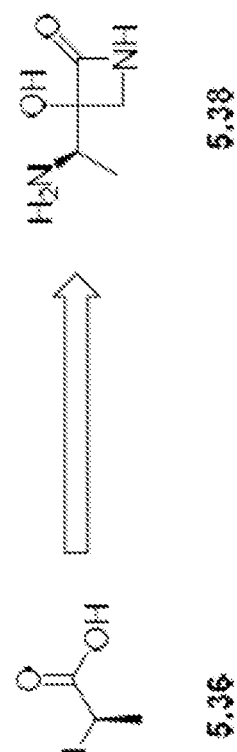
Figure 46C:
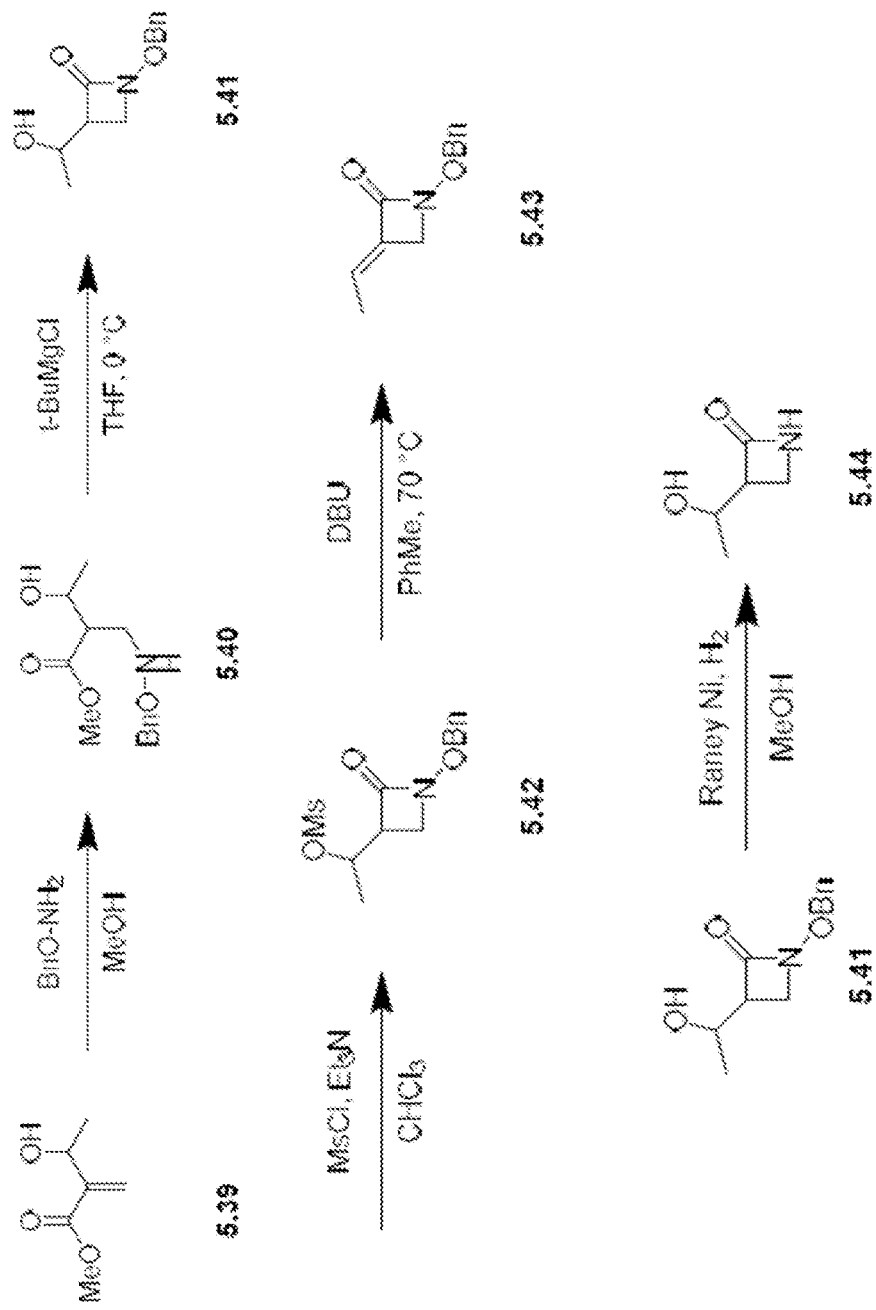
Figure 46D:
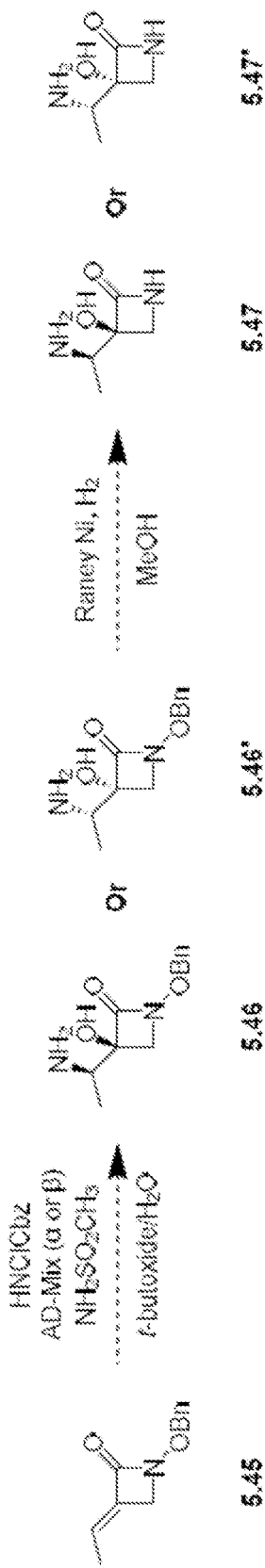
Figure 47A:
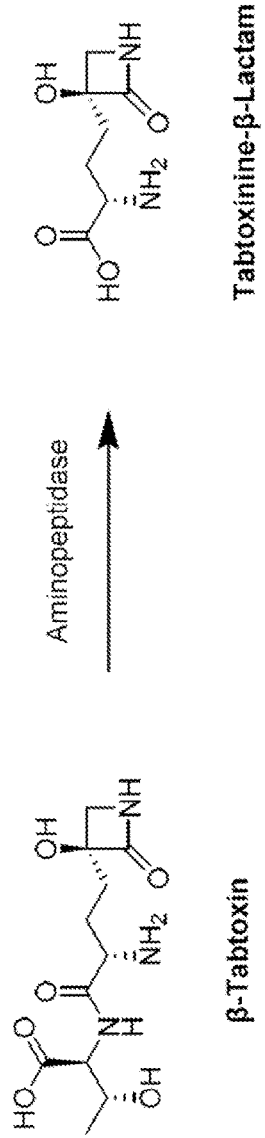
FIG. 47A-FIG. 47B is an exemplary embodiment showing aminopeptidase cleavage of prodrugs in accordance with the present disclosure.
Figure 47B:

Inhibitor 4.10 was also used alongside sulfamethoxazole and trimethoprim and in combination with sulfamethoxazole and trimethoprim respectively, in an agar diffusion antibacterial susceptibility assay (see e.g., FIG. 41 and TABLE 11).

TABLE 11

Agar diffusion assay using E. coli and variable concentrations and combinations of 3-HβL 4.10, sulfamethoxazole (SMX), and trimethoprim (TMP).

| Well | Compound Concentrations | Zone of Inhibition |
|---|---|---|
| 1 | DMSO | 0 mm |
| 2 | 3.52 mg/mL TMP | 39.6 mm |
| 3 | 15 mg/mL TMP | 45.3 mm |
| 4 | 3.52 mg/mL HβL | 0 mm |
| 5 | 3.52 mg/mL SMX | 23.2 mm |
| 6 | 15 mg/mL SMX 25.9 mm | 25.9 mm |
| 7 | DMSO | 0 mm |
| 8 | 3.52 mg/mL TMP + 3.52 mg/mL SMX | 44.3 mm |
| 9 | 3.52 mg/mL HβL + 3.52 mg/mL TMP | 40.3 mm |
| 10 | 3.52 mg/mL HβL + 3.52 mg/mL SMX | 21.3 mm |

Given that sulfamethoxazole and trimethoprim display synergistic antibacterial activity, it was hypothesized that the same might be true for combinations with inhibitor 4.10. Although both sulfamethoxazole and trimethoprim showed clear zones of bacterial growth inhibition, no bacterial growth inhibition was observed for inhibitor 4.10. No apparent synergistic effect was observed when inhibitor 4.10 was used in combination with either sulfamethoxazole or trimethoprim. As described for the liquid bacterial growth assays, cell permeability might be a limitation of inhibitor 4.10 at this stage. Lack 1-9 of cell permeability has been observed for many antifolates and was recently addressed by a series of folate mimics that contain lipophilic side chains to enhance cell permeability. Such an approach could be applied in theory to inhibitor 4.10.

Discussion

The synthesis of pterin-mimic-3-(para-NH$_2$-phenyl)-3-HPβL adducts failed by the reductive amination pathway but was successful by the SN2 displacement of a benzyl bromide derivative. Purifying these compounds by prep-RPC18-HβLC limited the reaction scale, but in principle, it may be scaled out by the current method or scaled up using standard RPC18 column chromatography. The solubility issues that arise when working with pteridines may be leveraged for precipitation, trituration, or crystallization from non-polar solvents, but this was not attempted on scale. Nevertheless, the DHFS assay requires micrograms of compound per reaction, so it was simple to acquire enough inhibitor once the conditions for purification were established.

The findings herein are consistent with the central hypothesis, that the 3-HβL pharmacophore from TβL could be repurposed to create inhibitors of ATP-dependent carboxylate-amine ligase enzymes similar to the well characterized inhibition of GS by TβL. The 3-HβL pharmacophore is a powerful warhead to bind to enzymes that catalyze this type of reaction. The Hyde group, in their investigation of the two phosphinic acid-based inhibitors of DHFS, found that reduction of the pterin-mimic moiety prior to a kinetic assay could drastically improve the inhibition profile, and while this was explored (not shown here), reduced pterin concentration reproducibility stifled further progress on this inhibitor series. Nevertheless, the 3-HβL inhibitor 4.10 is a tight-binding inhibitor of DHFS under in vitro conditions, and the structural integrity of the β-lactam is pivotal to achieving potent inhibition of the DHFS-catalyzed reaction. The amino-pyrimidine heterocycle derived from the trimethoprim scaffold proved insufficient to correctly position 3-HβL moiety deep enough in the active site (as the modeling predicted), but investigations into the linker size might be able to mediate this while maintaining the smaller pterin-mimic core.

The lack of whole cell activity is likely due to an inability of the compound to permeate the bacterial cell envelope. Given the pterin-mimic in trimethoprim is capable of permeating the bacterial cell envelope to reach the cytoplasmic DHFR target, a logical extension of inhibitor design would be to make a longer linker from the single ring pterin mimic to the aniline linker, mitigating the smaller ring size to 3-HβL distance afforded by the single ring pterin mimic while harnessing the ability of this heterocycle to enter bacterial cells. Possible synthetic routes to this type of compound are discussed below.

The detection of the hypothesized Pi-3-HβL was unsuccessful by mass spectrometry and similarly unsuccessful by 31 P NMR. No new phosphorous NMR peaks were shown in the samples containing DHFS and 4.10. However, the concentration of ATP, DHFS, and 4.10 were quite low in the conditions that allow DHFS to work, resulting in a very high signal to noise ratio in the 31 P NMR. The high signal to noise ratio necessitated long collection times for the NMR, so if a hypothesized new 31 P NMR peak arose, and it was transient (on the order of only existing for minutes at a time) the experimental parameters tried would not show the existence of this peak. Adjusting the concentration of ATP, DHFS, and 4.10 to be much higher may allow for shorter collection times, and as a result, show a more transiently existing new phosphate peak.

Conclusion

The adaptation of the 3-HβL pharmacophore to a novel system shows its potential to open a new chapter in β-lactam antibiotics. The 3-HβL compound described here is capable of 100% inhibition of DHFS at low micromolar concentrations, similar to the potency observed for the inhibition of GS by the natural product TβL. The mechanism of action for inhibition of this new system is still being studied, but the intact 3-HβL ring is important for potency as hypothesized. DHFS has preferences for pterin-ring mimics, with a two-ring system pteridine being preferable to a single ring amino-pyrimidine. Understanding the mechanism of DHFS inhibition by 3-HβLs is integral to validating DHFS as a target for inhibition of the folate pathway that can be translated to therapeutic leads against antibiotic resistant bacterial pathogens. While no new compounds investigated had potency against whole cell bacterial growth, a potential combination of the new inhibitors that has a suitably long linker and an amino-pyrimidine ring might allow for increase cell wall permeability while maintaining inhibitory potency.

The reproducibility of the steady-state kinetics assay for DHFS developed herein was demonstrated. Subtle changes in DHFS activity can be seen without the limitations of end-point assays previously used for DHFS activity. This, coupled with the scalable synthesis of the 3-HβL core developed herein, provide the foundation for an SAR exploration around the pterin mimic, the linker, and even substituents on the 3-HβL ring itself.

Materials and Methods

All chemicals and solvents were purchased from reputable vendors (ex. Sigma Aldrich, Oakwood, Enamine, Thermo Fisher). All prep-HβLC was performed using an Agilent/HP 1050 quaternary pump module with an Agilent/HP MWD module with a Phenomenex Luna 10u C18(2) 100A column, 250×21.20 mm, 10 μm with guard column. All LCMS was performed on an Agilent 6130 quadrupole LC-MS with G1313 autosampler or G1367B autosampler, G1315 diode array detector, and 1200 series solvent module. A Phenomenex Gemini C18 column, 50×2 mm, 5 μm with guard column was used for all LC-MS separations. Mobile phases for prep-HβLC and LCMS were 0.1% formic acid in (A) $H_2O$ and (B) $CH_3CN$, and data were processed using ChemStation software (Agilent). NMR was performed on either an Agilent DD2 600 MHz, an Agilent DD2 500 MHz, or a Varian Unity Plus 300 MHz instrument and data was processed using MestraNova. All optical absorption plate readings were performed on either a Spectra Max Plus 384 or a Fisher AccuSkan Go.

Synthesis

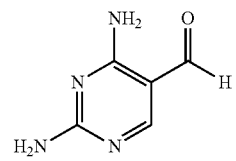

2,4-diaminopyrimidine-5-carbaldehyde (4.2): To a solution of 2,4-diaminopyrimidine-5-carbonitrile (250 mg, 1.85 mmol) in 2.5 mL of formic acid was added Raney Ni (312.5 mg in $H_2O$). The reaction flask was fitted with a reflux condenser and the mixture was heated to 100° C. for 18 h. The solution was cooled to 25° C. then filtered through celite and concentrated under pressure. The residue was dissolved in a minimum of 30% ammonia in water then placed in an ice water bath until a solid formed. The mixture was filtered to yield 181.3 mg (71% yield) of a yellow solid. 1H NMR (300 MHz, Methanol-d4) δ 9.50 (s, 1H), 8.29 (s, 1H). [M+H]+=138+1=139.

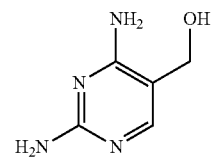

(2,4-diaminopyrimidin-5-yl)methanol (4.4): To a suspension of 2,4-diaminopyrimidine-5-carbaldehyde (126.8 mg, 0.919 mmol) in 5 mL $H_2O$ was added NaBH4 (104 mg, 2.76 mmol). The reaction flask was fitted with a reflux condenser then heated to 50° C. while stirring for 4 h. The mixture was concentrated under pressure and the residue was suspended in a minimum of H₂O (1 mL). The suspension was stirred for 10 min then put a −20° C. freezer overnight. The mixture was filtered and washed with cold water to yield a solid. 1H NMR (300 MHz, DMSOd6) δ 7.57 (s, 1H), 6.03 (s, 2H), 5.76 (s, 2H), 4.74 (t, J=5.5 Hz, 1H), 4.19 (d, J=5.4 Hz, 2H). [M+H]+=140+1=141.

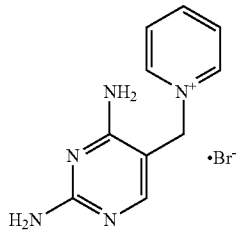 [SMILES: Nc1ncc(C[n+]2ccccc2)c(N)n1 ; [Br-]]

1-((2,4-diaminopyrimidin-5-yl)methyl)pyridin-1-ium bromide (4.5): A solution of (2,4-diaminopyrimidin-5-yl)methanol (53.22 mg, 0.38 mmol) in 1 mL AcOH was heated to 50° C. to dissolve the added (2,4-diaminopyrimidin-5-yl)methanol. The solution was allowed to cool then HBr (798 µL of 33% HBr in AcOH) was added dropwise. The solution was heated to 60° C. while stirring for 3 h. The solution was cooled to 25° C. then concentrated under pressure. The residue was taken up in 1.145 mL of DMF and pyridine (122 µL, 1.514 mmol) was added. The solution was stirred for 2 h at 25° C. then treated with 1.348 mL of cold DCM and filtered. The solid was washed with cold DCM to yield 97.5 mg (71.2% yield) of salt. 1H NMR (300 MHz, DMSO-d6) δ 9.02 (d, J=6.1 Hz, 2H), 8.63 (dd, J=8.4, 7.1 Hz, 1H), 8.16 (t, J=7.2 Hz, 2H), 7.95 (s, 1H), 5.62 (s, 2H).

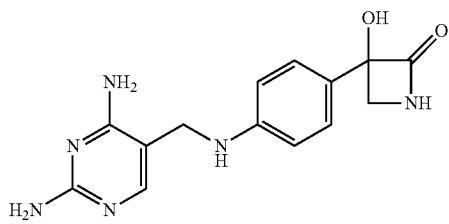

3-(4-(((2,4-diaminopyrimidin-5-yl)methyl)amino)phenyl)-3-hydroxyazetidin-2-one (4.6): To a solution of 3-(4-aminophenyl)-3-hydroxyazetidin-2-one (3.31 mg, 0.0186 mmol) in 1 mL of DMF was added 1-((2,4-diaminopyrimidin-5-yl)methyl)pyridin-1-ium bromide (8.04 mg, 0.0223 mmol) and triethylamine (TEA) (13 µL, 0.0933 mmol). The solution was degassed with argon then stirred at 25° C. for 48 h. The solution was concentrated under pressure and the residue was run on an HβLC (5-95% ACN w/0.1% Formic Acid in Water with 0.1% Formic acid) to yield 3.7 mg (66% yield) of a yellow oil. 1H NMR (500 MHz, Methanol-d4) δ 7.55 (s, 1H), 7.33 (d, J=8.6 Hz, 2H), 6.66 (d, J=8.7 Hz, 2H), 4.10 (s, 2H), 3.56 (d, J=5.8 Hz, 1H), 3.49 (d, J=5.6 Hz, 1H). [M+H]+=300+1=301.

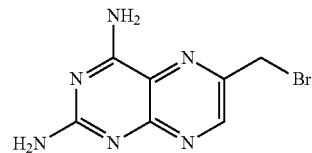 [SMILES: Nc1nc(N)c2nc(CBr)cnc2n1]

6-(bromomethyl)pteridine-2,4-diamine (4.9): A solution of (2,4-diaminopteridin-6-yl)methanol (150 mg, 0.781 mmol) in 3 mL SOBr2 was stirred in the dark at 25° C. for 72 h. The solution was concentrated under pressure then the residue was taken up in 5 mL of toluene. The mixture was stirred for 18 h in the dark the filtered to obtain a quantitative yield of solid. 1H NMR (300 MHz, TFA/DMSO) b 9.04 (s, 1H), 4.65 (s, 2H). [M+H]+=255+1=256.

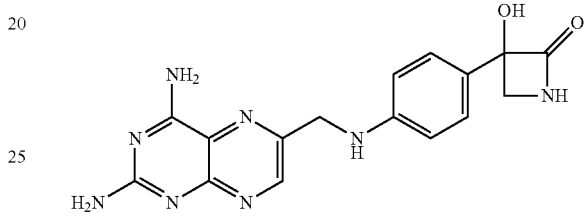

3-(4-(((2,4-diaminopteridin-6-yl)methyl)amino)phenyl)-3-hydroxyazetidin-2-one (4.10): To a solution of 3-(4-aminophenyl)-3-hydroxyazetidin-2-one (3.31 mg, 0.0186 mmol) in 1.5 mL DMF was added 6-(bromomethyl)pteridine-2,4-diamine (9.21 mg, 0.0361 mmol) and triethylamine (TEA) (9.31 uL, 0.06678 mmol). The solution was degassed with argon then stirred for 48 h in the dark. The solution was concentrated under pressure and the residue was run on an HβLC (5-95% ACN w/0.1% Formic Acid in Water with 0.1% Formic acid) to yield 2.2 mg (33.6% yield). 1H NMR (500 MHz, DMSO-d6) δ 8.69 (s, 1H), 8.07 (s, 1H), 7.23-7.15 (m, 2H), 6.75-6.67 (m, 2H), 6.37 (t, J=5.5 Hz, 1H), 6.34 (s, 1H), 4.43 (d, J=5.4 Hz, 2H), 3.37 (d, J=5.4 Hz, 1H), 3.31 (d, J=5.4 Hz, 2-5H). 13C NMR (151 MHz, DMSO-d6) δ 171.14, 162.82, 155.18, 149.51, 147.67, 146.14, 128.33, 128.04, 127.49, 126.26, 112.11, 86.40, 52.79, 45.66. COSY, HSQC, and HMBC correlations in TABLE 12. [M+H]+=352+1=353.

TABLE 12

2D NMR correlations for compound 4.10.

| Atom | δ (ppm) | COSY | HSQC | HMBC |
|---|---|---|---|---|
| 1 N | | | | |
| H | 6.43 | 2', 2" | | 16, 20 |
| 2 C | 45.46 | | 2' | |
| H' | 4.42 | 1 | 2 | 3, 4, 15 |
| H" | 4.44 | 1 | | 3, 4, 15 |
| 3 C | 145.37 | | | 2', 2", 4 |
| 4 C | 148.74 | | 4 | 2', 2" |
| H | 8.76 | | 4 | 3, 6 |
| 5 N | | | | |
| 6 C | 154.41 | | | 4 |
| 7 N | | | | |
| 8 C | 162.05 | | | |
| 9 N | | | | |
| H2 | | | | |
| 10 N | | | | |
| 11 C | 162.05 | | | |

TABLE 12-continued

2D NMR correlations for compound 4.10.

2D Assignments

| Atom | δ (ppm) | COSY | HSQC | HMBC |
|---|---|---|---|---|
| 12 N | | | | |
| H2 | | | | |
| 13 C | 127.56 | | | |
| 14 N | | | | |
| 15 C | 146.9 | | | 2', 2", 17, 19 |
| 16 C | 111.85 | | 16 | 1, 20 |
| H | 6.7 | 17 | 16 | 18, 20 |
| 17 C | 125.49 | | 17 | 19 |
| H | 7.2 | 16 | 17 | 15, 19, 21 |
| 18 C | 127.27 | | | 16, 20, 22', 23 |
| 19 C | 125.49 | | 19 | 17 |
| H | 7.2 | 20 | 19 | 15, 17, 21 |
| 20 C | 111.85 | | 20 | 1, 16 |
| H | 6.7 | 19 | 20 | 16, 18 |
| 21 C | 85.63 | | | 17, 19, 22', 22", 23 |
| 22 C | 52.92 | | 22', 22" | 23 |
| H' | 3.44 | 22" | 22 | 18, 21, 24 |
| H" | 3.39 | 22' | 22 | 21, 24 |
| 23 N | | | | |
| H | 8.07 | | | 18, 21, 22 |
| 24 C | 170.37 | | | 22', 22" |
| 25 O | | | | |
| H | 6.41 | | | |
| 26 O | | | | |

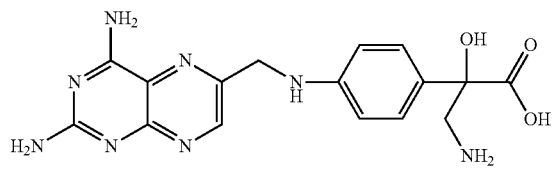 [SMILES: NCC(O)(C(=O)O)c1ccc(NCc2cnc3nc(N)nc(N)c3n2)cc1]

3-amino-2-(4-(((2,4-diaminopteridin-6-yl)methyl)amino) phenyl)-2-hydroxypropanoic acid (4.12): 3-(4-(((2,4-diaminopteridin-6-& yl)methyl)amino)phenyl)-3-hydroxyazetidin-2-one (1.1 mg, 0.003125 mmol) was dissolved in 275 μL of 6M HCl (aq). The solution was stirred for 12 h then concentrated under pressure to yield 3-amino-2-(4-(((2,4-diaminopteridin-6-yl)methyl)amino)phenyl)-2-hydroxypropanoic acid as the HCl salt in quantitative yield. [M+H]+=370+1=371.

HPPK/DHPS Chemoenzymatic Synthesis and DHFS Inhibition Assay

TABLE 13

Biochemical conditions for the DHFS kinetics assay using HPPK/DHPS to generate the DHFS substrate.

| | Final Concentration |
|---|---|
| Solution A | |
| MgCl$_2$ | 5 mM |
| β-mercaptoethanol | 20 mM |
| Bovine Serum Albumin | 1 mg/mL |
| 6-hydroxymethyl-7,8-dihydropterin | 150 μM |
| 3-HβL | 1 mM |
| ATP | 300 μM |
| HPPK | 40 μg/mL |
| DHPS | 40 μg/mL |
| Tris Buffer pH = 7.5 | 10 mM |
| Solution B | |
| MgCl$_2$ | 5 mM |
| β-mercaptoethanol | 20 mM |
| Bovine Serum Albumin | 1 mg/mL |
| 6-hydroxymethyl-7,8-dihydropterin | 150 μM |
| 3-HβL | — |
| ATP | 300 μM |
| HPPK | 40 μg/mL |
| DHPS | 40 μg/mL |
| Tris Buffer pH = 7.5 | 10 mM |
| Solution C | |
| PEP | 600 μM |
| NADH | 600 μM |
| PK | 20 units/mL |
| LDH | 30 units/mL |
| Tris Buffer pH = 7.5 | 100 mM |
| Solution D | |
| Tetrahydrofolic Acid | 150 μM |
| (L)-Glutamate | 300 μM |
| ATP | 300 μM |
| DHFS | 400 μg/mL |
| Tris Buffer pH = 7.5 | 100 mM |

| | Vol A | Vol B | Vol C | Vol D |
|---|---|---|---|---|
| Well 1 | 100 μL | 50 μL | 50 μL | 50 μL |
| Well 2 | 50 μL | 100 μL | 50 μL | 50 μL |
| Well 3 | 0 μL | 150 μL | 50 μL | 50 μL |

Stock solutions of all reagents were made using 100 mM Tris-buffer (pH=7.5) an stored in fractions in a −80° C. freezer until use. On day 1, 600 μL of Solution A and 900 μL of solution B were made and placed in an incubator at 37° C. for 18 & h. On day 2, 500 μL of Solution C and Solution D were made. Solutions A and B were taken out of the incubator. The wells of a quartz 96-well plate were flushed with argon and the well composition in TABLE 13 were made in triplicate. The 96-well plate was put into a UV/Vis plate reader and the optical absorbance at 340 nm was read every 10 seconds for 1 h and the apparent reaction rate for 1-9 absorbance decrease was measured from between 0-5 min.

DHFS Steady State Kinetics Inhibition Assay

TABLE 14

Biochemical conditions for the DHFS kinetics inhibition assay.

| | Stock Concentration (μM) | Stock Volume (μL) | Final Concentration (μM) |
|---|---|---|---|
| MgCl$_2$ | 250000 | 6 | 10000 |
| DTT | 250000 | 3 | 5000 |
| BSA | 10 mg/mL | 15 | 1 mg/mL |
| Glycine | 1250000 | 6 | 50000 |
| PEP | 7500 | 3 | 150 |
| NADH | 5000 | 4.5 | 150 |
| Pk/Ld | 600/900 unit/mL | 25 | 100/150 unit/mL |
| ATP | 15000 | 1.5 | 150 |
| Glutamate | 7500 | 2 | 100 |
| THF | 2000 | 3.75 | 50 |
| DHFS | 100 | 4.5 | 3 |
| Total volume w/o DHFS | | 69.75 | |
| 100 mM Tris pH = 7.5 + inhibitor | | 75.75 | |
| Final Volume | | 150 | |

Stock solutions of all reagents were made using 100 mM Tris-buffer (pH=7.5) an stored in fractions in a −80° C. freezer until use. 1500 μL of a stock solution containing everything (in appropriate amounts to maintain the final concentration calculations for 150 total μL well volume) in the table above except the DHFS and the Tris Buffer+inhibitor was made. Solutions of the Tris Buffer+inhibitor were made so as to achieve final inhibitor concentrations as below. The final concentrations of inhibitor can be adjusted as necessary.

TABLE 15

Concentrations of inhibitor in each well of the DHFS kinetics inhibition assay.

| Well | Final Concentration (μM) |
|---|---|
| 1 | 0 |
| 2 | 1.77827941 |
| 3 | 5.623413252 |
| 4 | 17.7827941 |
| 5 | 56.23413252 |
| 6 | 0 |

Each necessary well of a quartz 96-well plate was flushed with argon then filled (in triplicate) with 69.75 μL of stock solution and 75.75 μL of Tris Buffer+Inhibitor solution. The quartz plate was incubated at 37° C. for 10 minutes then 4.5 μL of DHFS stock solution was quickly added to each well except well 6, to which 4.5 μL of Tris-buffer was added. The quartz plate was put in a plate reader at 37° C. and the optical absorbance at 340 nm was read every 10 seconds for 20 min. The apparent reaction rate for absorbance decrease was measured from between 0-5 min. Each well was combined with their triplicate partners and the solutions were centrifuge filtered through a molecular weight cutoff (MWCO) to remove any enzymes. The solutions were spiked with enough Fmoc-ala to bring the final concentration to 50 μM (moc-ala then run on an LCMS with single ion monitoring methods to detect the various oxidation states of THEA and Glu-THFA.

An alternative method is as follows: After the 20-minute optical absorbance reading, the triplicate solutions were combined then diluted with 200 μL MeOH and an amount of KCl in $H_2O$ to bring the final concentration of KCl to 20 mM. The solutions were then incubated at 70° C. for 1 h. The solutions were then centrifuged to remove the white precipitate that formed, then spiked with enough Fmoc-ala to bring the final concentration to 50 μM Fmoc-ala. The solutions were then run on an LCMS with single ion monitoring methods to 1-9 detect the various oxidation states of THEA and Glu-THFA.

TABLE 16: Biochemical conditions for DHFS enzymatic activity prior to protein mass spectrometry analysis.

TABLE 16

Biochemical conditions for DHFS enzymatic activity prior to protein mass spectrometry analysis.

| | Concentration (μM) |
|---|---|
| Vial A | |
| $MgCl_2$ | 10000 |
| DTT | 5000 |
| BSA | 1 mg/mL |
| Glycine | 50000 |
| ATP | 500 |
| Glu | 500 |
| 3-HβL | 40 |

TABLE 16-continued

Biochemical conditions for DHFS enzymatic activity prior to protein mass spectrometry analysis.

| | Concentration (μM) |
|---|---|
| DHFS | 20 |
| 100 mM Tris pH = 7.5 | 100 |
| Vial B | |
| $MgCl_2$ | 10000 |
| DTT | 5000 |
| BSA | 1 mg/mL |
| Glycine | 50000 |
| ATP | 500 |
| Glu | 500 |
| 3-HβL | 0 |
| DHFS | 20 |
| 100 mM Tris pH = 7.5 | 100 |
| Vial C | |
| $MgCl_2$ | 10000 |
| DTT | 5000 |
| BSA | 1 mg/mL |
| Glycine | 50000 |
| ATP | 500 |
| Glu | 500 |
| 3-HβL | 400 |
| DHFS | 20 |
| 100 mM Tris pH = 7.5 | 100 |
| Vial D | |
| $MgCl_2$ | 0 |
| DTT | 0 |
| BSA | 0 |
| Glycine | 0 |
| ATP | 0 |
| Glu | 0 |
| 3-HβL | 0 |
| DHFS | 0 |
| 100 mM Tris pH = 7.5 | 0 |

Stock solutions of all reagents were made using 100 mM Tris-buffer (pH=7.5) and stored in fractions in a −80° C. freezer until use. Vials of 200 μL solutions of A, B, C, and D were made then incubated at 37° C. for 1 hour. The vials were submitted to the Gross lab for protein mass spectrometry analysis.

Agar Plate Diffusion

An overnight culture of E. coli ATC 25922 was grown in 5 mL of LB broth. 22 g of Mueller Hinton II broth powder and 15 g of agar were dissolved in 1 L of dd-$H_2O$ and autoclaved. The MH II agar broth was cooled to 47° C. and 35 mL of MH II agar broth was inoculated with 100 μL of OD600=0.1 E. coli from the overnight culture. The inoculated agar was plated and once cool enough, 10 wells were cut out using a vacuum. Each well was filled with 50 μL DMSO solutions as below and the plates were left in an incubator at 37° C. for 18 h. The zones of inhibition were measured for each well.

TABLE 17

Inhibitor and potential inhibitor concentrations for the agar plate diffusion assay using E. coli as the bacterial target.

| Well | Compound Concentrations |
|---|---|
| 1 | DMSO |
| 2 | 3.52 mg/mL TMP |
| 3 | 15 mg/mL TMP |
| 4 | 3.52 mg/mL HβL |
| 5 | 3.52 mg/mL SMX |
| 6 | 15 mg/mL SMX |
| 7 | DMSO |

TABLE 17-continued

| Inhibitor and potential inhibitor concentrations for the agar plate diffusion assay using *E. coli* as the bacterial target. | |
|---|---|
| Well | Compound Concentrations |
| 8 | 3.52 mg/mL TMP + 3.52 mg/mL SMX |
| 9 | 3.52 mg/mL HβL + 3.52 mg/mL TMP |
| 10 | 3.52 mg/mL HβL + 3.52 mg/mL SMX |

Example 4: SAR Exploration for 3-HBL Folate Inhibitors

Herein is established that the 3-HβL pharmacophore is a potency driver for DHFS inhibition; thus, the development of a structure-activity relationship (SAR) data set is the next step for this work. Herein are described multiple pathways potentially useful for development of SAR.

Exploration Around the Stereochemistry of the 3-HβL

As discussed above, the stereochemistry at the 3C position may be important, especially if the ring were to become more substituted. As such, the cinchona alkaloids used by Deng and coworkers may be used to stereo-selectively perform the Henry reaction to set the 1N position and 3C substituents (see e.g., FIG. 42). If these catalysts are unable to afford stereoselective Henry reactions, there are other metal-based and non-metal-based catalysts that may perform asymmetric Henry reactions.

Exploration around substitution at 4C of the 3-HβL

The β-lactam ring in 4.10 was unsubstituted at the 4C position. Examination of the active site of DHFS showed that substitutions at 4C may tolerated. Given substitutions at 4C will most likely extend into the part of the active site meant to bind L-Glu, it may be possible to pick up electrostatic interactions that can enhance binding. Modifications of the Henry reaction in discussed above may be made to use alkyl-nitro compounds in lieu of nitromethane (see e.g., FIG. 43). These modifications may be carried through the rest of the route towards a 3-HβL should suitable protecting groups be chosen so as to not interfere with the rest of the reactions (potential carboxylic acids would likely need to be protected as the 2-alkyl-1,3-oxazoline). Fixing the newly important stereocenter at 4C might be possible with known Zn (II) and Cu (II) based Henry reaction catalysts.

Exploration Around Linker Length and Pterin/Amino-Pyrimidine Heterocycles

Given the pteridine used in 4.6 is capable of traversing a wide variety of bacterial cell walls, it may be useful to attach its amino-pyrimidine pterin mimic to the 3-HβL warhead in a way that allowed for potent inhibition and cell wall permeation. For example, extending the linker between the aniline and the amino-pyrimidine may allow the 3-HβL to be anchored correctly in the active site while still being able to get through cell walls. Given restrictions on what 5 substituted amino-pyrimidine compounds can be bought, extending the carbon chain from the 3-HβL side during synthesis (see e.g., FIG. 44A), building a linker to bind the 3-HβL and amino-pyrimidine together through a third molecule (see e.g., FIG. 44B), or using metathesis to create a long alkyl chain (see e.g., FIG. 44C) may be used.

Exploration Around the Aniline Linker

The nitrogen of the aniline linker proved to be synthetically difficult to achieve, but the linker may not be limited to an aniline. A phenol or a benzenethiol would provide a differently reactive handle on the aniline to make linkages to pterin mimics. Thus, the introduction of a protected phenol (see e.g., FIG. 45A) or a protected benzenethiol (see e.g., FIG. 45B) to the system in place of the protected aniline may allow for linkage with pterin mimics in an SN2 fashion.

Example 5: New Targets for 3-Hbl Inhibition

Now that the 3-HβL pharmacophore has been established herein to be a potency driver for DHFS inhibition, new ATP-dependent carboxylate-amine ligase enzyme targets may be explored for potential inhibition by 3-HβL containing molecules. D-alanine D-alanine ligase (DDL) may be the next step in 3-HβL inhibition exploration. While there are many ATP-dependent carboxylate-amine ligase enzymes, DDL was chosen based on reduced potential for off-target inhibition of human versions of each enzyme. DDL is a vital component of peptidoglycan biosynthesis and is endogenous to bacteria but not humans (much like DHFS). DDL catalyzes the ligation of two D-alanine together in an ATP-dependent manner and goes through a similar tetrahedral phosphate intermediate to DHFS and GS (see e.g., FIG. 46A). D-cycloserine is a clinically used antibiotic (used to treat *Mycobacterium tuberculosis*) that inhibits DDL, but is limited in use because it also inhibits GABA-transaminase, a vital component of mammalian neurotransmitter pathways. A new molecule, potentially a 3-HβL mimic of D-alanine, might capture the clinically relevant ability to inhibit DDL while reducing off target neurotransmission inhibition effects. A synthetic route to a potential DDL inhibitor containing a 3-HβL in FIG. 46B.

Preliminary work on the first route is depicted in FIG. 46C. The N—O-benzyl protecting group may be removed from 5.41; whereas previously, the PMB and benzyl protecting groups were not. While this discovery did not aid in synthesis as discussed in Example 1 (the N—O-benzyl protected β-lactam did not survive oxidation by osmium tetroxide or ozonolysis), a Sharpless dihydroxylation was possible on olefin 5.43. Thus, a Sharpless asymmetric aminohydroxylation on olefin 5.45 may furnish a 3-HβL that can be deprotected and used as possible inhibitor of DDL (see e.g., FIG. 46D). The facial selectivity of the aminohydroxylation with respect to the β-lactam as well as the stereochemistry associated with the N—C bond and the 3C carbon of the β-lactam may be investigated. This compound may potentially be dosed as a pro-drug like TβL and tabtoxin (see e.g., FIG. 47A-FIG. 47B).

What is claimed is:

1. A composition comprising a dihydrofolate synthase (DHFS) inhibiting agent, wherein the DHFS inhibiting agent is a compound having a 3-hydroxy-beta-lactam or a pharmaceutically acceptable salt thereof.

2. The composition of claim 1, wherein the DHFS inhibiting agent is:

-continued

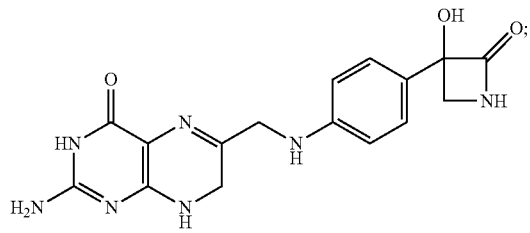

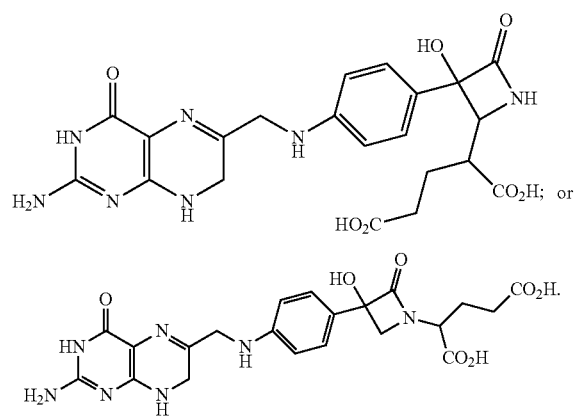

3. The composition of claim 1, wherein the DHFS inhibiting agent is selected from:

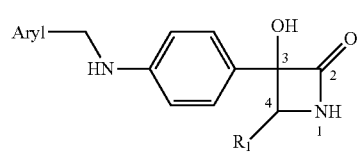

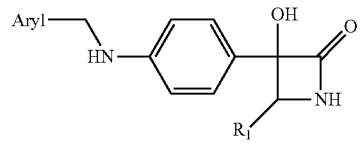

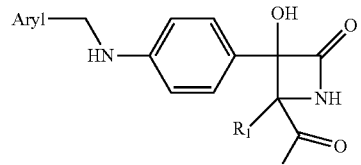

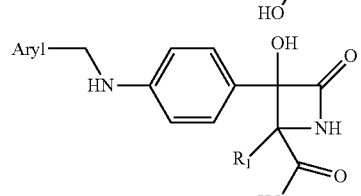

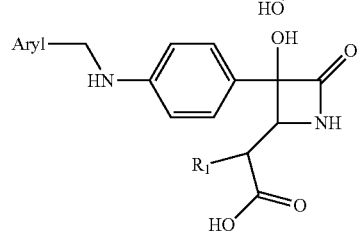

-continued

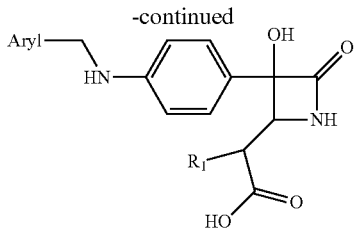

wherein $R_1$ is Me, Et, Pr, or $(CH_2)_2$—COOH and Aryl is selected from

Aryl =

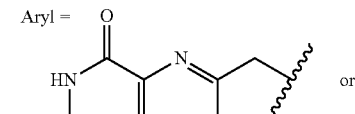  or

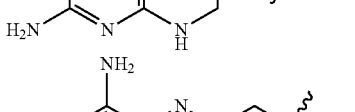  or

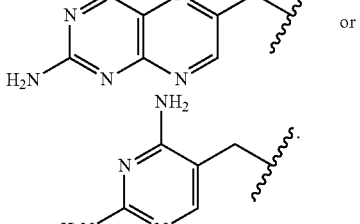

4. The composition of claim 1, wherein the DHFS inhibiting agent is:

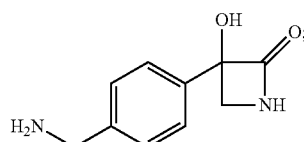

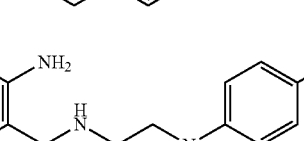

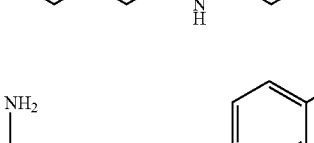

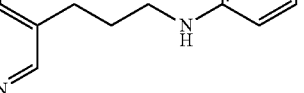

5. The composition of claim 1, wherein the DHFS inhibiting agent further consists of a lipophilic side chain, pteridine, or amino-pyrimidine pterin to enhance cell permeability.

6. The composition of claim 1, further comprising an antifolate selected from a dihydropteroate synthase (DHPS) inhibitor or a dihydrofolate reductase (DHFR) inhibitor.

7. The composition of claim 6, wherein the antifolate is trimethoprim or sulfamethoxazole.

8. The composition of claim 1, wherein the DHFS inhibiting agent mimics a tetrahedral intermediate of DHFS.

9. The composition of claim 1, wherein the DHFS inhibiting agent has an apparent IC50 of less than about 2 µM.

10. A method of inhibiting dihydrofolate synthetase (DHFS) in a subject, the method comprising:

administering a DHFS inhibiting agent to the subject, wherein the DHFS agent is a compound having a 3-hydroxy-beta-lactam or a pharmaceutically acceptable salt thereof.

11. The method of claim 10, wherein the DHFS inhibiting agent is:

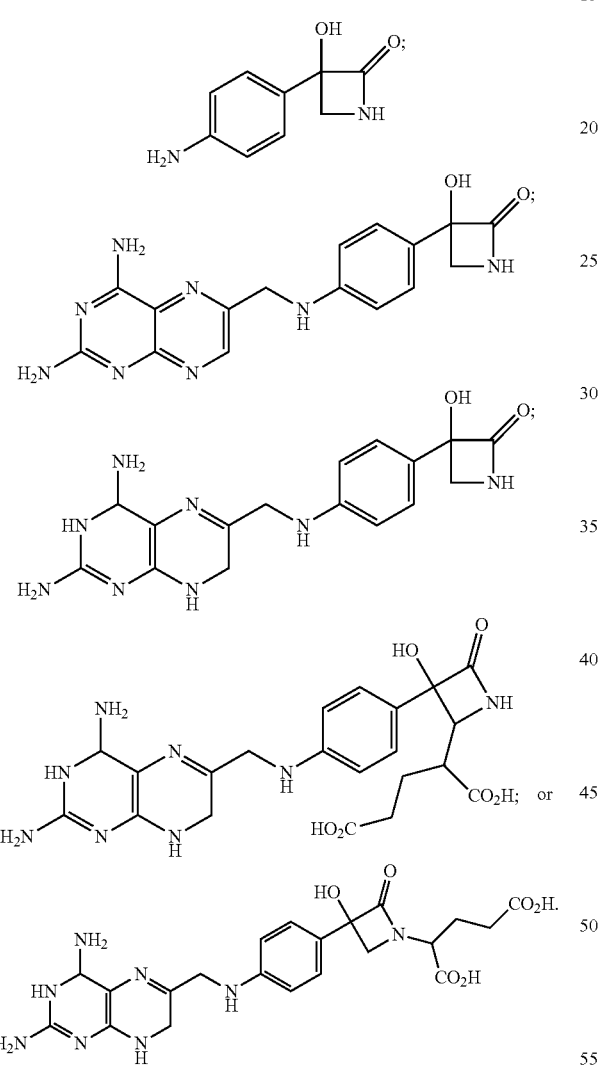

12. The method of claim 10, wherein the DHFS inhibiting agent is selected from:

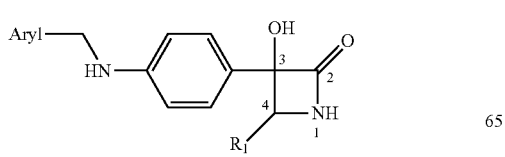

-continued

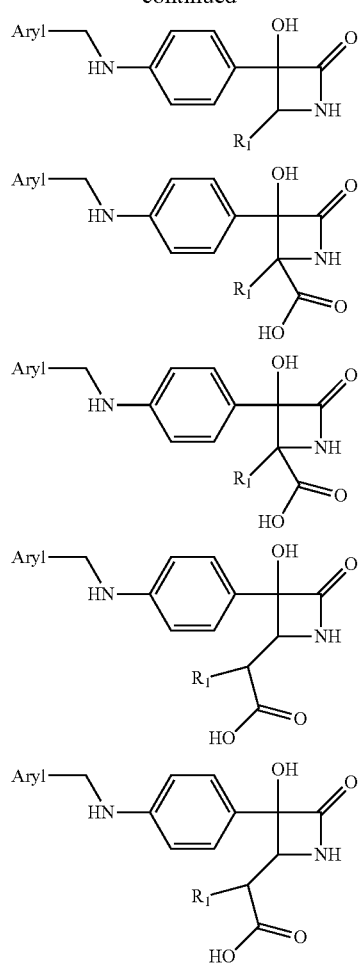

wherein $R_1$ is Me, Et, Pr, or $(CH_2)_2$—COOH and Aryl is selected from

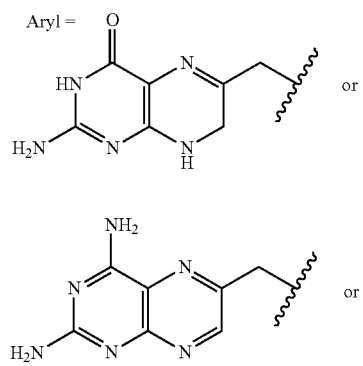

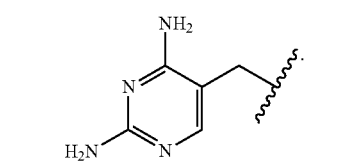

13. The method of claim 10, wherein the DHFS inhibiting agent is:

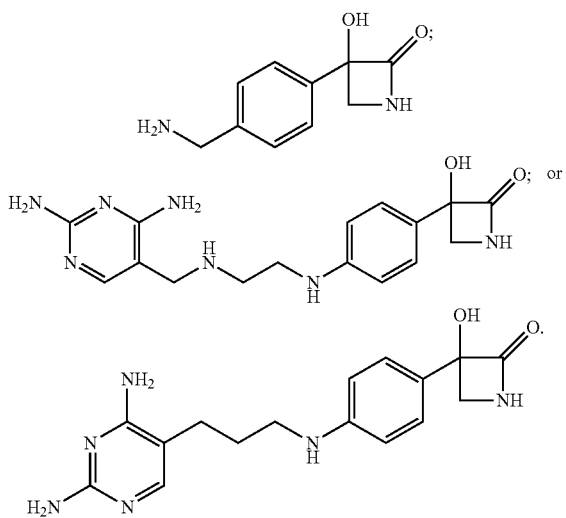

14. The method of claim 10, wherein the subject has a bacterial infection.

15. The method of claim 14, wherein the subject has an antibiotic-resistant bacterial infection.

16. The method of claim 10, further comprising administering an antifolate selected from a dihydropteroate synthase (DHPS) inhibitor or a dihydrofolate reductase (DHFR) inhibitor.

17. The method of claim 16, wherein the antifolate is trimethoprim or sulfamethoxazole.

18. A method of making a compound comprising a 3-hydroxy-beta-lactam (3-HβL), the method comprising:
adding a nitromethane group to a p-nitro-aniline derived α-keto-ester using a Henry reaction; and
using Grignard mediated-ring closing to yield a compound comprising an unprotected 3-HβL.

19. The method of claim 18, further comprising:
providing acid to prevent reverse-Henry elimination of the nitromethane group; or
providing buffered Boc protection conditions to selectively protect an aryl-nitrogen.

20. The method of claim 18, wherein the compound comprising an unprotected 3-HβL is

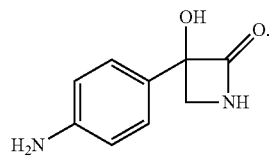

* * * * *